US011129608B2

(12) United States Patent
Catanese, III et al.

(10) Patent No.: US 11,129,608 B2
(45) Date of Patent: Sep. 28, 2021

(54) ANCHOR DELIVERY SYSTEM

(71) Applicant: NeoTract, Inc., Pleasanton, CA (US)

(72) Inventors: Joseph Catanese, III, San Leandro, CA (US); Theodore Bender, San Anselmo, CA (US); Robert George, San Jose, CA (US); Floria Cheng, San Francisco, CA (US); Jolene Cutts, San Francisco, CA (US); Ling-Kang Tong, Fremont, CA (US); Michael Gearhart, Fremont, CA (US); Matthew McLean, San Francisco, CA (US); James Niederjohn, San Jose, CA (US); Brian Y. Tachibana, Oakland, CA (US); Ben Thompson, San Carlos, CA (US)

(73) Assignee: NeoTract, Inc., Pleasanton, CA (US)

( * ) Notice: Subject to any disclaimer, the term of this patent is extended or adjusted under 35 U.S.C. 154(b) by 118 days.

(21) Appl. No.: 16/442,900

(22) Filed: Jun. 17, 2019

(65) Prior Publication Data
US 2019/0298334 A1    Oct. 3, 2019

Related U.S. Application Data

(60) Continuation of application No. 15/295,395, filed on Oct. 17, 2016, now Pat. No. 10,349,932, which is a
(Continued)

(51) Int. Cl.
*A61B 17/04* (2006.01)
*A61B 17/00* (2006.01)
(Continued)

(52) U.S. Cl.
CPC .... *A61B 17/0401* (2013.01); *A61B 17/00234* (2013.01); *A61B 17/0469* (2013.01);
(Continued)

(58) Field of Classification Search
CPC ............ A61B 17/0401; A61B 17/0469; A61B 2017/0451; A61B 2017/0454;
(Continued)

(56) References Cited

U.S. PATENT DOCUMENTS 659,422 A    10/1900   Shidler
780,392 A     1/1905   Wanamaker et al.
(Continued)

FOREIGN PATENT DOCUMENTS

CA      2477220        11/2007
CN   101795641 A       8/2010
(Continued)

OTHER PUBLICATIONS

Bacharova, O.A., et al. "The Effect of Rhodiolae rosea Extract on Incidence Rate of Superficial Bladder Carcinoma Relapses", Kozin 1995.
(Continued)

*Primary Examiner* — Erich G Herbermann
*Assistant Examiner* — Chima U Igboko
(74) *Attorney, Agent, or Firm* — Christopher J. Buchko

(57) ABSTRACT

A system and associated method for manipulating tissues and anatomical or other structures in medical applications for the purpose of treating diseases or disorders or other purposes. In one aspect, the system includes a delivery device and a plurality of anchor assemblies. The delivery system is configured to deliver a first anchor using loaded energy and reload the energy required to deliver an addition anchor.

9 Claims, 32 Drawing Sheets

Related U.S. Application Data division of application No. 13/833,299, filed on Mar. 15, 2013, now Pat. No. 9,504,461.

(51) Int. Cl.

| | |
|---|---|
| A61B 17/32 | (2006.01) |
| A61B 17/34 | (2006.01) |
| A61B 17/42 | (2006.01) |
| A61B 17/06 | (2006.01) |
| A61B 17/29 | (2006.01) |
| A61B 18/00 | (2006.01) |

(52) U.S. Cl.
CPC .......... *A61B 17/0482* (2013.01); *A61B 17/32* (2013.01); *A61B 17/3468* (2013.01); *A61B 17/3478* (2013.01); *A61B 17/42* (2013.01); *A61B 2017/00022* (2013.01); *A61B 2017/0046* (2013.01); *A61B 2017/00274* (2013.01); *A61B 2017/00792* (2013.01); *A61B 2017/00796* (2013.01); *A61B 2017/00805* (2013.01); *A61B 2017/0409* (2013.01); *A61B 2017/0417* (2013.01); *A61B 2017/0419* (2013.01); *A61B 2017/0464* (2013.01); *A61B 2017/0479* (2013.01); *A61B 2017/0488* (2013.01); *A61B 2017/06052* (2013.01); *A61B 2017/06095* (2013.01); *A61B 2017/2923* (2013.01); *A61B 2018/00547* (2013.01)

(58) Field of Classification Search
CPC .. A61B 2017/0409; A61B 2017/06052; A61B 2017/0462; A61B 2017/00274; A61B 2017/0417; A61B 2017/0419; A61B 2017/0464; A61B 17/0487; A61B 2018/00547; A61B 17/0482; A61B 17/00234; A61B 17/32; A61B 17/3468; A61B 17/3478; A61B 17/42; A61B 2017/00022; A61B 2017/0046; A61B 2017/00792; A61B 2017/00796; A61B 2017/00805; A61B 2017/0479; A61B 2017/0488; A61B 2017/06095; A61B 2017/2923; A61F 2/04
See application file for complete search history.

(56) References Cited

U.S. PATENT DOCUMENTS

| | | |
|---|---|---|
| 789,467 A | 5/1905 | West |
| 2,360,164 A | 10/1944 | Frank |
| 2,485,531 A | 10/1949 | William et al. |
| 2,579,192 A | 12/1951 | Alexander |
| 2,646,298 A | 7/1953 | Leary |
| 2,697,624 A | 12/1954 | Thomas et al. |
| 2,734,299 A | 2/1956 | Masson |
| 2,825,592 A | 3/1958 | Mckenzie |
| 3,326,586 A | 6/1967 | Frost et al. |
| 3,470,834 A | 10/1969 | Bone |
| 3,521,918 A | 7/1970 | Hammond |
| 3,541,591 A | 11/1970 | Hoegerman |
| 3,664,345 A | 5/1972 | Dabbs et al. |
| 3,713,680 A | 1/1973 | Pagano |
| 3,716,058 A | 2/1973 | Tanner |
| 3,756,638 A | 9/1973 | Stockberger |
| 3,873,140 A | 3/1975 | Bloch |
| 3,875,648 A | 4/1975 | Bone |
| 3,886,933 A | 6/1975 | Mori et al. |
| 3,931,667 A | 1/1976 | Merser et al. |
| 3,976,079 A | 8/1976 | Samuels et al. |
| 4,006,747 A | 2/1977 | Kronenthal et al. |
| 4,137,920 A | 2/1979 | Bonnet |
| 4,164,225 A | 8/1979 | Johnson et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,419,094 A | 12/1983 | Patel |
| 4,493,323 A | 1/1985 | Albright et al. |
| 4,513,746 A | 4/1985 | Aranyi et al. |
| 4,621,640 A | 11/1986 | Mulhollan et al. |
| 4,655,771 A | 4/1987 | Wallsten |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,863,439 A | 9/1989 | Sanderson |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna |
| 5,002,550 A | 3/1991 | Li |
| 5,019,032 A | 5/1991 | Robertson |
| 5,041,129 A | 8/1991 | Hayhurst et al. |
| 5,046,513 A | 9/1991 | Gatturna et al. |
| 5,053,046 A | 10/1991 | Janese |
| 5,078,731 A | 1/1992 | Hayhurst |
| 5,080,660 A | 1/1992 | Buelna |
| 5,098,374 A | 3/1992 | Othel-Jacobsen et al. |
| 5,100,421 A | 3/1992 | Christoudias |
| 5,123,914 A | 6/1992 | Cope |
| 5,127,393 A | 7/1992 | McFarlin et al. |
| 5,129,912 A | 7/1992 | Noda et al. |
| 5,133,713 A | 7/1992 | Huang et al. |
| 5,159,925 A | 11/1992 | Neuwirth et al. |
| 5,160,339 A | 11/1992 | Chen et al. |
| 5,192,303 A | 3/1993 | Gatturna et al. |
| 5,203,787 A | 4/1993 | Noblitt et al. |
| 5,207,672 A | 5/1993 | Roth et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,237,984 A | 8/1993 | Williams et al. |
| 5,258,015 A | 11/1993 | Li et al. |
| 5,267,960 A | 12/1993 | Hayman et al. |
| 5,269,802 A | 12/1993 | Garber |
| 5,269,809 A | 12/1993 | Hayhurst et al. |
| 5,300,099 A | 4/1994 | Rudie |
| 5,322,501 A | 6/1994 | Mahmud-Durrani |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | Torre |
| 5,478,003 A | 12/1995 | Green et al. |
| 5,480,406 A | 1/1996 | Nolan et al. |
| 5,499,994 A | 3/1996 | Tihon et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |

(56) References Cited

U.S. PATENT DOCUMENTS

| | | |
|---|---|---|
| 5,540,655 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,549,631 A | 8/1996 | Bonutti |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake et al. |
| 5,665,109 A | 9/1997 | Yoon |
| 5,667,486 A | 9/1997 | Mikulich et al. |
| 5,667,488 A | 9/1997 | Lundquist et al. |
| 5,669,917 A | 9/1997 | Sauer et al. |
| 5,690,649 A | 11/1997 | Li |
| 5,690,677 A | 11/1997 | Schmieding et al. |
| 5,697,950 A | 12/1997 | Fucci et al. |
| 5,707,394 A | 1/1998 | Miller et al. |
| 5,716,368 A | 2/1998 | Torre et al. |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,749,889 A | 5/1998 | Bacich et al. |
| 5,752,963 A | 5/1998 | Allard et al. |
| 5,782,862 A | 7/1998 | Bonutti |
| 5,782,864 A | 7/1998 | Lizardi |
| 5,791,022 A | 8/1998 | Bohman |
| 5,800,445 A | 9/1998 | Ratcliff et al. |
| 5,807,403 A | 9/1998 | Beyar et al. |
| 5,810,848 A | 9/1998 | Hayhurst |
| 5,810,853 A | 9/1998 | Yoon |
| 5,814,072 A | 9/1998 | Bonutti |
| 5,830,179 A | 11/1998 | Mikus et al. |
| 5,830,221 A | 11/1998 | Stein et al. |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,879,357 A | 3/1999 | Heaton et al. |
| 5,897,574 A | 4/1999 | Bonutti |
| 5,899,911 A | 5/1999 | Carter |
| 5,899,921 A | 5/1999 | Caspari et al. |
| 5,904,679 A | 5/1999 | Clayman |
| 5,904,696 A | 5/1999 | Rosenman |
| 5,908,428 A | 6/1999 | Scirica et al. |
| 5,908,447 A | 6/1999 | Schroeppel et al. |
| 5,919,198 A | 7/1999 | Graves et al. |
| 5,919,202 A | 7/1999 | Yoon |
| 5,921,982 A | 7/1999 | Lesh et al. |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,731 A | 9/1999 | Yoon |
| 5,954,747 A | 9/1999 | Clark |
| 5,964,732 A | 10/1999 | Willard |
| 5,971,447 A | 10/1999 | Steck |
| 5,971,967 A | 10/1999 | Willard |
| 6,010,514 A | 1/2000 | Burney et al. |
| 6,011,525 A | 1/2000 | Piole |
| 6,015,428 A | 1/2000 | Pagedas |
| 6,030,393 A | 2/2000 | Corlew |
| 6,033,413 A | 3/2000 | Mikus et al. |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,066,160 A | 5/2000 | Colvin et al. |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,133 A | 9/2000 | Zappala |
| 6,117,160 A | 9/2000 | Bonutti |
| 6,117,161 A | 9/2000 | Li et al. |
| 6,120,539 A | 9/2000 | Eldridge et al. |
| 6,132,438 A | 10/2000 | Fleischman et al. |
| 6,139,555 A | 10/2000 | Hart et al. |
| RE36,974 E | 11/2000 | Bonutti |
| 6,143,006 A | 11/2000 | Chan |
| 6,152,935 A | 11/2000 | Kammerer et al. |
| 6,156,044 A | 12/2000 | Kammerer et al. |
| 6,159,207 A | 12/2000 | Yoon |
| 6,159,234 A | 12/2000 | Bonutti et al. |
| 6,200,329 B1 | 3/2001 | Fung et al. |
| 6,206,895 B1 | 3/2001 | Levinson |
| 6,206,907 B1 | 3/2001 | Marino et al. |
| 6,228,096 B1 | 5/2001 | Marchand |
| 6,258,124 B1 | 7/2001 | Darois et al. |
| 6,261,302 B1 | 7/2001 | Voegele et al. |
| 6,270,530 B1 | 8/2001 | Eldridge et al. |
| 6,280,460 B1 | 8/2001 | Bolduc et al. |
| 6,287,317 B1 | 9/2001 | Makower et al. |
| 6,290,711 B1 | 9/2001 | Caspari et al. |
| 6,306,158 B1 | 10/2001 | Bartlett |
| 6,312,448 B1 | 11/2001 | Bonutti |
| 6,319,263 B1 | 11/2001 | Levinson |
| 6,322,112 B1 | 11/2001 | Duncan |
| 6,332,889 B1 | 12/2001 | Sancoff et al. |
| 6,382,214 B1 | 5/2002 | Raz et al. |
| 6,398,795 B1 | 6/2002 | McAlister et al. |
| 6,423,079 B1* | 7/2002 | Blake, III ........... A61B 17/1285 606/143 |
| 6,425,900 B1* | 7/2002 | Knodel ................ A61B 17/064 606/139 |
| 6,425,919 B1 | 7/2002 | Lambrecht |
| 6,428,562 B2 | 8/2002 | Bonutti |
| 6,436,107 B1 | 8/2002 | Wang et al. |
| 6,461,355 B2 | 10/2002 | Svejkovsky et al. |
| 6,482,235 B1 | 11/2002 | Lambrecht et al. |
| 6,488,691 B1 | 12/2002 | Carroll et al. |
| 6,491,707 B2 | 12/2002 | Makower et al. |
| 6,494,888 B1 | 12/2002 | Laufer et al. |
| 6,500,184 B1 | 12/2002 | Chan et al. |
| 6,500,195 B2 | 12/2002 | Bonutti |
| 6,506,190 B1 | 1/2003 | Walshe |
| 6,506,196 B1 | 1/2003 | Laufer |
| 6,517,569 B2 | 2/2003 | Mikus et al. |
| 6,527,702 B2 | 3/2003 | Whalen et al. |
| 6,527,794 B1 | 3/2003 | McDevitt et al. |
| 6,530,932 B1 | 3/2003 | Swayze et al. |
| 6,533,796 B1 | 3/2003 | Sauer et al. |
| 6,544,230 B1 | 4/2003 | Flaherty et al. |
| 6,547,725 B1 | 4/2003 | Paolitto et al. |
| 6,551,328 B2 | 4/2003 | Kortenbach |
| 6,551,333 B2 | 4/2003 | Kuhns et al. |
| 6,565,578 B1 | 5/2003 | Peifer et al. |
| 6,569,187 B1 | 5/2003 | Bonutti et al. |
| 6,572,626 B1 | 6/2003 | Knodel et al. |
| 6,572,635 B1 | 6/2003 | Bonutti |
| 6,572,653 B1 | 6/2003 | Simonson |
| 6,582,453 B1 | 6/2003 | Tran et al. |
| 6,592,609 B1 | 7/2003 | Bonutti |
| 6,596,013 B2 | 7/2003 | Yang et al. |
| 6,599,311 B1 | 7/2003 | Biggs et al. |

(56) References Cited

U.S. PATENT DOCUMENTS

| | | |
|---|---|---|
| 6,626,913 B1 | 9/2003 | McKinnon et al. |
| 6,626,916 B1 | 9/2003 | Yeung et al. |
| 6,626,919 B1 | 9/2003 | Swanstrom |
| 6,629,534 B1 | 10/2003 | Goar et al. |
| 6,641,524 B2 | 11/2003 | Kovac |
| 6,641,592 B1 | 11/2003 | Sauer et al. |
| 6,656,182 B1 | 12/2003 | Hayhurst |
| 6,660,008 B1 | 12/2003 | Foerster et al. |
| 6,660,023 B2 | 12/2003 | McDevitt et al. |
| 6,663,589 B1 | 12/2003 | Halevy |
| 6,663,633 B1 | 12/2003 | Pierson |
| 6,663,639 B1 | 12/2003 | Laufer et al. |
| 6,699,263 B2 | 3/2004 | Cope |
| 6,702,846 B2 | 3/2004 | Mikus et al. |
| 6,706,047 B2 | 3/2004 | Trout et al. |
| 6,709,493 B2 | 3/2004 | DeGuiseppi et al. |
| 6,715,804 B2 | 4/2004 | Beers |
| 6,719,709 B2 | 4/2004 | Whalen et al. |
| 6,730,112 B2 | 5/2004 | Levinson |
| 6,736,823 B2 | 5/2004 | Darois et al. |
| 6,736,854 B2 | 5/2004 | Vadurro et al. |
| 6,740,098 B2 | 5/2004 | Abrams et al. |
| 6,767,037 B2 | 7/2004 | Wenstrom |
| 6,770,076 B2 | 8/2004 | Foerster |
| 6,773,438 B1 | 8/2004 | Knodel et al. |
| 6,773,441 B1 | 8/2004 | Laufer et al. |
| 6,790,213 B2 | 9/2004 | Cherok et al. |
| 6,802,846 B2 | 10/2004 | Hauschild et al. |
| 6,821,282 B2 | 11/2004 | Perry et al. |
| 6,821,285 B2 | 11/2004 | Laufer et al. |
| 6,821,291 B2 | 11/2004 | Bolea et al. |
| 6,835,200 B2 | 12/2004 | Laufer et al. |
| 6,905,475 B2 | 6/2005 | Hauschild et al. |
| 6,908,473 B2 | 6/2005 | Skiba et al. |
| 6,921,361 B2 | 7/2005 | Suzuki et al. |
| 6,926,732 B2 | 8/2005 | Derus et al. |
| 6,951,565 B2 | 10/2005 | Keane et al. |
| 6,986,775 B2 | 1/2006 | Morales et al. |
| 6,986,784 B1 | 1/2006 | Weiser et al. |
| 6,991,596 B2 | 1/2006 | Whalen et al. |
| 6,991,647 B2 | 1/2006 | Jadhav |
| 6,997,940 B2 | 2/2006 | Bonutti |
| 7,001,327 B2 | 2/2006 | Whalen et al. |
| 7,008,381 B2 | 3/2006 | Janssens |
| 7,011,688 B2 | 3/2006 | Gryska et al. |
| 7,015,253 B2 | 3/2006 | Escandon et al. |
| 7,041,111 B2 | 5/2006 | Chu |
| 7,048,698 B2 | 5/2006 | Whalen et al. |
| 7,048,747 B2 | 5/2006 | Arcia et al. |
| 7,060,077 B2 | 6/2006 | Gordon et al. |
| 7,063,715 B2 | 6/2006 | Onuki et al. |
| 7,081,126 B2 | 7/2006 | McDevitt et al. |
| 7,083,638 B2 | 8/2006 | Foerster |
| 7,087,073 B2 | 8/2006 | Bonutti |
| 7,089,064 B2 | 8/2006 | Manker et al. |
| 7,090,690 B2 | 8/2006 | Foerster et al. |
| 7,093,601 B2 | 8/2006 | Manker et al. |
| 7,105,004 B2 | 9/2006 | DiCesare et al. |
| 7,108,655 B2 | 9/2006 | Whalen et al. |
| 7,141,038 B2 | 11/2006 | Whalen et al. |
| 7,153,314 B2 | 12/2006 | Laufer et al. |
| 7,179,225 B2 | 2/2007 | Shluzas et al. |
| 7,226,558 B2 | 6/2007 | Nieman et al. |
| 7,232,448 B2 | 6/2007 | Battles et al. |
| 7,255,675 B2 | 8/2007 | Gertner et al. |
| 7,288,063 B2 | 10/2007 | Petros et al. |
| 7,303,108 B2 | 12/2007 | Shelton |
| 7,320,701 B2 | 1/2008 | Haut et al. |
| 7,322,974 B2 | 1/2008 | Swoyer et al. |
| 7,326,221 B2 | 2/2008 | Sakamoto et al. |
| 7,334,822 B1 | 2/2008 | Hines |
| 7,340,300 B2 | 3/2008 | Christopherson et al. |
| 7,399,304 B2 | 7/2008 | Gambale et al. |
| 7,402,166 B2 | 7/2008 | Feigl |
| 7,416,554 B2 | 8/2008 | Lam et al. |
| 7,417,175 B2 | 8/2008 | Oda et al. |
| 7,463,934 B2 | 12/2008 | Tronnes et al. |
| 7,481,771 B2 | 1/2009 | Fonseca et al. |
| 7,553,317 B2 | 6/2009 | William et al. |
| 7,608,108 B2 | 10/2009 | Bhatnagar et al. |
| 7,645,286 B2 | 1/2010 | Catanese et al. |
| 7,658,311 B2 | 2/2010 | Boudreaux |
| 7,674,275 B2 | 3/2010 | Martin et al. |
| 7,695,494 B2 | 4/2010 | Foerster |
| 7,704,261 B2 | 4/2010 | Sakamoto et al. |
| 7,727,248 B2 | 6/2010 | Smith et al. |
| 7,736,374 B2 | 6/2010 | Vaughan et al. |
| 7,758,594 B2 | 7/2010 | Lamson et al. |
| 7,766,923 B2 | 8/2010 | Catanese et al. |
| 7,766,939 B2 | 8/2010 | Yeung et al. |
| 7,780,682 B2 | 8/2010 | Catanese et al. |
| 7,815,655 B2 | 10/2010 | Catanese et al. |
| 7,887,551 B2 | 2/2011 | Bojarski et al. |
| 7,896,891 B2 | 3/2011 | Catanese et al. |
| 7,905,889 B2 | 3/2011 | Catanese et al. |
| 7,909,836 B2 | 3/2011 | McLean et al. |
| 7,914,542 B2 | 3/2011 | Lamson et al. |
| 7,951,158 B2 | 5/2011 | Catanese et al. |
| 8,007,503 B2 | 8/2011 | Catanese et al. |
| 8,043,309 B2 | 10/2011 | Catanese et al. |
| 8,157,815 B2 | 4/2012 | Catanese et al. |
| 8,211,118 B2 | 7/2012 | Catanese et al. |
| 8,216,254 B2 | 7/2012 | McLean et al. |
| 8,333,776 B2 | 12/2012 | Cheng et al. |
| 8,343,187 B2 | 1/2013 | Lamson et al. |
| 8,394,110 B2 | 3/2013 | Catanese et al. |
| 8,394,113 B2 | 3/2013 | Wei et al. |
| 8,425,535 B2 | 4/2013 | McLean et al. |
| 8,454,655 B2 | 6/2013 | Yeung et al. |
| 8,491,606 B2 | 7/2013 | Tong et al. |
| 8,529,584 B2 | 9/2013 | Catanese et al. |
| 8,603,106 B2 | 12/2013 | Catanese et al. |
| 8,628,542 B2 | 1/2014 | Merrick et al. |
| 8,663,243 B2 | 3/2014 | Lamson et al. |
| 8,668,705 B2 | 3/2014 | Johnston et al. |
| 8,715,239 B2 | 5/2014 | Lamson et al. |
| 8,715,298 B2 | 5/2014 | Catanese et al. |
| 9,504,461 B2 | 11/2016 | Catanese et al. |
| 2001/0041916 A1 | 11/2001 | Bonutti |
| 2001/0044639 A1 | 11/2001 | Levinson |
| 2002/0095064 A1 | 7/2002 | Beyar |
| 2002/0095154 A1 | 7/2002 | Atkinson et al. |
| 2002/0107540 A1 | 8/2002 | Whalen et al. |
| 2002/0128684 A1 | 9/2002 | Foerster |
| 2002/0161382 A1 | 10/2002 | Neisz et al. |
| 2002/0183740 A1 | 12/2002 | Edwards et al. |
| 2002/0193809 A1 | 12/2002 | Meade et al. |
| 2003/0060819 A1 | 3/2003 | McGovern et al. |
| 2003/0109769 A1 | 6/2003 | Lowery et al. |
| 2003/0191497 A1 | 10/2003 | Cope |
| 2003/0199860 A1 | 10/2003 | Loeb et al. |
| 2003/0204195 A1 | 10/2003 | Keane et al. |
| 2003/0236535 A1 | 12/2003 | Onuki et al. |
| 2004/0030217 A1 | 2/2004 | Yeung et al. |
| 2004/0043052 A1 | 3/2004 | Hunter et al. |
| 2004/0078046 A1 | 4/2004 | Barzell et al. |
| 2004/0122456 A1 | 6/2004 | Saadat et al. |
| 2004/0122474 A1 | 6/2004 | Gellman et al. |
| 2004/0147958 A1 | 7/2004 | Lam et al. |
| 2004/0193191 A1 | 9/2004 | Starksen et al. |
| 2004/0193194 A1 | 9/2004 | Laufer et al. |
| 2004/0194790 A1 | 10/2004 | Laufer et al. |
| 2004/0243178 A1 | 12/2004 | Haut et al. |
| 2004/0243179 A1 | 12/2004 | Foerster |
| 2004/0243180 A1 | 12/2004 | Donnelly et al. |
| 2004/0243227 A1 | 12/2004 | Starksen et al. |
| 2004/0260345 A1 | 12/2004 | Foerster |
| 2005/0010203 A1 | 1/2005 | Edwards et al. |
| 2005/0055087 A1 | 3/2005 | Starksen |
| 2005/0065550 A1 | 3/2005 | Starksen et al. |
| 2005/0107811 A1 | 5/2005 | Starksen et al. |
| 2005/0107812 A1 | 5/2005 | Starksen et al. |
| 2005/0154401 A1 | 7/2005 | Weldon et al. |
| 2005/0165272 A1 | 7/2005 | Okada et al. |

(56) References Cited

U.S. PATENT DOCUMENTS

| | | |
|---|---|---|
| 2005/0177181 A1 | 8/2005 | Kagan et al. |
| 2005/0203344 A1 | 9/2005 | Orban et al. |
| 2005/0203550 A1 | 9/2005 | Laufer et al. |
| 2005/0216040 A1 | 9/2005 | Gertner et al. |
| 2005/0216078 A1 | 9/2005 | Starksen et al. |
| 2005/0251157 A1 | 11/2005 | Saadat et al. |
| 2005/0251206 A1 | 11/2005 | Maahs et al. |
| 2005/0267405 A1 | 12/2005 | Shah |
| 2005/0273138 A1 | 12/2005 | To et al. |
| 2006/0025750 A1 | 2/2006 | Starksen et al. |
| 2006/0025784 A1 | 2/2006 | Starksen et al. |
| 2006/0025789 A1 | 2/2006 | Laufer et al. |
| 2006/0025819 A1 | 2/2006 | Nobis et al. |
| 2006/0026750 A1 | 2/2006 | Ballance |
| 2006/0030884 A1 | 2/2006 | Yeung et al. |
| 2006/0058817 A1 | 3/2006 | Starksen et al. |
| 2006/0089646 A1 | 4/2006 | Bonutti |
| 2006/0167477 A1 | 7/2006 | Arcia et al. |
| 2006/0199996 A1 | 9/2006 | Caraballo et al. |
| 2006/0241694 A1 | 10/2006 | Cerundolo |
| 2006/0265042 A1 | 11/2006 | Catanese et al. |
| 2006/0276481 A1 | 12/2006 | Evrard et al. |
| 2006/0276871 A1 | 12/2006 | Lamson et al. |
| 2006/0282081 A1 | 12/2006 | Fanton et al. |
| 2007/0049929 A1 | 3/2007 | Catanese et al. |
| 2007/0049970 A1 | 3/2007 | Belef et al. |
| 2007/0060931 A1 | 3/2007 | Hamilton et al. |
| 2007/0088362 A1 | 4/2007 | Bonutti et al. |
| 2007/0112385 A1 | 5/2007 | Conlon |
| 2007/0142846 A1 | 6/2007 | Catanese et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0021485 A1 | 1/2008 | Catanese et al. |
| 2008/0033458 A1 | 2/2008 | McLean et al. |
| 2008/0033488 A1 | 2/2008 | Catanese et al. |
| 2008/0039833 A1 | 2/2008 | Catanese et al. |
| 2008/0039872 A1 | 2/2008 | Catanese et al. |
| 2008/0039874 A1 | 2/2008 | Catanese et al. |
| 2008/0039875 A1 | 2/2008 | Catanese et al. |
| 2008/0039893 A1 | 2/2008 | McLean et al. |
| 2008/0039894 A1 | 2/2008 | Catanese et al. |
| 2008/0045978 A1 | 2/2008 | Kuhns et al. |
| 2008/0051810 A1 | 2/2008 | To et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0161852 A1 | 7/2008 | Kaiser |
| 2008/0195145 A1 | 8/2008 | Bonutti et al. |
| 2008/0208220 A1 | 8/2008 | Shiono et al. |
| 2008/0228202 A1 | 9/2008 | Cropper et al. |
| 2008/0269737 A1 | 10/2008 | Elmouelhi et al. |
| 2009/0012537 A1 | 1/2009 | Green |
| 2009/0018553 A1 | 1/2009 | McLean et al. |
| 2009/0060977 A1 | 3/2009 | Lamson et al. |
| 2009/0112234 A1 | 4/2009 | Crainich et al. |
| 2009/0112537 A1 | 4/2009 | Okumura |
| 2010/0010631 A1 | 1/2010 | Otte et al. |
| 2010/0023024 A1 | 1/2010 | Zeiner et al. |
| 2010/0030262 A1 | 2/2010 | McLean et al. |
| 2010/0030263 A1 | 2/2010 | Cheng et al. |
| 2010/0063542 A1 | 3/2010 | Burg et al. |
| 2010/0114162 A1 | 5/2010 | Bojarski et al. |
| 2010/0240951 A1* | 9/2010 | Catanese, III ......... A61B 17/10 600/104 |
| 2010/0286106 A1 | 11/2010 | Gat et al. |
| 2010/0286679 A1 | 11/2010 | Hoey et al. |
| 2010/0298948 A1 | 11/2010 | Hoey et al. |
| 2011/0040312 A1 | 2/2011 | Lamson et al. |
| 2011/0046648 A1 | 2/2011 | Johnston et al. |
| 2011/0060349 A1 | 3/2011 | Cheng et al. |
| 2011/0160747 A1 | 6/2011 | McLean et al. |
| 2011/0166564 A1 | 7/2011 | Merrick et al. |
| 2011/0190758 A1 | 8/2011 | Lamson et al. |
| 2011/0218387 A1 | 9/2011 | Lamson et al. |
| 2011/0245828 A1 | 10/2011 | Baxter et al. |
| 2012/0245600 A1 | 9/2012 | McLean et al. |
| 2012/0265006 A1 | 10/2012 | Makower et al. |
| 2013/0096582 A1 | 4/2013 | Cheng et al. |
| 2013/0211431 A1 | 8/2013 | Wei et al. |
| 2013/0253574 A1 | 9/2013 | Catanese et al. |
| 2013/0253662 A1 | 9/2013 | Lamson et al. |
| 2013/0261383 A1 | 10/2013 | Catanese et al. |
| 2013/0261665 A1 | 10/2013 | Yeung et al. |
| 2013/0267772 A1 | 10/2013 | Catanese et al. |
| 2013/0268001 A1 | 10/2013 | Catanese et al. |
| 2013/0274799 A1 | 10/2013 | Catanese et al. |
| 2013/0289342 A1 | 10/2013 | Tong et al. |
| 2013/0296639 A1 | 11/2013 | Lamson et al. |
| 2013/0296889 A1 | 11/2013 | Tong et al. |
| 2013/0296935 A1 | 11/2013 | McLean et al. |
| 2013/0325143 A1 | 12/2013 | Lamson et al. |
| 2014/0005473 A1 | 1/2014 | Catanese et al. |
| 2014/0005690 A1 | 1/2014 | Catanese et al. |
| 2014/0088587 A1 | 3/2014 | Merrick et al. |
| 2014/0236230 A1 | 8/2014 | Johnston et al. |
| 2017/0035410 A1 | 2/2017 | Catanese et al. |

FOREIGN PATENT DOCUMENTS

| | | |
|---|---|---|
| CN | 102112064 B | 6/2014 |
| DE | 10159470 A1 | 6/2003 |
| EP | 0246836 B1 | 12/1991 |
| EP | 0464480 A1 | 1/1992 |
| EP | 0632999 A1 | 1/1995 |
| EP | 1016377 A2 | 7/2000 |
| EP | 1482841 A1 | 12/2004 |
| EP | 1082941 B1 | 3/2005 |
| EP | 1006909 B1 | 1/2007 |
| EP | 1852071 A2 | 11/2007 |
| EP | 1584295 B1 | 2/2008 |
| EP | 1884198 A2 | 2/2008 |
| EP | 1884199 A1 | 2/2008 |
| EP | 1887976 A2 | 2/2008 |
| EP | 1670361 B1 | 4/2008 |
| EP | 1962720 B1 | 9/2008 |
| EP | 1331886 B1 | 12/2008 |
| EP | 1482840 B1 | 12/2008 |
| EP | 2111167 A1 | 10/2009 |
| EP | 2164427 B1 | 3/2010 |
| EP | 1484023 B1 | 5/2011 |
| EP | 2339970 A2 | 7/2011 |
| EP | 2345373 A1 | 7/2011 |
| EP | 2345374 A1 | 7/2011 |
| EP | 2600781 A2 | 6/2013 |
| EP | 2658458 A2 | 11/2013 |
| EP | 2658477 A2 | 11/2013 |
| EP | 2049023 B1 | 12/2014 |
| EP | 2344048 B1 | 9/2016 |
| FR | 2750031 A1 | 12/1997 |
| JP | 5836559 A | 3/1983 |
| JP | 09122134 | 5/1997 |
| JP | 2001137254 A | 5/2001 |
| JP | 2004341127 A | 12/2004 |
| JP | 2009106755 A | 5/2009 |
| JP | 2009521278 A | 6/2009 |
| JP | 2011529745 A | 12/2011 |
| JP | 2012143622 A | 8/2012 |
| RU | 2062121 C1 | 6/1996 |
| RU | 2112571 C1 | 6/1998 |
| RU | 2128012 C1 | 3/1999 |
| RU | 2221501 C2 | 1/2004 |
| SU | 825094 A1 | 4/1981 |
| WO | 1987001270 A1 | 3/1987 |
| WO | 1991008708 A1 | 6/1991 |
| WO | 1992010142 A1 | 6/1992 |
| WO | 1993004727 A1 | 3/1993 |
| WO | 1993015664 A1 | 8/1993 |

(56) References Cited

FOREIGN PATENT DOCUMENTS

| WO | 1995000818 A1 | 1/1995 |
|---|---|---|
| WO | 2000040159 A1 | 7/2000 |
| WO | 2001026588 A2 | 4/2001 |
| WO | 2001028432 A1 | 4/2001 |
| WO | 2001039671 A1 | 6/2001 |
| WO | 2001049195 A1 | 7/2001 |
| WO | 2001065997 A2 | 9/2001 |
| WO | 2001095818 A1 | 12/2001 |
| WO | 2002028289 A1 | 4/2002 |
| WO | 2002030335 A2 | 4/2002 |
| WO | 2002032321 A1 | 4/2002 |
| WO | 2003039334 A2 | 5/2003 |
| WO | 2003077772 A1 | 9/2003 |
| WO | 2004000159 A2 | 12/2003 |
| WO | 2004017845 A1 | 3/2004 |
| WO | 2004019787 A2 | 3/2004 |
| WO | 2004019788 A2 | 3/2004 |
| WO | 2004030569 A2 | 4/2004 |
| WO | 2004103189 A1 | 12/2004 |
| WO | 2005034738 A2 | 4/2005 |
| WO | 2005094447 A2 | 10/2005 |
| WO | 2006127431 A2 | 11/2006 |
| WO | 2007053516 A2 | 5/2007 |
| WO | 2007064906 A2 | 6/2007 |
| WO | 2007075981 A2 | 7/2007 |
| WO | 2008006084 A2 | 1/2008 |
| WO | 2008014191 A2 | 1/2008 |
| WO | 2008043044 A2 | 4/2008 |
| WO | 2008043917 A2 | 4/2008 |
| WO | 2008097942 A1 | 8/2008 |
| WO | 2009009617 A1 | 1/2009 |
| WO | 2009135005 A1 | 11/2009 |
| WO | 2010011832 A1 | 1/2010 |
| WO | 2010014821 A2 | 2/2010 |
| WO | 2010014825 A1 | 2/2010 |
| WO | 2012018446 A2 | 2/2012 |
| WO | 2012091952 A2 | 7/2012 |
| WO | 2012091954 A2 | 7/2012 |
| WO | 2012091955 A2 | 7/2012 |
| WO | 2012091956 A2 | 7/2012 |

OTHER PUBLICATIONS

Berges, Richard, et al. "Alternative Minimalinvasive Therapien Beim Benignen Prostatasyndrom", Medizin, Jg. 104, Heft 37, Sep. 14, 2007.
Borzhievski, et al., "Tactics of the Surgical Treatment of Patients With Prostatic Adenoma and Acute Urinary Retention," Urologia Nefrol (Mosk), Jan.-Feb. 1987, (1):39-43.
Hartung, Rudolf, et al. "Instrumentelle Therapie der benignen Prostatahyperplasie", Medizin, Deutsches Arzteblatt 97, Heft 15, Apr. 14, 2000.
Hofner, Klaus, et al., "Operative Therapie des benignen Prostatasyndroms", Medizin, Dtsch Arztebl, 2007; 104(36): A 2424-9.
Hubmann, R. "Geschichte der transurethralen Prostataeingriffe", Geschichte der Medizin, Urologe [B], 2000, 40:152-160.
Jonas, U., et al., "Benigne Prostatahyperplasie", Der Urologe 2006—[Sonderheft] 45:134-144.
Kruck, S., et al., "Aktuelle Therapiemoglichkeiten des Benignen Prostata-Syndroms", J Urol Urogynakol, 2009; 16(1): 19-22.
Miyake, Osamu. "Medical Examination and Treatment for BPH," Pharma Med, vol. 22, No. 3, 2004, p. 97-103.
Reich, O., et al., "Benignes Prostatasyndrom (BPS)," Der Urologe A Issue vol. 45, No. 6, Jun. 2006, p. 769-782.
Schauer, P., et al. "New applications for endoscopy: the emerging field of endoluminal and transgastric bariatric surgery", Surgical Endoscopy, (Apr. 24, 2006), 10 pgs.
Sharp, Howard T., M.D., et al. "Instruments and Methods—The 4-S Modification of the Roeder Knot: How to Tie It", Obstetrics & Gynecology, p. 1004-1006, vol. 90, No. 6, Dec. 1997.
Takashi, Daito. "Low-Invasive Treatment for BPH", Medico vol. 34, No. 10, p. 366-369, 2000.
Teruhisa, Ohashi. "Urinary Dysfunction by Lower Urinary Tract Obstruction in Male", Pharma Medica, vol. 8, No. 8, p. 35-39, 1990.
Tomohiko, Koyanagi, et al., "Surgery View of 21st Century," Urological Surgery, vol. 84, No. 1, p. 47-53, 2001.
Trapeznikov, et al., "New Technologies in the Treatment of Benign Prostatic Hyperplasia", Urologia Nefrol (Mosk), Jul.-Aug. 1996, (4):41-47.
Yeung, Jeff. "Treating Urinary Stress Incontenance Without Incision with Endoscopic Suture Anchor & Approximating Device," Aleeva Medical, Inc., 2007.
Extended European Search Report dated Jan. 20, 2020 in EP Patent Application No. 19199026.6.

* cited by examiner

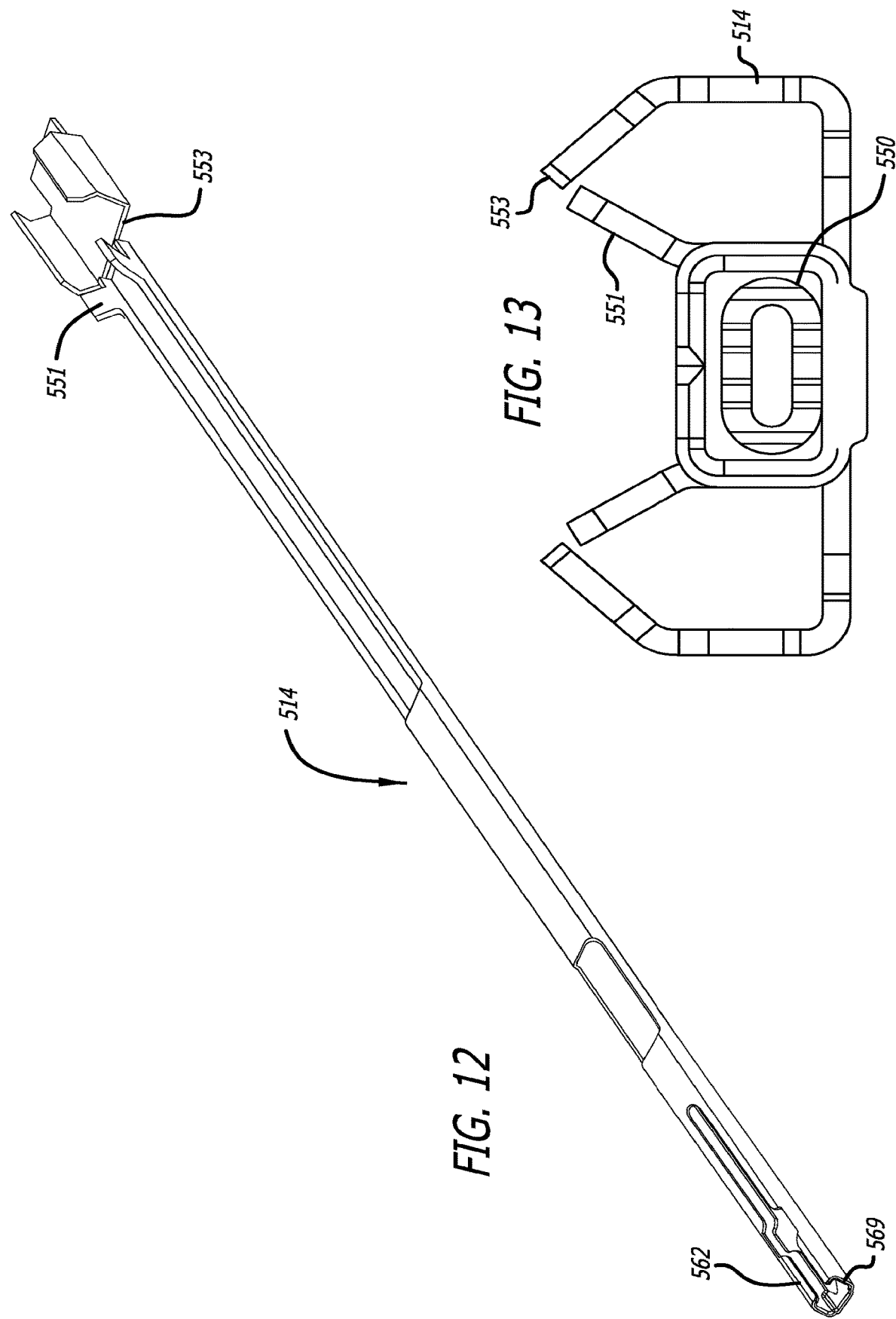

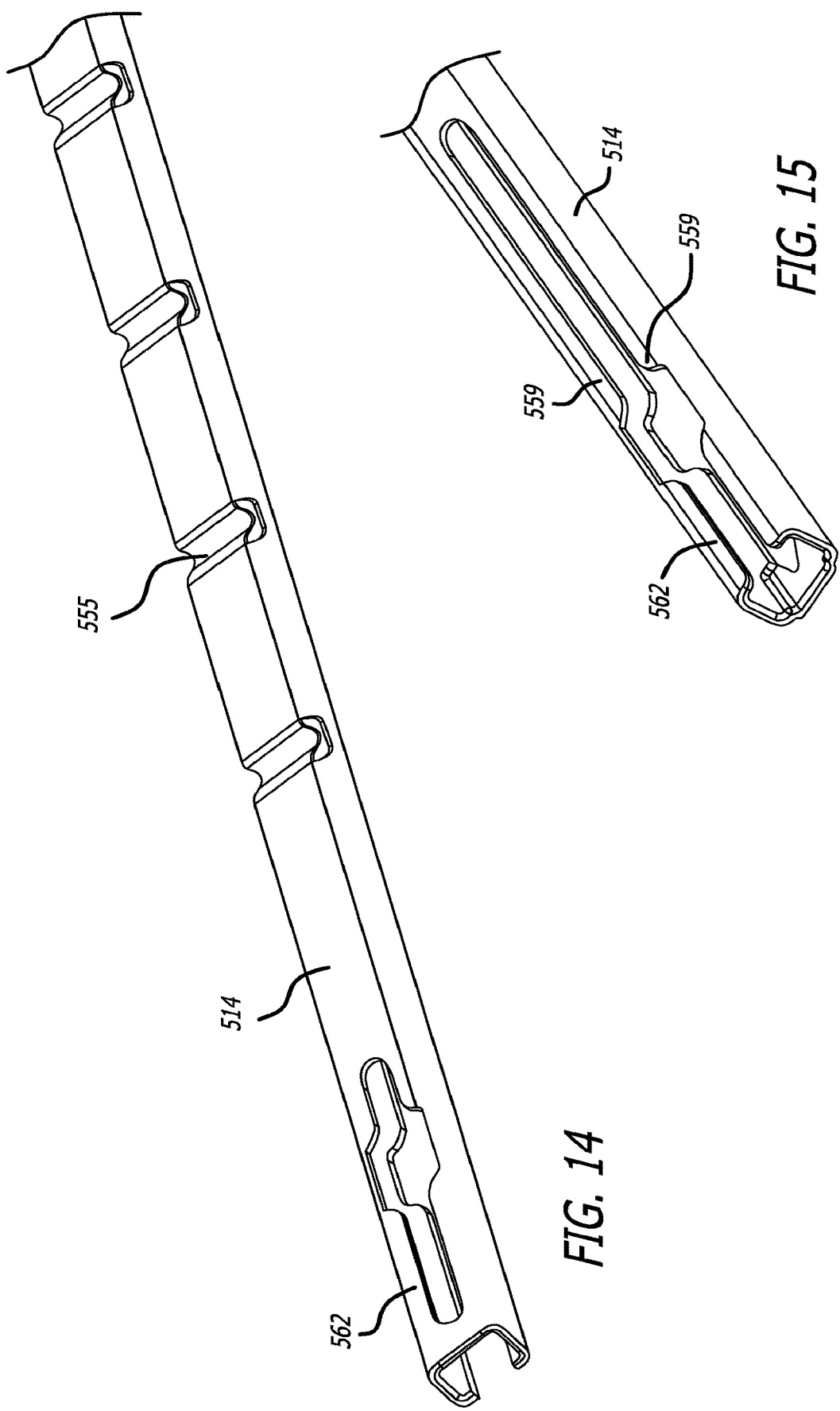

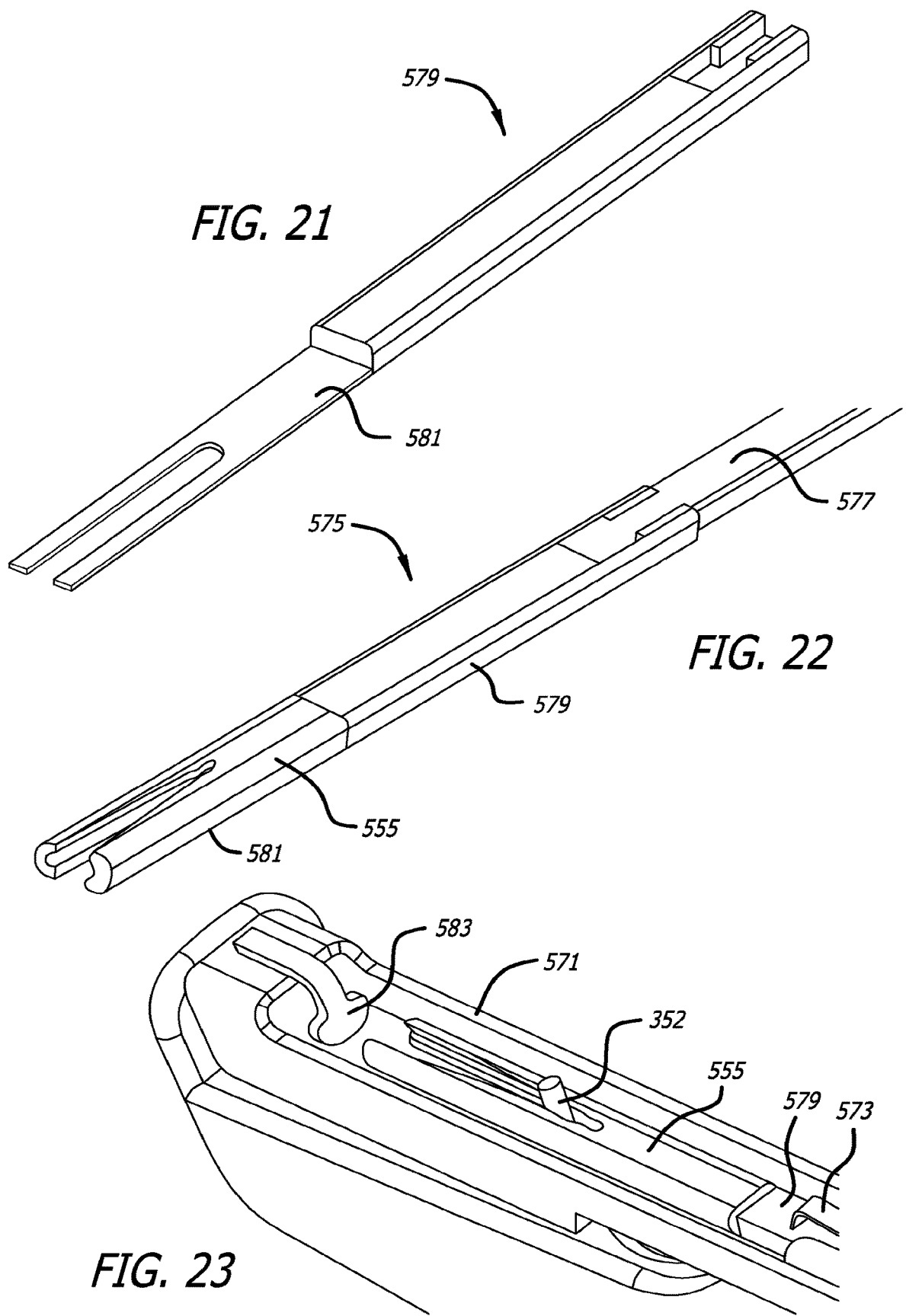

ANCHOR DELIVERY SYSTEM

CROSS-REFERENCE TO RELATED APPLICATIONS

This application is a continuation of U.S. patent application Ser. No. 15/295,395 filed Oct. 17, 2016, now U.S. Pat. No. 10,349,932, which is a divisional of copending U.S. patent application Ser. No. 13/833,299 filed Mar. 15, 2013, now U.S. Pat. No. 9,504,461, titled "Anchor Delivery System," the entire disclosures of which are expressly incorporated herein by reference.

BACKGROUND OF THE DISCLOSURE

The present disclosure relates generally to medical devices and methods, and more particularly to systems and associated methods for manipulating or retracting tissues and anatomical or other structures within the body of human or animal subjects for the purpose of treating diseases or disorders.

One example of a condition where it is desirable to lift, compress or otherwise remove a pathologically enlarged tissue is Benign Prostatic Hyperplasia (BPH). BPH is one of the most common medical conditions that affect men, especially elderly men. It has been reported that, in the United States, more than half of all men have histopathologic evidence of BPH by age 60 and, by age 85, approximately 9 out of 10 men suffer from the condition. Moreover, the incidence and prevalence of BPH are expected to increase as the average age of the population in developed countries increases.

The prostate gland enlarges throughout a man's life. In some men, the prostatic capsule around the prostate gland may prevent the prostate gland from enlarging further. This causes the inner end of the prostate gland to squeeze the urethra. This pressure on the urethra increases resistance to urine flow through the end of the urethra enclosed by the prostate. Thus the urinary bladder has to exert more pressure to force urine through the increased resistance of the urethra. Chronic over-exertion causes the muscular walls of the urinary bladder to remodel and become stiffer. This combination of increased urethral resistance to urine flow and stiffness and hypertrophy of urinary bladder walls leads to a variety of lower urinary tract symptoms (LUTS) that may severely reduce the patient's quality of life. These symptoms include weak or intermittent urine flow while urinating, straining when urinating, hesitation before urine flow starts, feeling that the bladder has not emptied completely even after urination, dribbling at the end of urination or leakage afterward, increased frequency of urination particularly at night, urgent need to urinate etc.

In addition to patients with BPH, LUTS may also be present in patients with prostate cancer, prostate infections, and chronic use of certain medications (e.g. ephedrine, pseudoephedrine, phenylpropanolamine, antihistamines such as diphenhydramine, chlorpheniramine etc.) that cause urinary retention especially in men with prostate enlargement.

Although BPH is rarely life threatening, it can lead to numerous clinical conditions including urinary retention, renal insufficiency, recurrent urinary tract infection, incontinence, hematuria, and bladder stones.

In developed countries, a large percentage of the patient population undergoes treatment for BPH symptoms. It has been estimated that by the age of 80 years, approximately 25% of the male population of the United States will have undergone some form of BPH treatment. At present, the available treatment options for BPH include watchful waiting, medications (phytotherapy and prescription medications), surgery and minimally invasive procedures.

For patients who choose the watchful waiting option, no immediate treatment is provided to the patient, but the patient undergoes regular exams to monitor progression of the disease. This is usually done on patients that have minimal symptoms that are not especially bothersome.

Surgical procedures for treating BPH symptoms include Transurethal Resection of Prostate (TURP), Transurethral Electrovaporization of Prostate (TVP), Transurethral Incision of the Prostate (TUIP), Laser Prostatectomy and Open Prostatectomy.

Minimally invasive procedures for treating BPH symptoms include Transurethral Microwave Thermotherapy (TUMT), Transurethral Needle Ablation (TUNA), Interstitial Laser Coagulation (ILC), and Prostatic Stents.

The most effective current methods of treating BPH carry a high risk of adverse effects. These methods and devices either require general or spinal anesthesia or have potential adverse effects that dictate that the procedures be performed in a surgical operating room, followed by a hospital stay for the patient. The methods of treating BPH that carry lower risks of adverse effects are also associated with a lower reduction in the symptom score. While several of these procedures can be conducted with local analgesia in an office setting, the patient does not experience immediate relief and in fact often experiences worse symptoms for weeks after the procedure until the body begins to heal. Additionally all device approaches require a urethral catheter placed in the bladder, in some cases for weeks. In some cases catheterization is indicated because the therapy actually causes obstruction during a period of time post operatively, and in other cases it is indicated because of post-operative bleeding and potentially occlusive clot formation. While drug therapies are easy to administer, the results are suboptimal, take significant time to take effect, and often entail undesired side effects.

There have been advances in developing minimally invasive devices and methods for lifting and repositioning of tissues. However, further advances are necessary to ensure an ability to access difficult to reach body structure.

There remains a need for the development of new devices and methods that can be used to deploy multiple anchors from a single delivery device to improve the user experience and minimizing patient discomfort. An ability to access anatomy with minimally invasive instruments while viewing the interventional procedure is also desirable. Moreover, various structures ensuring an effective interventional procedure such as implants having structural memory characteristics have been found to be helpful in certain treatment approaches.

The present disclosure addresses these and other needs.

SUMMARY

Briefly and in general terms, the present disclosure is directed towards an apparatus and method for deploying an anchor assembly within a patient's body to accomplish interventional treatments. A delivery device is provided to access the anatomy targeted for the interventional procedure. Some embodiments of the delivery device include mechanisms configured to deploy one or more anchor assemblies without removing the device from the interventional site.

The delivery apparatus of the present disclosure includes various subassemblies that are mobilized via an actuator or other manually accessible structure. The operation of the subassemblies is coordinated and synchronized to ensure accurate and precise implantation of an anchor assembly. In one embodiment, the delivery device is embodied in a tissue approximation assembly that is configured to treat BPH.

In one particular aspect, the present invention is directed towards a delivery device that accomplishes the delivery of a first or distal anchor assembly component at a first location within a patient's body and the delivery of a second or proximal anchor assembly component at a second location within the patient. Further, the delivery device can include mechanisms for efficient reloading of anchor assembles to minimize patient discomfort and enhance ease of use. The device can also accomplish imparting tension during delivery to a connector to hold it while attaching the proximal anchor in situ. The procedure can be viewed employing a scope inserted in the device. The scope can assume various configurations and can be employed with complementary structure assisting in the viewing function. Also, the delivery device can be sized and shaped to be compatible inside a sheath up to 24 F, preferably a 19 F or 20 F sheath or smaller.

The anchor assembly can be configured to accomplish approximating, retracting, lifting, compressing, supporting, remodeling, or repositioning tissue within the body of a human or animal subject. Moreover, the apparatus configured to deploy the anchor assembly as well as the anchor assembly itself are configured to complement and cooperate with body anatomy.

In one aspect, a system for treating a prostate includes a cartridge, a handle configured to receive the cartridge, and a delivery assembly. The cartridge includes a distal anchor, a connector, and a proximal anchor and the handle includes an actuator, a spring mechanism loaded with mechanical energy. The delivery assembly includes a member that mates with the cartridge to transfer the mechanical energy from the spring mechanism to the cartridge and the actuator operates to reload the mechanical energy.

In one aspect, a system for deploying an anchor assembly includes a cartridge carrying the anchor assembly and a handle configured to couple with the cartridge such that mechanical energy loaded in at least one spring mechanism within the handle is transferred to the cartridge to deploy the anchor assembly. The system includes an actuator configured to initiate transfer of the mechanical energy and restore the majority of the mechanical energy to the spring mechanisms.

In one aspect, a method for delivering a plurality of anchor assemblies includes inserting a cartridge into a handle assembly. The handle assembly includes an actuator and a drive mechanism having a first loaded configuration characterized by a total stored energy and an unloaded configuration. The cartridge includes at least one anchor assembly and a penetrating member. At least one anchor assembly and the penetrating member are configured to advance from a distal portion of the cartridge. The method includes positioning the distal portion of the cartridge at an interventional site adjacent a prostate and operating the actuator to cycle the drive mechanism from the loaded configuration to the unloaded configuration to a second loaded configuration characterized by a total stored energy. Operating the actuator simultaneously delivers at least one anchor assembly to the prostate by transferring load from the drive mechanism to the cartridge. The method includes removing the cartridge.

Various alternative methods of use are contemplated. The disclosed apparatus can be used to improve flow of a body fluid through a body lumen, modify the size or shape of a body lumen or cavity, treat prostate enlargement, treat urinary incontinence, support or maintain positioning of a tissue, close a tissue wound, organ or graft, perform a cosmetic lifting or repositioning procedure, form anastomotic connections, and/or treat various other disorders where a natural or pathologic tissue or organ is pressing on or interfering with an adjacent anatomical structure. Also, the invention has myriad other potential surgical, therapeutic, cosmetic or reconstructive applications, such as where a tissue, organ, graft or other material requires approximately, retracting, lifting, repositioning, compression or support.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIGS. 10-12 are perspective views depicting features of one embodiment of a cutter assembly of the delivery device.

FIG. 13 is a cross-sectional view depicting positioning of an anchor within the cutter assembly.

FIGS. 14-18 are various views depicting further features of a cutter assembly.

FIGS. 21-23 are perspective views depicting features of a pusher assembly.

DETAILED DESCRIPTION OF THE PREFERRED EMBODIMENTS

Turning now to the figures, which are provided by way of example and not limitation, the present disclosure is directed to a device configured to deliver multiple anchor assemblies within a patient's body for treatment purposes. The disclosed apparatus can be employed for various medical purposes including but not limited to retracting, lifting, compressing, approximating, supporting, remodeling, or repositioning tissues, organs, anatomical structures, grafts or other material found within a patient's body. Such tissue manipulation is intended to facilitate the treatment of diseases or disorders such as the displacement, compression and/or retraction of the body tissue.

In an aspect of the present disclosure, the delivery device includes a handle assembly supporting an elongate member. The elongate member defines a low profile that is suited to navigate body anatomy to reach an interventional site. Substructure is provided to maintain a longitudinal profile of the elongate member so that the interventional procedure can progress as intended.

In another aspect, one portion of an anchor assembly or implant is positioned and implanted against a first section of anatomy. A second portion of the anchor assembly or implant is then positioned and implanted adjacent to a second section of anatomy for the purpose of retracting, lifting, compressing, approximating, supporting, remodeling, or repositioning the second section of anatomy with respect to the first section of anatomy as well as for the purpose of retracting, lifting, compressing, approximating, supporting, remodeling, or repositioning the first section of anatomy with respect to the second section of anatomy. It is also to be recognized that both a first and second portion of the anchor assembly can be configured to accomplish the desired retracting, lifting, compressing, approximating, supporting, remodeling, or repositioning of anatomy due to tension supplied during delivery via a connector assembly affixed to the first and second portions of the anchor assembly or implant. The delivery device can include an endoscope providing the ability to view the interventional procedure.

Figure 1A:
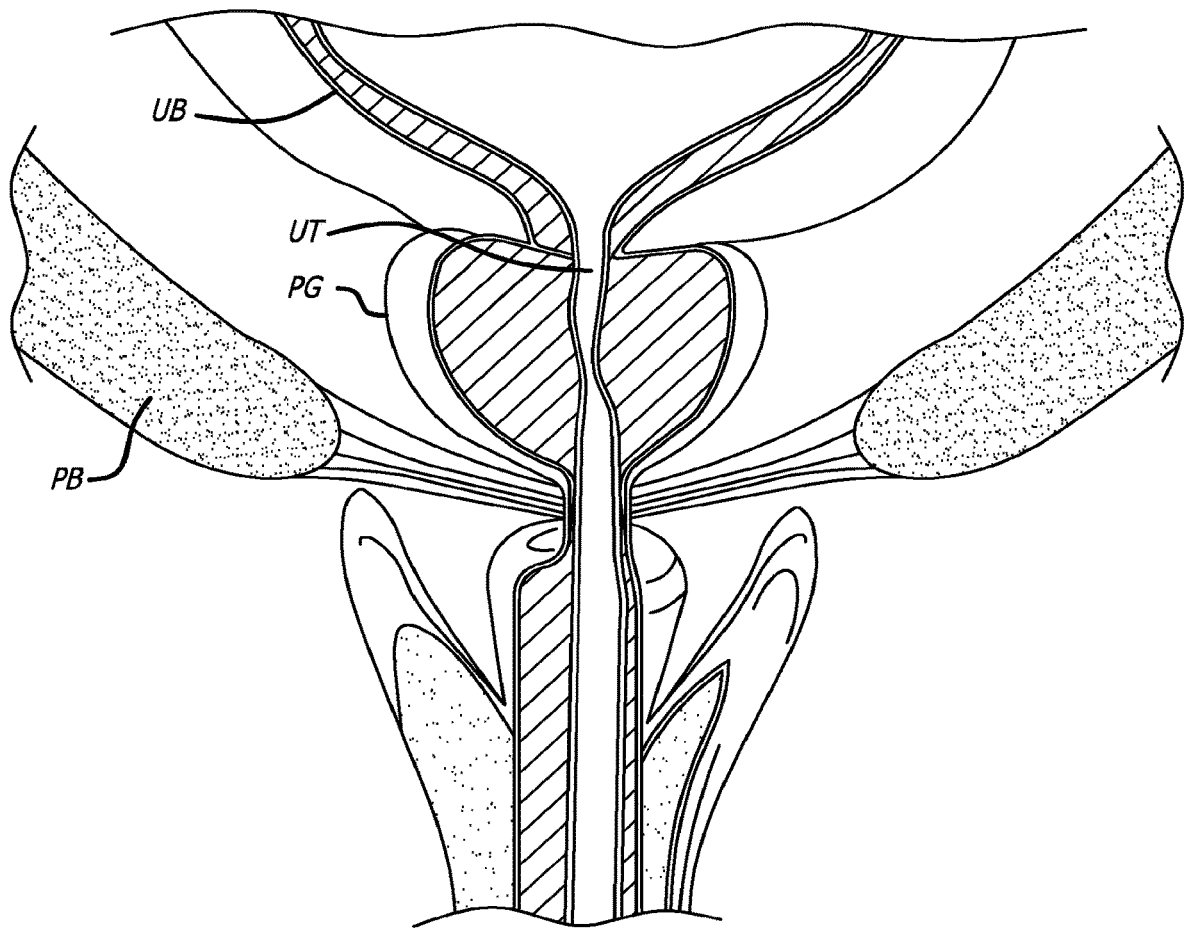
FIG. 1A shows a coronal section through the lower abdomen of a male human suffering from BPH showing a hypertrophied prostate gland.

FIG. 1A shows a coronal section (i.e., a section cut approximately in the plane of the coronal suture or parallel to it) through the lower abdomen of a male human suffering from BPH showing a hypertrophied prostate gland. As depicted in FIG. 1A, the urinary bladder UB is a hollow muscular organ that temporarily stores urine. It is situated behind the pubic bone PB. The lower region of the urinary bladder has a narrow muscular opening called the bladder neck which opens into a soft, flexible, tubular organ called the urethra UT. The muscles around the bladder neck are called the internal urethral sphincter. The internal urethral sphincter is normally contracted to prevent urine leakage. The urinary bladder gradually fills with urine until full capacity is reached, at which point the sphincters relax. This causes the bladder neck to open, thereby releasing the urine stored in the urinary bladder into the urethra. The urethra conducts urine from the urinary bladder to the exterior of the body. The urethra begins at the bladder neck and terminates at the end of the penis. The prostate gland PG is located around the urethra at the union of the urethra and the urinary bladder. In FIG. 1A, the prostate gland is hypertrophied (enlarged). This causes the prostate gland to press on a region of the urethra. This in turn creates an undesired obstruction to the flow of urine through the urethra.

Figure 1B:
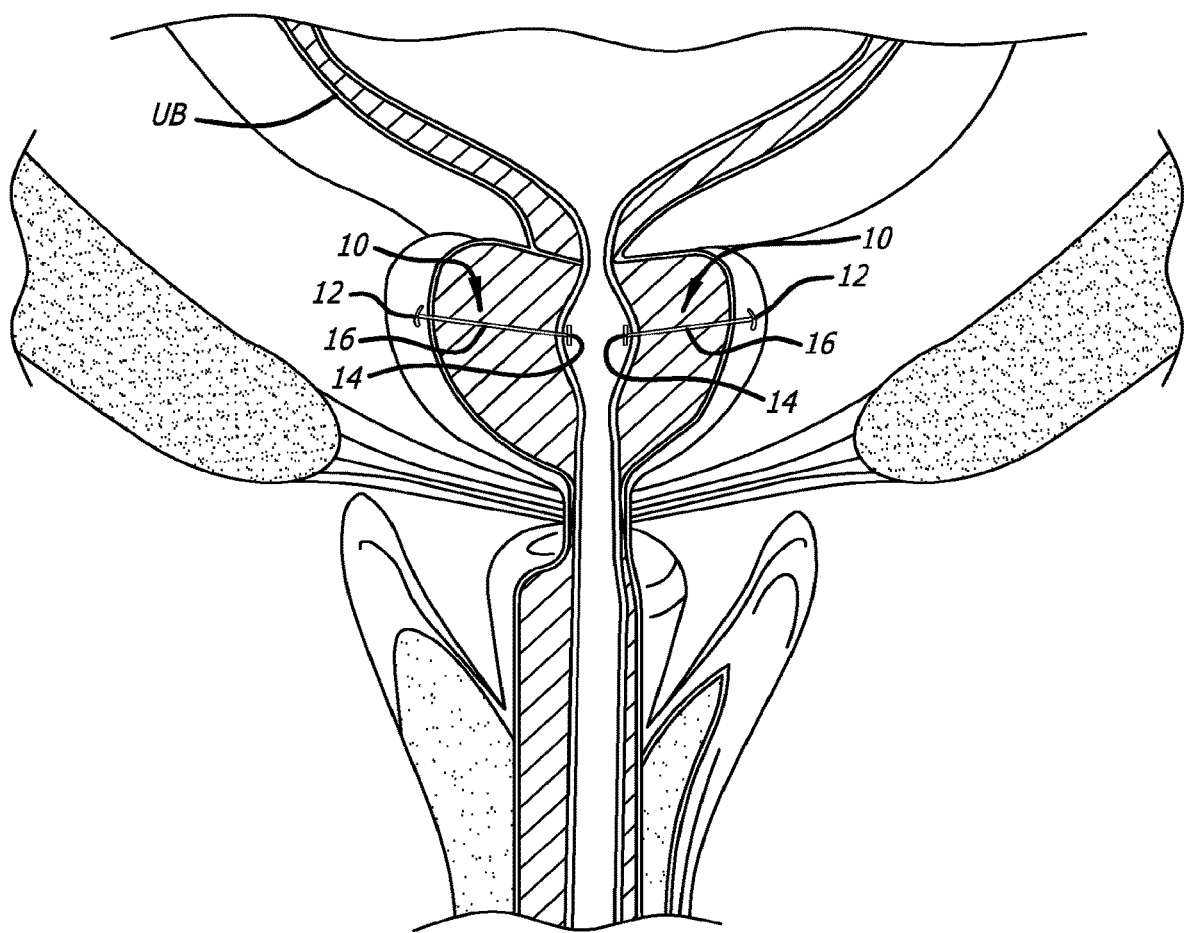
FIG. 1B shows a coronal section through the lower abdomen of a male human suffering from BPH showing a hypertrophied prostate gland treated with an embodiment of the device of the present invention.

FIG. 1B shows a coronal section through the lower abdomen of a male human suffering from BPH showing a hypertrophied prostate gland treated with an embodiment of the device of the present invention. It has been discovered that the enlarged prostate gland is compressible and can be retracted so as to relieve the pressure from the urethra. In accordance with one embodiment of the present invention, a retaining device can be placed through the prostate gland in order to relieve the pressure on the urethra. In FIG. 1B, a retainer 10 is implanted in the prostate gland. Retainer 10 comprises a distal anchor 12 and a proximal anchor 14. Distal anchor 12 and a proximal anchor 14 are connected by a connector 16. The radial distance from the urethra to distal anchor 12 is greater than the radial distance from the urethra to proximal anchor 14. The distance or tension between the anchors is sufficient to compress, displace or change the orientation of an anatomical region between distal anchor 12 and proximal anchor 14. The connector 16 can be inelastic so as to maintain a constant force or distance between the proximal and distal anchors or be elastic so as to attempt to draw the proximal and distal anchors closer together. In the embodiment shown in FIG. 1B, distal anchor 12 is located on the outer surface of the capsule of prostate gland CP and acts as a capsular anchor. Alternatively, distal anchor 12 may be embedded inside the tissue of prostate gland PG or in the surrounding structures around the prostate such as periosteum of the pelvic bones, within the bones themselves, pelvic fascia, coopers ligament, muscles traversing the pelvis or bladder wall. Also, in the embodiment shown in FIG. 1B, proximal anchor 14 is located on the inner wall of urethra UT and acts as a urethral anchor. Alternatively, proximal anchor 14 may be embedded inside the tissue of prostate gland PG or surrounding structures as outlined above. Distal anchor 12 and proximal anchor 14 are implanted in the anatomy such that a desired distance or tension is created in connector 16. This causes distal anchor 12 and proximal anchor 14 to retract or compress a region of prostate gland PG to relieve the obstruction shown in FIG. 1A. In FIG. 1B, two retainers 10 are implanted in prostate gland PG. Each retainer 10 is implanted in a lateral lobe (side lobe) of prostate gland PG. The various methods and devices disclosed herein may be used to treat a single lobe or multiple lobes of the prostate gland or other anatomical structures. Similarly, two or more devices disclosed herein may be used to treat a single anatomical structure. For example, a lateral lobe of prostate gland PG may be treated using two retainers 10. One or more retainers may be deployed at particular angles to the axis of the urethra to target one or more lateral lobes and/or middle lobe of the prostate gland. In one embodiment, retainer 10 is deployed between the 1 o'clock and 3 o'clock position relative to the axis of the urethra to target the left lateral lobe of the prostate gland. In another embodiment, retainer 10 is deployed between the 9 o'clock and 11 o'clock position relative to the axis of the urethra to target the right lateral lobe of the prostate gland. In another embodiment, retainer 10 is deployed between the 4 o'clock and 8 o'clock position relative to the axis of the urethra to target the middle lobe of the prostate gland.

Figure 1C:
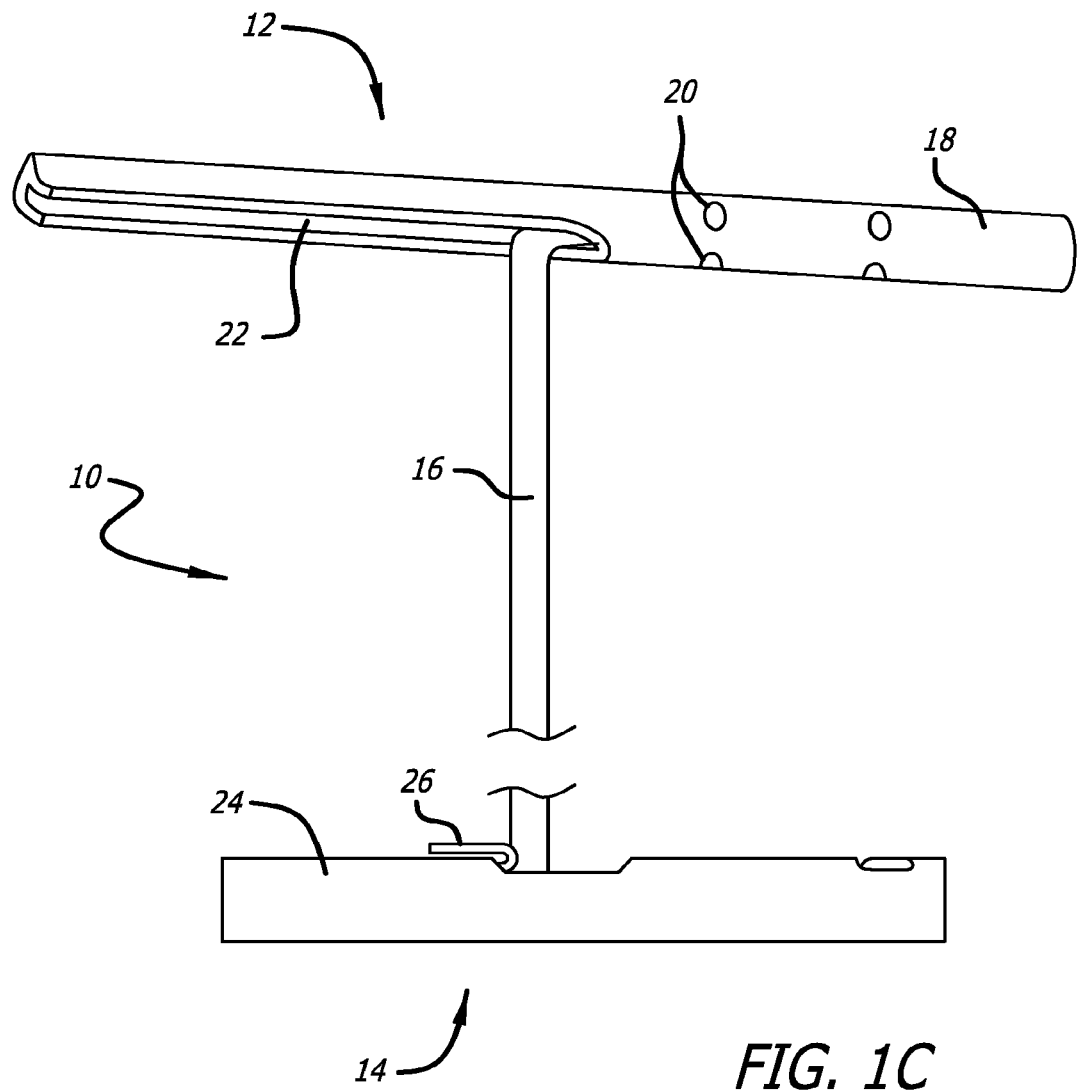
FIG. 1C shows a side view of an embodiment of the retainer shown in FIG. 1B.
Figure 1D:
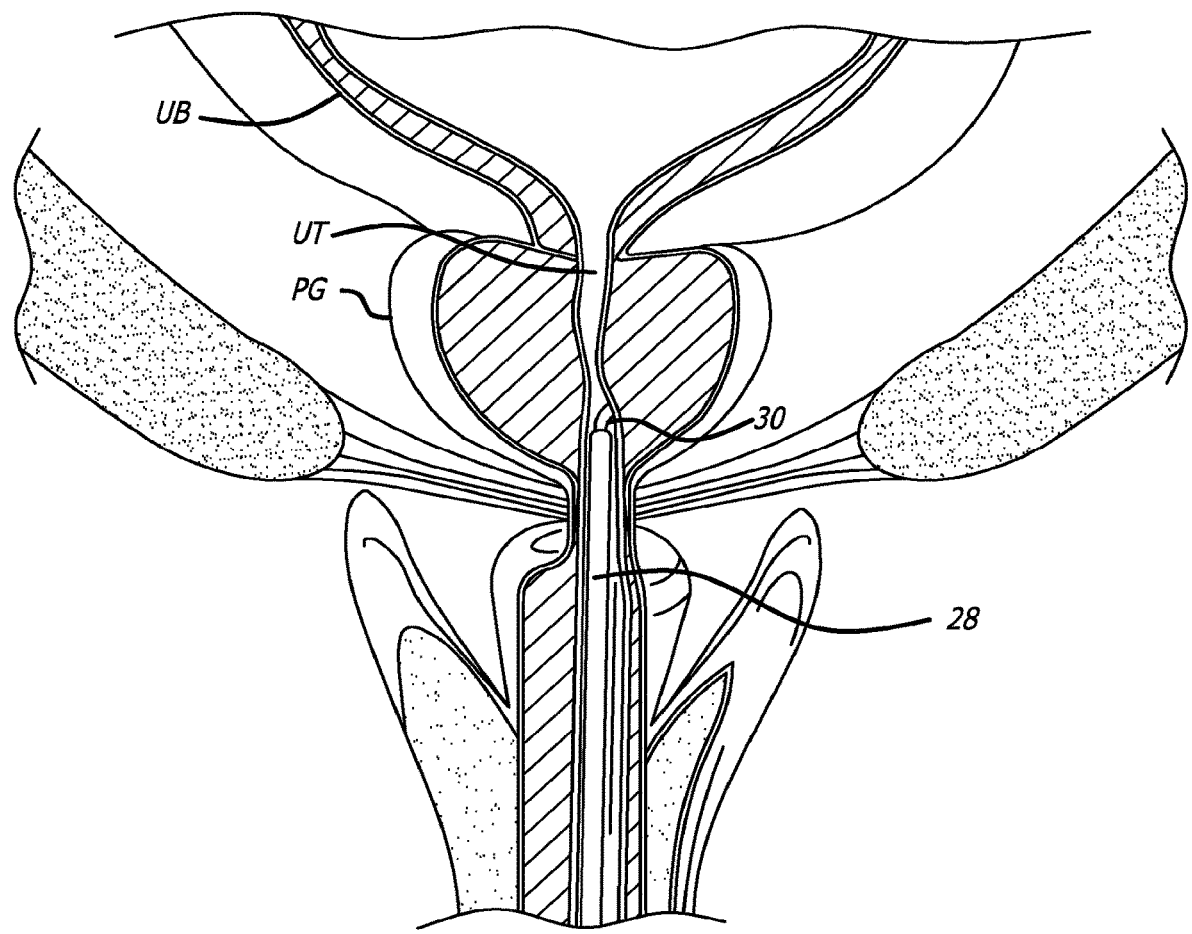
FIGS. 1D through 1J show the various steps of a method of treating a prostate gland by the retainer shown in FIG. 1C.

FIG. 1C shows a side view of one embodiment of the retainer shown in FIG. 1B. FIG. 1C shows retainer 10 comprising distal anchor 12 and proximal anchor 14. Distal anchor 12 and proximal anchor 14 are connected by connector 16. In the embodiment shown in FIG. 1C, distal anchor 12 comprises a tube 18 having a lumen. Tube 18 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, EPTFE, shape memory polymers, such as polyesterurethane, polyetherurethane, polyetherpolyesters, polyetherpolyamines or combinations of oligo e-caprolactore diol and oligo p-dioxanone diol polymers, etc. Connector 16 is attached to tube 18. In one embodiment, connector 16 is a USP size 0 polypropylene monofilament suture. In the embodiment shown in FIG. 1C, a distal region of connector 16 is located in the lumen of tube 18 such that the distal tip of connector 16 emerges out of one end of the lumen of tube 18. The distal tip of connector 16 is enlarged, such that the diameter of the enlarged distal tip of connector 16 is greater than the inner diameter of tube 18. In one embodiment, the diameter of connector 16 is 0.014 inches and the diameter of the enlarged distal tip of connector 16 is 0.025 inches. In one embodiment, the enlarged distal tip of connector 16 is created by controlled melting of the distal tip of connector 16. This attaches connector 16 to tube 18. Tube 18 may comprise one or more additional attachment mechanisms to attach a distal region of connector 16 to tube 18. In one embodiment, the distal region of connector 16 is attached to tube 18 by a suitable biocompatible adhesive. In the embodiment shown in FIG. 1C, the distal region of connector 16 is attached to tube 18 by one or more inwardly opening flaps 20 that are cut in the material of tube 18. Flaps 20 grip connector 16 and thus prevent the relative motion of connector 16 and tube 18. The angle between one of flaps 20 and connector 16 may range from 1 degree to 90 degrees. Tube 18 further comprises a longitudinal slot 22. Longitudinal slot 22 extends from one end to roughly the mid section of tube 18. Connector 16 emerges out of this longitudinal slot 22. Thus, when connector 16 is pulled in the proximal direction, distal anchor 12 assumes a T-shape that helps to anchor distal anchor 12 to an anatomical structure. Distal anchor 12 may comprise a sharp edge to help penetrate distal anchor 12 through the anatomy. In a preferred embodiment, distal anchor 12 is constructed by laser cutting and electropolishing a nickel-titanium alloy (e.g., nitinol) tube made of 50.8% nickel-49.2% titanium. In the preferred embodiment, the outer diameter of tube 18 is 0.026 inches, the inner diameter of tube 18 is 0.015 inches, the length of tube 18 is 0.315 inches and the length of longitudinal slot 22 is 0.170 inches.

In the embodiment shown in FIG. 1C, proximal anchor 14 comprises a tube 24 comprising a lumen. Tube 24 can be made of suitable elastic or non-elastic materials including, but not limited to metals, polymers, etc. Typical examples of such materials include, but are not limited to stainless steel 304, stainless steel 316, nickel-Titanium alloys, titanium, Pebax, Polyimide, braided Polyimide, Polyurethane, Nylon, PVC, Hytrel, HDPE, PEEK, PTFE, PFA, FEP, ePTFE, such as polyesterurethane, polyetherurethane, polyetherpolyesters, polyetherpolyamines or combinations of oligo e-caprolactone diol and oligo p-dioxanone diol polymers, etc. An outwardly opening flap 26 is cut through the material of tube 24. Flap 26 is folded on the outer surface of tube 18 as shown in FIG. 1C. This creates an opening to the lumen of tube 24 that is lined by the atraumatic edge of the folded flap 26. Connector 16 enters tube 24 through this opening to the lumen of tube 24. Proximal anchor 14 further comprises an attachment mechanism to attach connector 16 to tube 24. Connector 16 can be made of suitable elastic or non-elastic materials including, but not limited to metals, polymers, etc. Other proximal anchor and distal anchor concepts are within the scope of the invention, such as v-shaped proximal anchors that are press fit onto a connector. Typical examples of such materials include, but are not limited to stainless steel 304, stainless steel 316, nickel-Titanium alloys, suture materials, titanium, silicone, nylon, polyamide, polyglycolic acid, polypropylene, Pebax, PTFE, ePTFE, silk, gut, or any other braided or mono-filament material. In a preferred embodiment, tube 24 has a length of 0.236 inches and an outer diameter of 0.027 inches and an inner diameter of 0.020 inches. The length of opening to the lumen of tube 24 is approximately 0.055 inches. In the preferred embodiment, the attachment mechanism comprises a lock pin that frictionally attaches connector 16 to tube 24. The lock pin and tube 24 are made of stainless steel 316L. In the preferred embodiment, tube 24 is laser cut or stamped and then electropolished. Lock pin is constructed using EDM (electrical discharge machining) and then passivated.

FIGS. 1D through 1J show the various steps of a method of treating a prostate gland by the retainer shown in FIG. 1C. Similar methods may be also used to deploy retainer or compression devices in other anatomical structures. In the step shown in FIG. 1D, a sheath 28 such as a standard resectoscope sheath is introduced into the urethra (transurethrally). Sheath 28 is advanced through urethra UT such that the distal end of sheath 28 is positioned near a region of urethra UT that is obstructed by a hypertrophied prostate gland PG. Distal anchor delivery device 30 is introduced through sheath 28. Distal anchor delivery device 30 can be placed in the sheath 28 after the distal end of sheath 28 is positioned near the region of the urethra UT that is obstructed or the distal anchor delivery device 30 can be pre-loaded in the sheath 28 before positioning of the sheath 28. Distal anchor delivery device 30 is advanced through sheath 28 such that the distal end of distal anchor delivery device 30 emerges out of the distal end of sheath 28. Distal anchor delivery device 30 is oriented such that a working channel opening of distal anchor delivery device 30 points towards a lateral lobe of prostate gland PG.

Figure 1E:
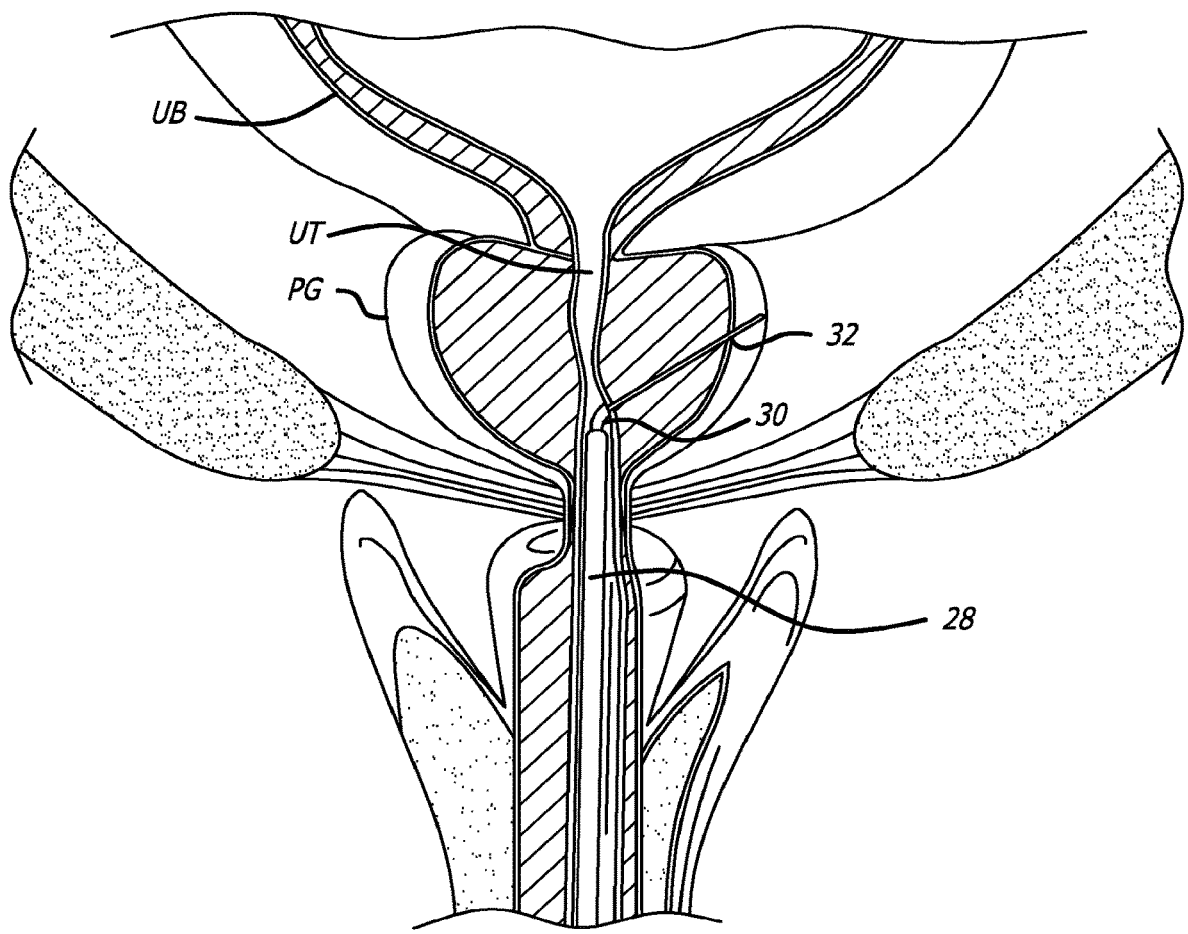

In the step shown in FIG. 1E, a needle 32 is introduced through distal anchor delivery device 30. Needle 32 can be placed in distal anchor delivery device after the distal anchor delivery device 30 is advanced through sheath 28 or the needle 32 can be pre-loaded in the distal anchor delivery device 30. In one embodiment, needle 32 is a 20 gauge needle. Needle 32 is advanced through distal anchor delivery device 30 such that it emerges through the working channel opening. Needle 32 is further advanced such that it penetrates through the tissue of prostate gland PG and the distal end of needle 32 emerges out of the capsule of prostate gland CP.

Figure 1F:
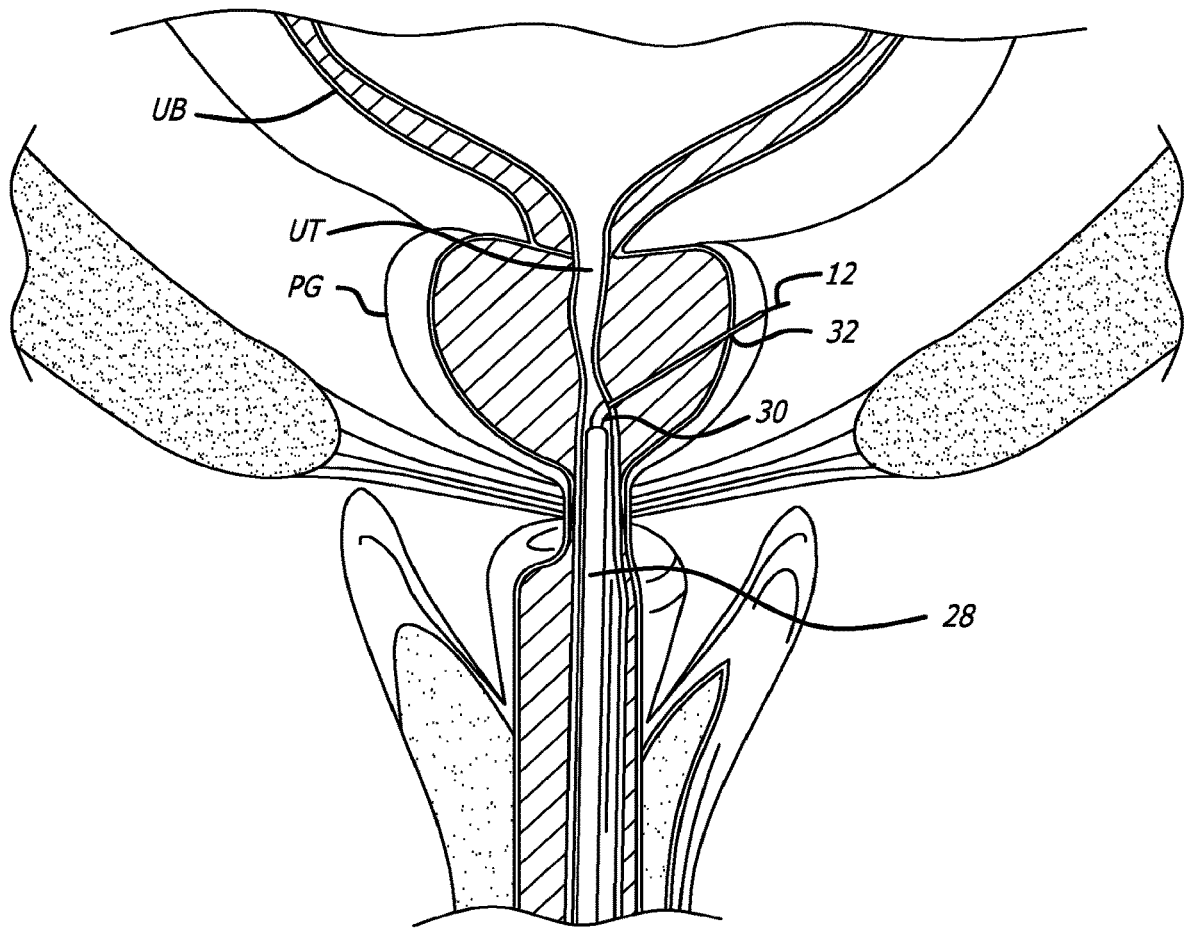

In the step shown in FIG. 1F, distal anchor 12 connected to connector 16 is advanced through needle 32. Distal anchor 12 can be pre-loaded in needle 32 or can be loaded in needle 32 after needle 32 has been advanced through distal anchor delivery device 30. Distal anchor 12 is advanced through needle 32 such that it emerges out of the distal end of needle 32. In alternate embodiments, the distal anchor can be held in place by a pusher or connector while the needle is retracted, thus exposing the distal anchor.

Figure 1G:
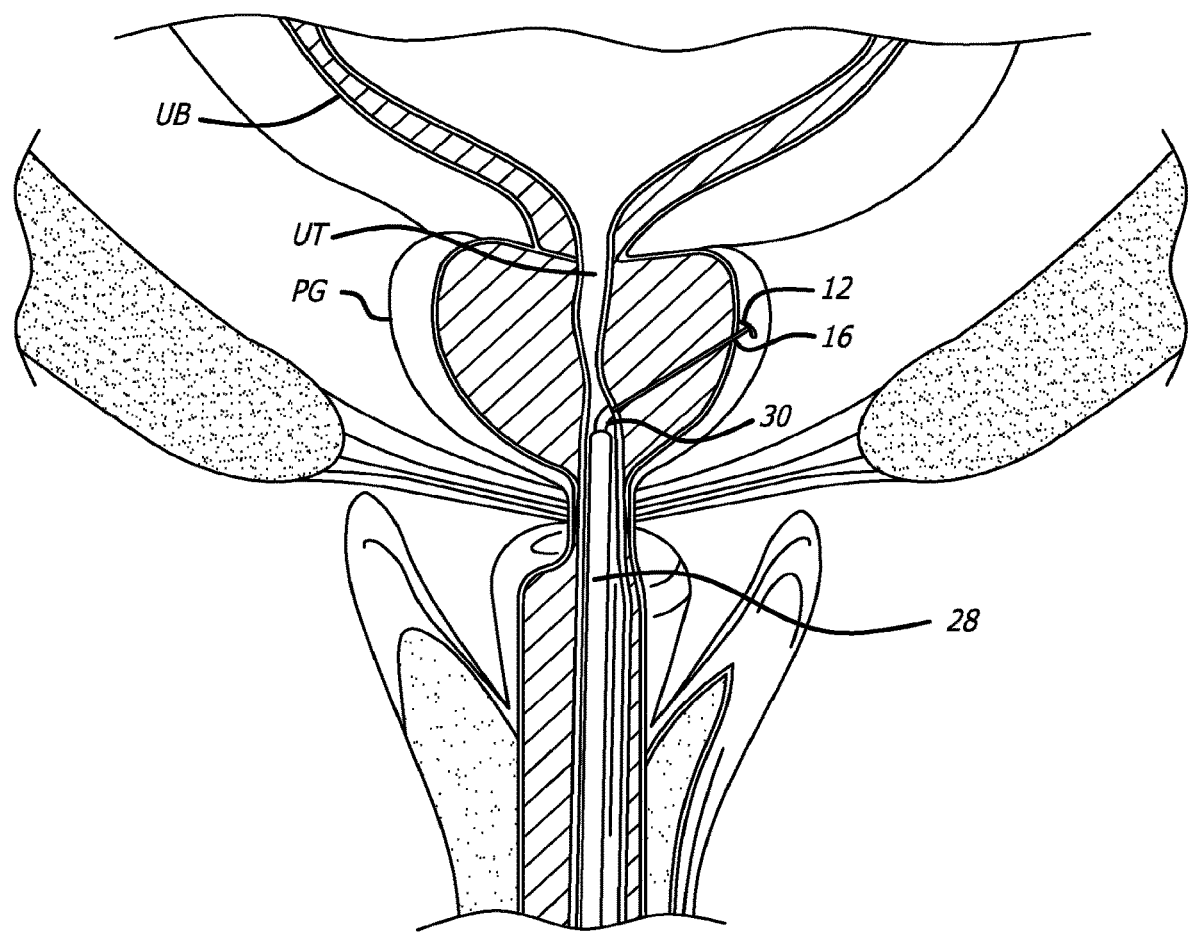

In the step shown in FIG. 1G, needle 32 is removed from distal anchor delivery device 30 by pulling needle 32 in the proximal direction.

Figure 1H:
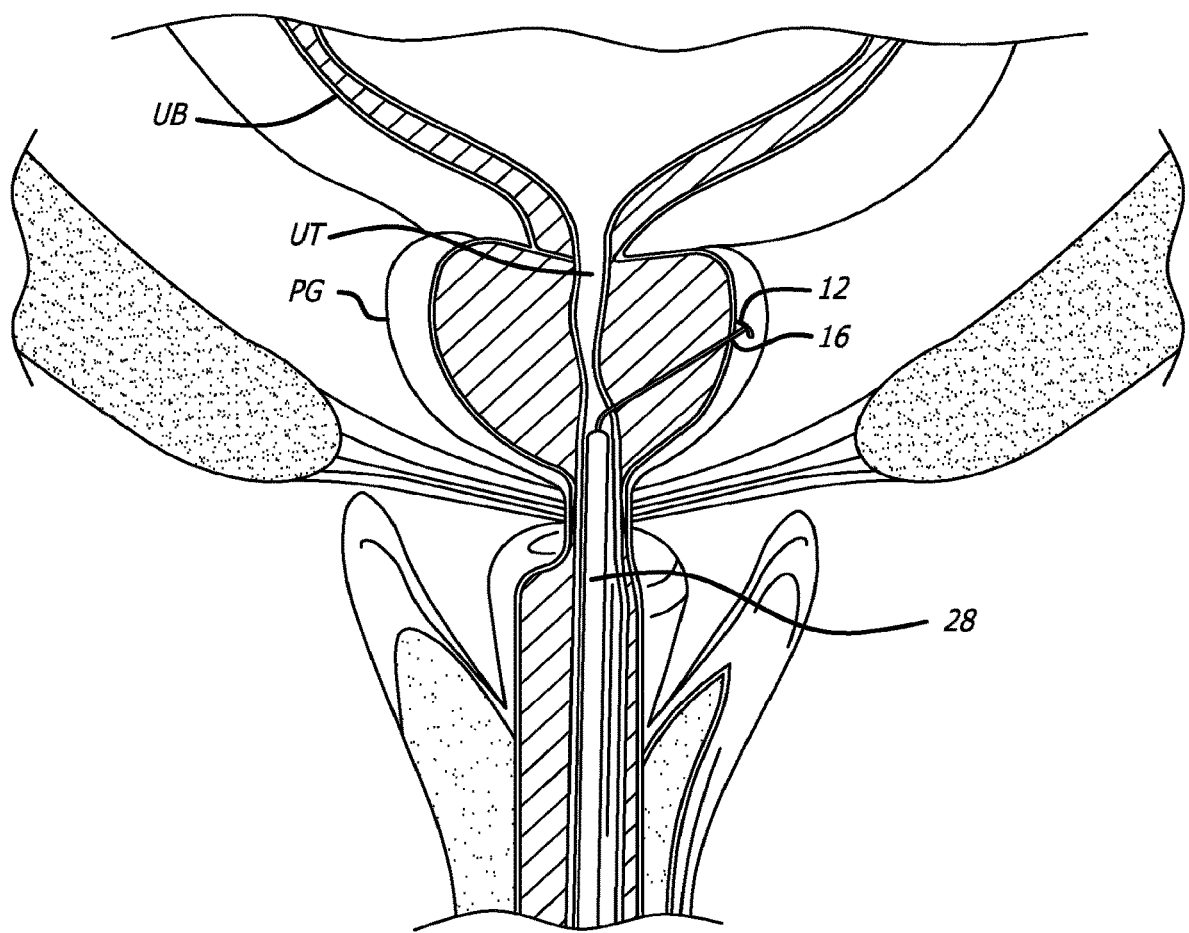

In the step shown in FIG. 1H, distal anchor delivery device 30 is removed from sheath 28 by pulling distal anchor delivery device 30 in the proximal direction. Also, connector 16 is pulled to orient distal anchor 12 perpendicularly to connector 16.

Figure 1I:
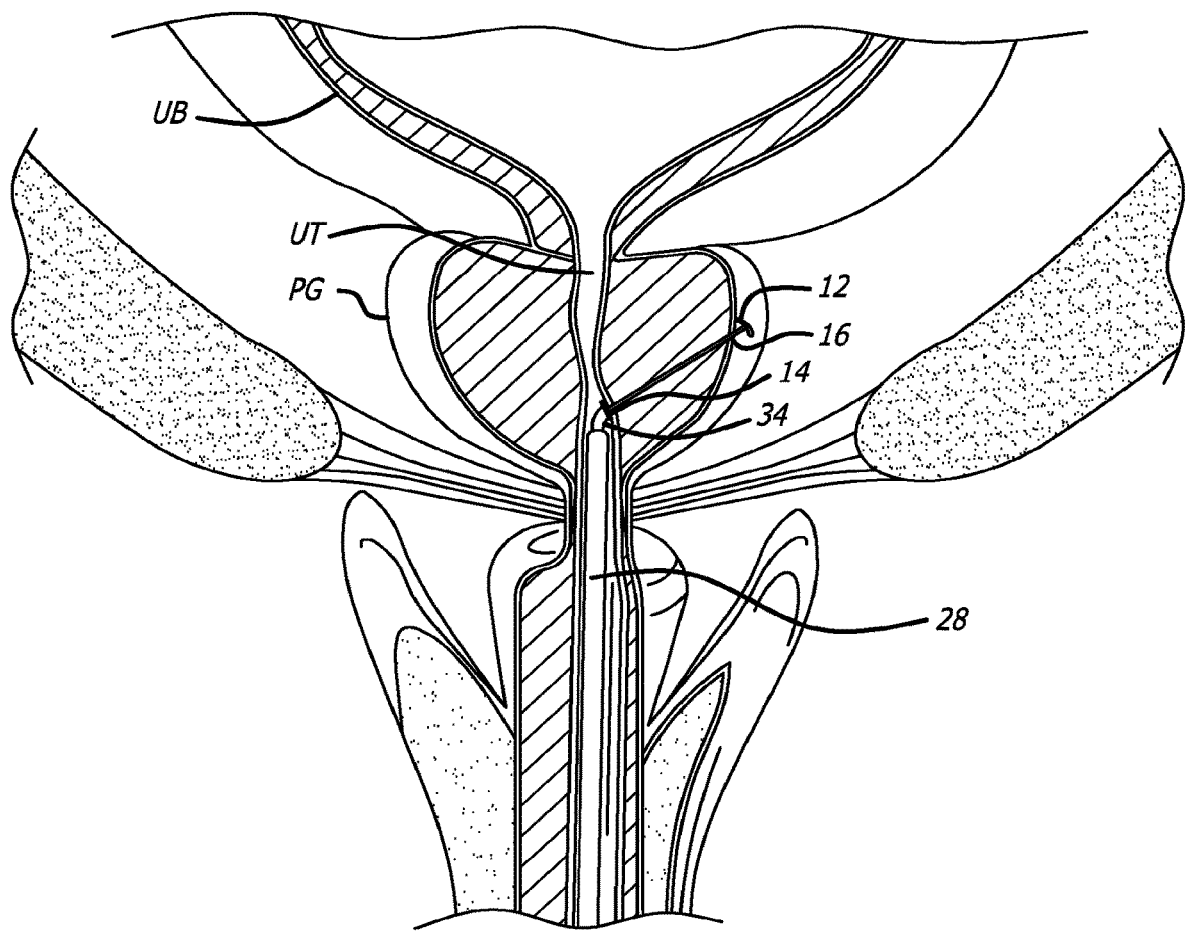

In the step shown in FIG. 1I, connector 16 is passed through proximal anchor 14 located on a proximal anchor delivery device 34. Proximal anchor delivery device 34 is advanced through sheath 28 such that the distal end of proximal anchor delivery device 34 emerges out of the distal end of sheath 28. A desired tension is introduced in connector 16 such that distal anchor 12 is pulled by connector 16 with a desired force. Alternatively, the proximal anchor can be visualized through an endoscope or under fluoroscopy and advanced along the connector until the desired retraction of the tissue is achieved. In other embodiments, the proximal anchor is a v-shaped or clothespin-shaped piece that is forced, in some cases at high speed, onto the connector to fixedly engage the connector.

Figure 1J:
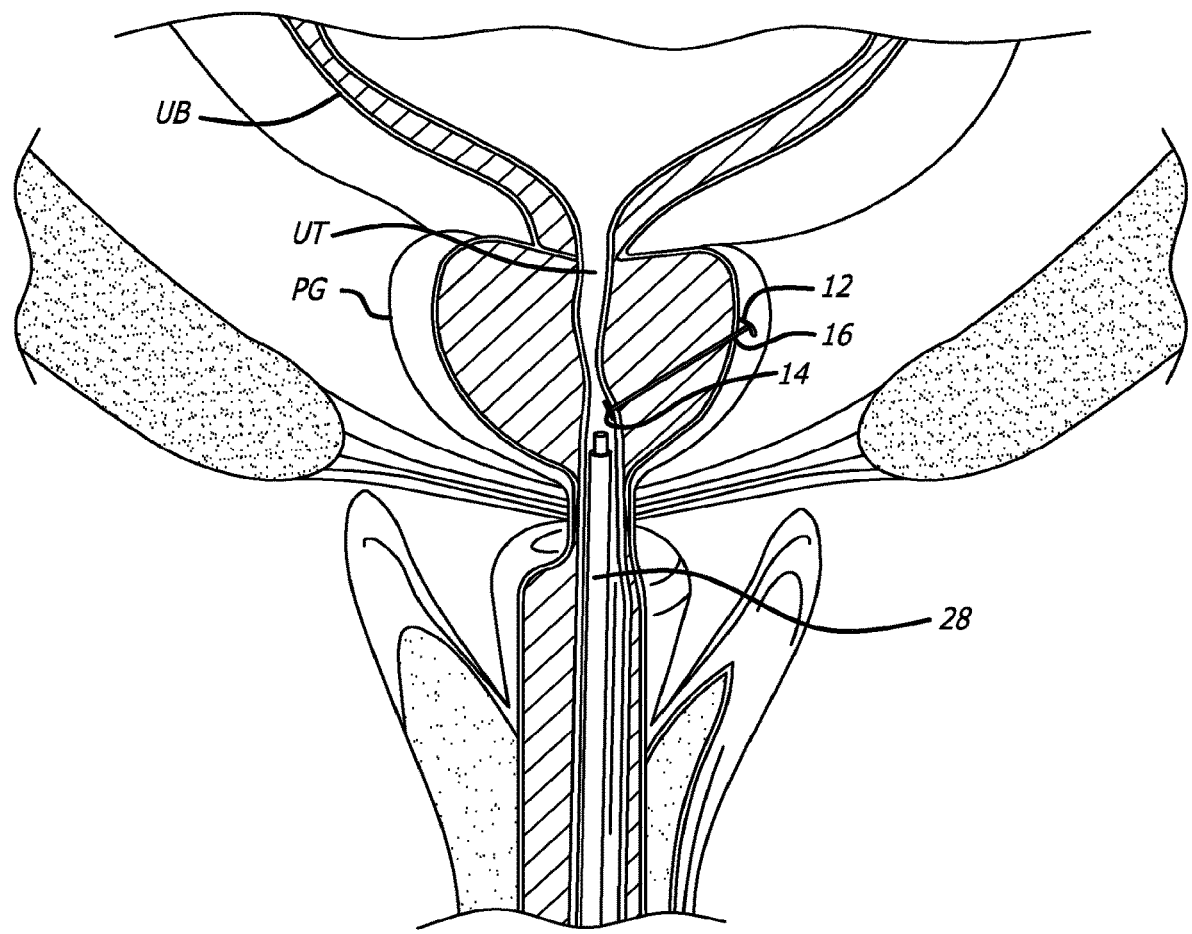

In the step shown in FIG. 1J, connector 16 is attached to proximal anchor 14. Proximal anchor 14 is also released from proximal anchor delivery device 34, thus deploying proximal anchor 14 in the anatomy. Proximal anchor delivery device 34 and sheath 28 are removed form the anatomy. Retainer 10 comprising distal anchor 12, proximal anchor 14 and connector 16 is used to retract, lift, support, reposition or compress a region of prostate gland PG located between distal anchor 12 and proximal anchor 14. This method may be used to retract, lift, support, reposition or compress multiple regions or lobes of the prostate gland PG. In the method shown in FIGS. 1D through 1J, distal anchor 12 is deployed on the outer surface of the capsule of prostate gland CP. Thus, distal anchor 12 acts as a capsular anchor. Alternatively, distal anchor 12 may be deployed inside the tissue of prostate gland PG or beyond the prostate as outlined previously. Similarly, in the method shown in FIGS. 1D through 1J, proximal anchor 14 is deployed on the inner wall of urethra UT and acts as a urethral anchor. Alternatively, proximal anchor 14 may be deployed inside the tissue of prostate gland PG.

The tissue approximation anchor shown in FIG. 1C is designed to be useable in a physician's clinical office environment (in contrast to requiring a hospital environment) with a delivery tool. The delivery tool is used through a 19 F or 20 F sheath in one preferred embodiment. Additionally, the material selection and construction of the tissue approximation anchor still allows for a subsequent TURP procedure to be performed, if necessary, on the prostate. In this suture-based, tissue approximation technique, a needle delivery mechanism is used to implant an anchor assembly.

Figure 2:
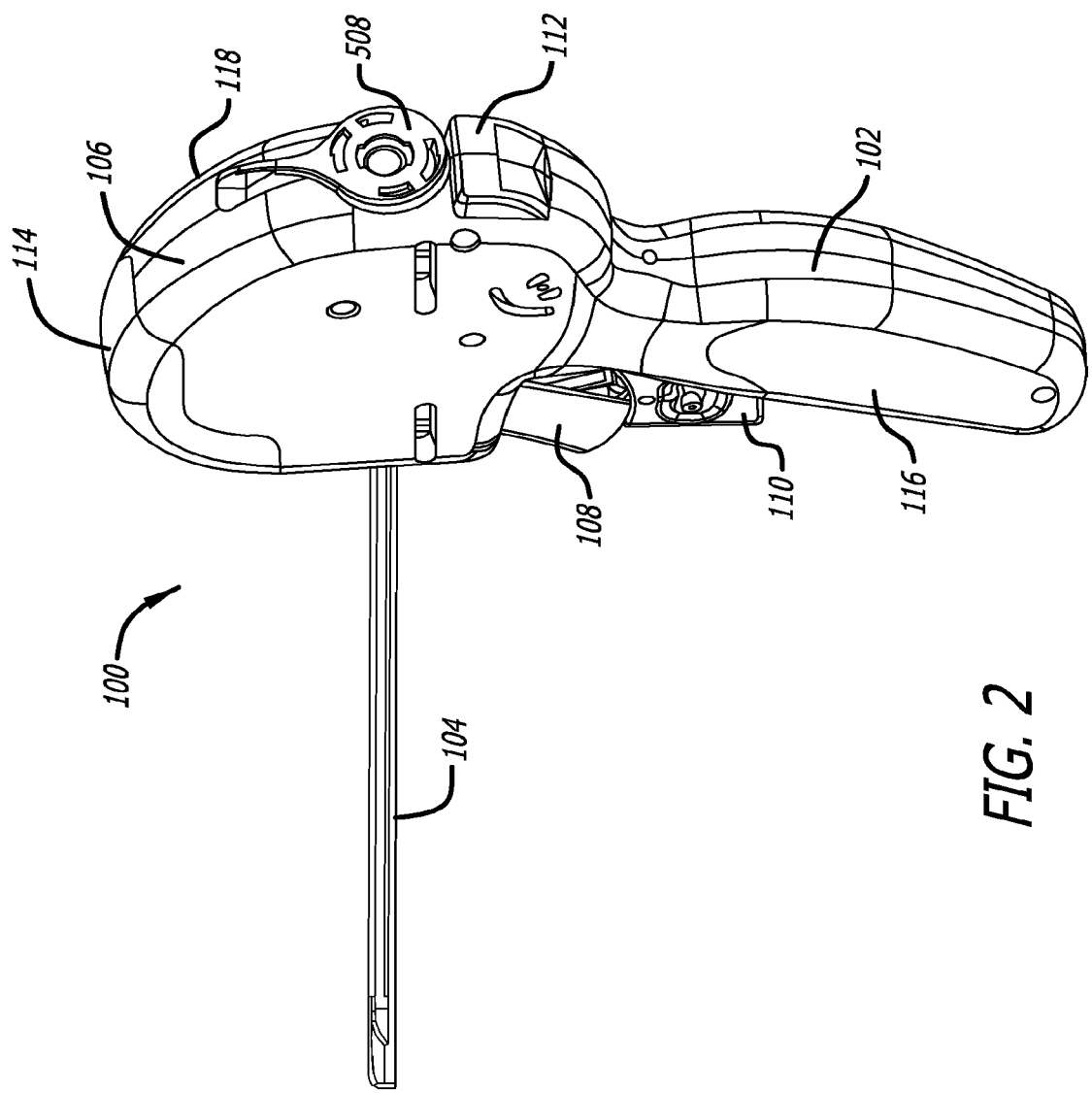
FIG. 2 is a perspective view depicting one embodiment of an anchor delivery system.
Figure 3:
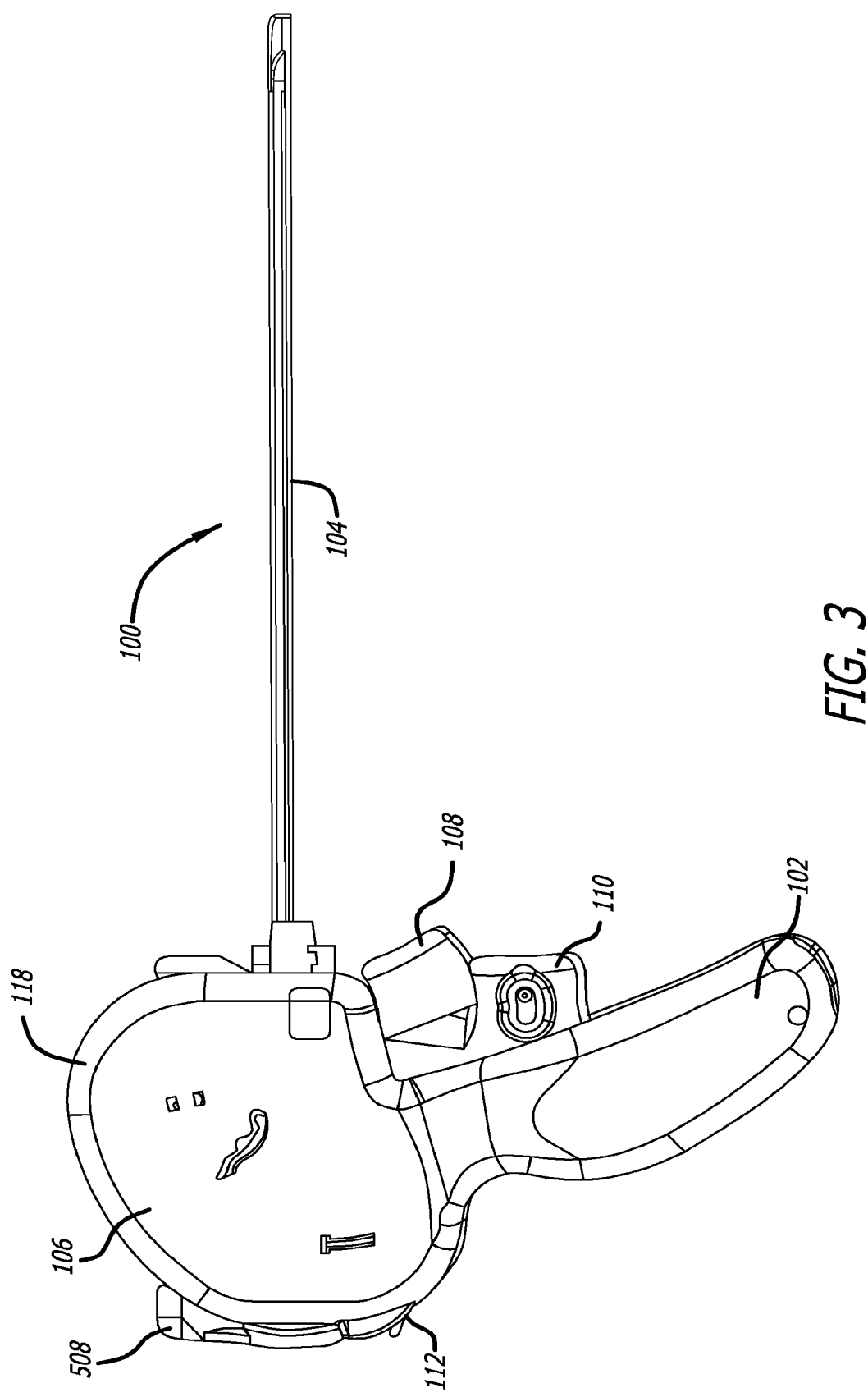
FIG. 3 is a right side view depicting the anchor delivery system of FIG. 2.
Figure 4:
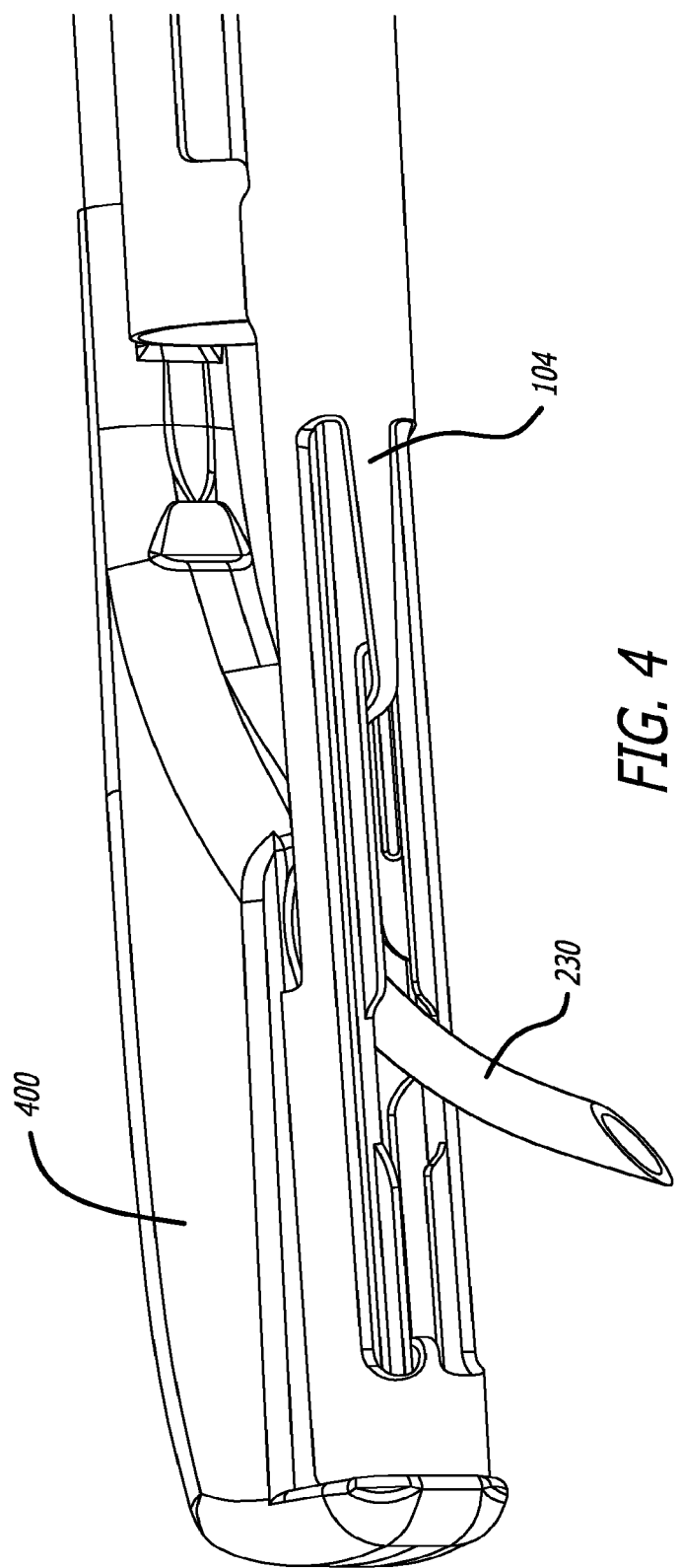
FIG. 4 is a perspective view in partial cross-section depicting partial advancement of a needle assembly.

Referring now to FIGS. 2-4, there is shown one embodiment of a delivery device 100. This device is configured to include structure that is capable of both gaining access to an interventional site as well as assembling and implanting one or more anchor assemblies or implants within a patient's body. The delivery device 100 can be configured to assemble and implant a single anchor assembly or implant a single bodied anchor or multiple anchors or anchor assemblies. The device is further contemplated to be compatible for use with a 19 F or 20 F sheath. The device additionally includes structure configured to receive a conventional remote viewing device (e.g., an endoscope) so that the steps being performed at the interventional site can be observed.

Prior to use of the present device 100, a patient typically undergoes a five day regimen of antibiotics. A local anesthesia can be employed for the interventional procedure. A combination of an oral analgesic with a sedative or hypnotic component can be ingested by the patient. Moreover, topical anesthesia such as lidocaine liquids or gel can be applied to the bladder and urethra.

The anchor delivery device 100 includes a handle assembly 102 connected to elongate member 104. Elongate member 104 can house components employed to construct an anchor assembly and is sized to fit into a 19 F or 20 F cystosopic sheath for patient tolerance during a procedure in which the patient is awake rather than under general anesthesia. The assembly is intended to include structure to maintain its positioning within anatomy.

The anchor delivery device 100 further includes a number of subassemblies. A handle case assembly 106 including mating handle parts that form part of the handle assembly 102. The handle assembly 102 is sized and shaped to fit comfortably within an operator's hand and can be formed from conventional materials. Windows can be formed in the handle case assembly 106 to provide access to internal mechanisms of the device so that a manual override is available to the operator in the event the interventional procedure needs to be abandoned.

In one embodiment, the delivery device 100 is equipped with various activatable members that facilitate assembly and delivery of an anchor assembly at an interventional site. A needle actuator 108 is provided and as described in detail below, effectuates the advancement of a needle assembly to an interventional site. In one approach, the needle assembly moves through a curved trajectory and exits the needle housing in alignment with a handle element, and in particular embodiments, in alignment with the grip. In various other embodiments, the needle housing is oriented such that the needles exits the housing at either the two o'clock or ten o'clock positions relative to a handle grip that is vertical. A needle retraction lever assembly 110 is also provided and when actuated causes the needle assembly to be withdrawn and expose the anchor assembly.

In one particular, non-limiting use in treating a prostate, the elongate member 104 of a delivery device is placed within a urethra (UT) leading to a urinary bladder (UB) of a patient. In one approach, the delivery device can be placed within an introducer sheath (not shown) previously positioned in the urethra or alternatively, the delivery device can be inserted directly within the urethra. When employing an introducer sheath, the sheath can be attached to a sheath mount assembly (described below). The patient is positioned in lithotomy. The elongate member 104 is advanced within the patient until a leading end thereof reaches a prostate gland (PG). In a specific approach, the side(s) (or lobe(s)) of the prostate to be treated is chosen while the device extends through the bladder and the device is turned accordingly. The inside of the prostate gland, including the adenoma, is spongy and compressible and the outer surface, including the capsule, of the prostate gland is firm. By the physician viewing with an endoscope, he/she can depress the urethra into the prostate gland compressing the adenoma and creating the desired opening through the urethra. To accomplish this, the physician rotates the tool. The physician then pivots the tool laterally about the pubic symphysis PS relative to the patient's midline.

The delivery device is at this stage configured in a ready state. The needle actuator 108 and the needle retracting lever 110 are in an inactivated position.

Upon depression of the needle actuator 108, the needle 230 (See FIG. 4) is advanced from within the elongate member 104. The needle can be configured so that it curves back toward the handle as it is ejected. In use in a prostate intervention, the needle is advanced through and beyond a prostate gland (PG). Spring deployment helps to ensure the needle passes swiftly through the tough outer capsule of the prostate without "tenting" the capsule or failing to pierce the capsule. In one approach, the needle is made from Nitinol tubing and can be coated with Parylene N. Such a coating helps compensate for frictional or environmental losses (such as wetness) that may degrade effectiveness of needle penetration.

Certain anchor delivery devices include springs as part of the mechanisms that drive a needle or penetrating member, deploy an anchor, cut a connector, or perform other functions related to device delivery. The devices may include springs that are preloaded with potential energy when the user removes the device from packaging. Preloaded springs can be susceptible to degradation over time when stored in a loaded state, whether that state is tension or compression. Spring degradation may affect a device's shelf life. Also, spring degradation can affect the consistency of the device as the spring force can change over time. Further, loaded components may creep due to constant stress.

Figure 5:
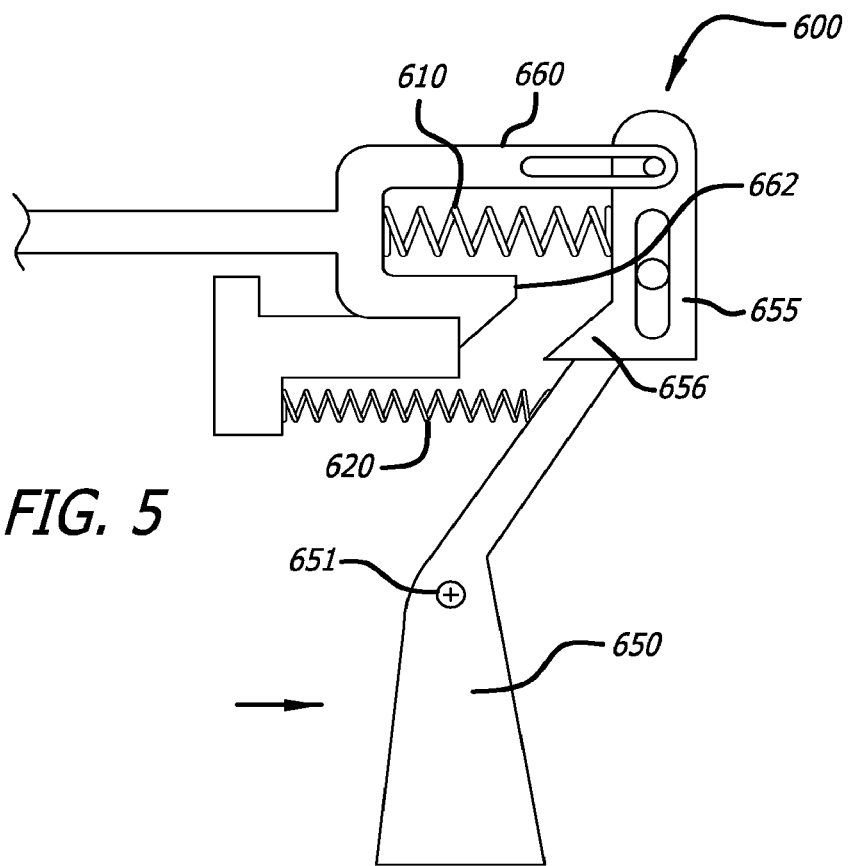
FIGS. 5-6 illustrate embodiments of a handle assembly for an anchor delivery system that does not pre-load energy in springs while the device is in a stored state.

FIG. 5 illustrates one embodiment of a handle assembly that does not pre-load energy in springs while the device is in a stored state. Handle assembly 600 includes two springs a needle drive spring 610 and a reset spring 620. Neither the needle drive spring 610 nor the reset spring 620 stores potential energy in their stored state. That is, the springs and components are not under stress from spring loading during shipping or storage of the device.

A user loads energy into the needle drive spring 610 using a first actuator 650, which can be a lever or trigger. In this embodiment, the user can squeeze the first actuator 650 like a trigger. The first actuator 650 pivots at pivot point 651 and causes needle drive traveler 655 to compress both needle drive spring 610 and a reset spring 620. When the needle drive spring 610 is loaded with sufficient energy to drive the needle (not pictured) through the target tissue, the needle drive spring 610 is released by the mechanical action of the needle drive traveler 655. For example, a ramp 656 can disengage a latch 662 on a needle drive assembly 600 and allow the needle drive spring 610 to unload its stored energy and drive the needle. Other latching mechanisms are also within the scope of the invention.

The return spring 620, which is loaded when the first actuator 650 is activated by the user, has sufficient energy to force the needle drive assembly 660 back into its original position. Returning needle drive assembly 660 to its original position includes forcing the latch 662 back into its latched position. Further, returning the needle drive assembly 660 to its original position also works to retract the needle. While FIG. depicts the needle drive spring 610 and the return spring 620 as being loaded by compression, one or both could be loaded by tension, and the system can achieve the same end. This embodiment provides a system for: (1) avoiding stored energy in the springs of the delivery device and (2) returning the needle drive mechanism to its initial state, including retracting the needle.

Figure 6:
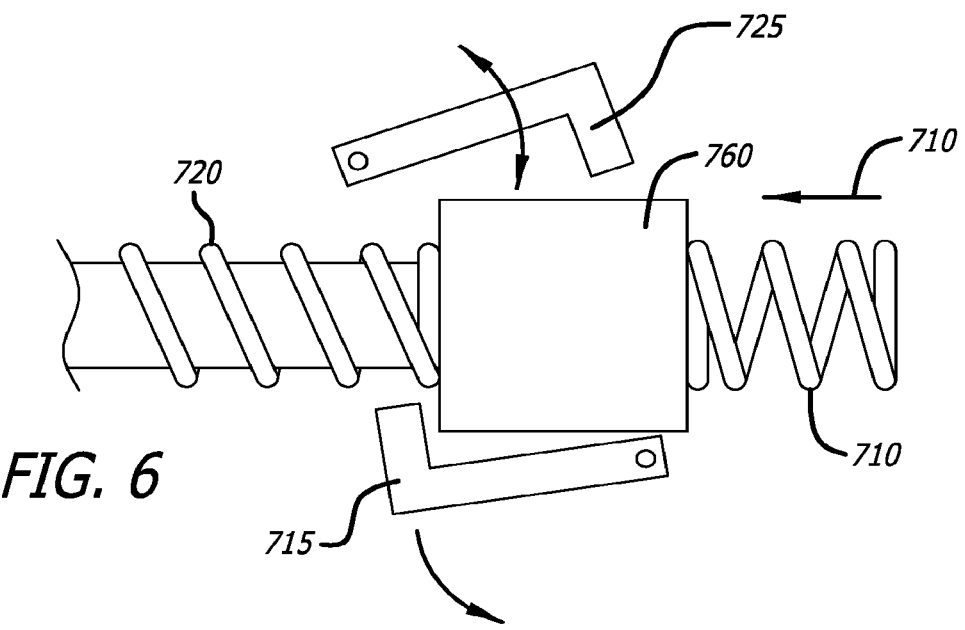

In another embodiment, the needle drive assembly is returned to its initial state and the needle is retracted by the action of a return spring. As illustrated schematically in FIG. 6, the deployment spring 710 is loaded by the user activating a first actuator (not pictured), such as a lever or a trigger. A deployment pawl 715 restricts the motion of the needle drive assembly 760 until the first actuator reaches a point in its travel such that it disengages the deployment pawl 715. The deployment pawl 715 can be disengaged by a variety of mechanical methods, including the latching/unlatching mechanism described above. When the deployment pawl 715 is disengaged, the needle drive assembly 760 drives the needle (not pictured) and loads the return spring 720. Further, as the needle drive assembly 760 drives the needle, a return pawl 725 engages the proximal section of the needle drive assembly 760 and the deployment spring 710 can optionally decouple from the needle drive assembly 760.

To load the return spring 720, the deployment spring 710 must have enough load to both drive the needle with the desired force and to load the return spring 720. Advantageously, the load required by the return spring 720 to withdraw the needle can be significantly less than the drive load because the needle is being retracted. That is, the drive load may have to be large enough to initially penetrate tissue and overcome frictional forces in the distal section of the delivery system. However, the return spring 720 does not need load to penetrate tissue and the frictional forces on the return of the needle are lower than upon initial drive.

The return pawl 725 is released by the user, or optionally by mechanical action prompted by the first actuator, to retract the needle using the load of the return spring 720. In some embodiments, it may be desirable to allow the user to release the return pawl 725 and in others the return pawl 725 is released directly engaging the user in a step independent from using the first actuator. The return spring 720 can return the needle drive assembly past the deploy pawl 715. Thus, the system is returned to its initial state where the deploy spring 710 can be loaded again by the first actuator.

The anchor delivery system uses a needle or other penetrating member to deploy anchors within tissue. In some deployments, the needle may strike bone tissue, calcification, or other objects or surfaces that cause damage to the needle or needle tip. For an anchor delivery device configured to deploy multiple anchor assemblies via multiple needle advancements, a damaged needle can cause complications in deployment.

Figure 7A:
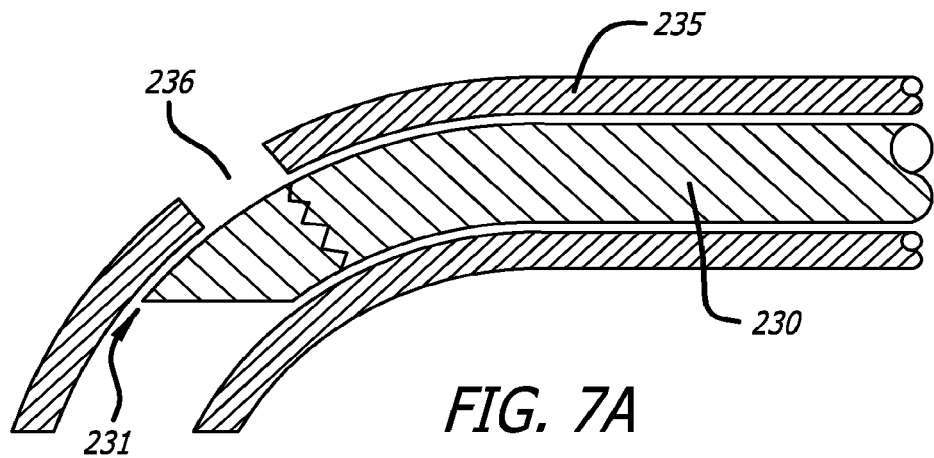
FIGS. 7A-7B are cross-sectional views of features for detecting a damaged needle.
Figure 7B:
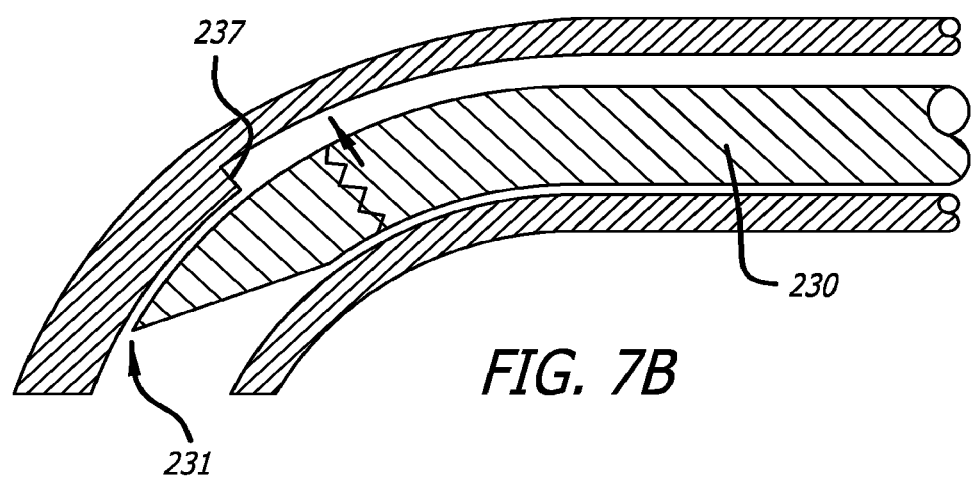

In certain embodiments, the mechanical integrity of a multi-use needle is assessed by a mechanism in the distal section of the delivery device. FIG. 7A illustrates a curved section of a needle tube 235 and a needle 230 within the needle tube 235. In this embodiment, the needle tube 235 includes a window 236 on the outer portion 231 of the curvature of the needle tube 235. Since the needle 230 engages the outer portion 231 of the curvature as that section of the needle tube 235 directs the needle 230 around the curve, a defect on the needle 230 such as a missing, kinked, or bent tip will cause the needle 230 to partially enter the window 236 and engage on side of the window 236. FIG. 7B illustrates an alternative embodiment in which a lip 237 inside the outer portion 231 of the curvature can similarly engage the end of a needle 230 with a defect such as a missing, kinked, or bent tip. Thus, a needle 230 with a missing, kinked, or bent tip will be stopped from advancing and the needle stopping will alert the user of the needle defect.

In certain embodiments, the integrity of the needle can be visually assessed via the cystoscope. After a deployment, the needle can be partially retracted such at it is in the field of view of the cystoscope and the integrity of the needle can be directly observed by the user.

Figure 8:
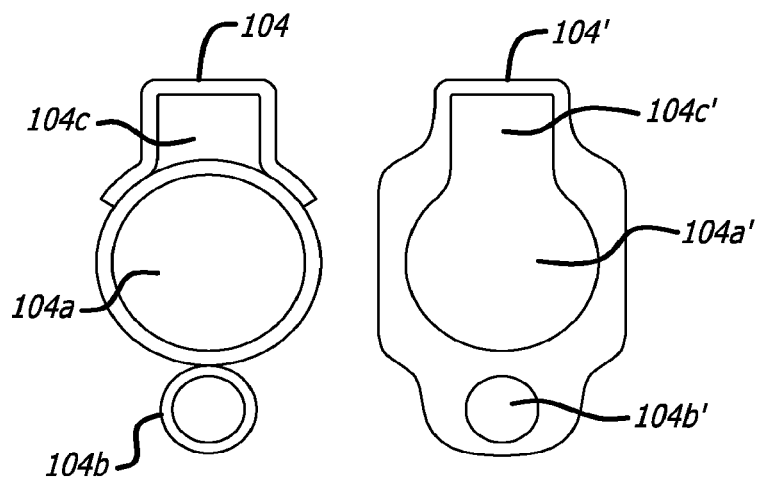
FIG. 8 is a cross-sectional view of two embodiments of a section of an elongate member for an anchor delivery system.

In certain embodiments, at least part of the elongate member 104 of the delivery device can be formed by injection molding a two-part, clam shell styled design. The two parts can be joined by press fit, snap fit, adhesives, solvent, overmold, shrink tubing, or other equivalent methods. FIG. 8 illustrates a comparison of the cross-sections of an elongate member 104 assembled from tubes and a channel versus the two-part injection molded elongate member 104'. Both cross-sections contain a cystoscope lumen (104a, 104a'), a needle lumen (104b, 104b'), and an anchor lumen (104c, 104c'). The clam-shell design can be incorporated along some or all of the length of the elongate member 104'. An injection molded section 104 can be created with a single part that does not require joining. The lumens can be made with alternating shut-offs in the mold, or alternatively, the lumens are not closed lumens. Rather, the lumens of the elongate member 104 provide sufficient constraint to the members that traverse within without using full circumference lumens. Such embodiments enable a less complicated mold.

In other embodiments, one or more of the parts of the two part design is stamped. The stamped parts can be joined by press fit, snap fit, adhesives, solvent, overmold, shrink tubing, or other equivalent methods. Alternatively, the entire elongate member 104 could be a single stamped part with lumens that are not closed, but rather provide only enough constraint to the members that traverse within to keep those members within the lumens, but with non-closed lumens enable less complex stamping tooling.

In certain embodiments, at least part of at least one of the three lumens of the elongate member can be eliminated. In one embodiment, shorter tube segments can replace an entire tube segment. For example, the needle tube can be replaced with a short tube segment in the proximal handle and at the distal end such that the needle is constrained near its ends but does not require a lumen for a substantial part of the mid-section of the needle. Clips or flanges could be used in addition to or in place of the short tubes. Alternately, the cystoscope tube can be eliminated and replaced with tubes or clips or flanges.

In some embodiments, the elongate member is detachable and reusable, while the proximal handle is single use. The proximal handle can store the implants as well as provide the loads necessary to drive the needle, deliver the anchors, and cut the connector. Also, the shaft may house multiple anchor components and may house the needle.

The method of use of the anchor delivery system can incorporate the use of a cyctoscope, endoscope, or similar visualization device. In some embodiments, the proximal handle includes a scope lock with no moving parts for locking a cystoscope to the handle prior to performing the treatments disclosed herein. The lack of moving parts reduces the cost and increases the reliability and ease of use.

Figure 9:
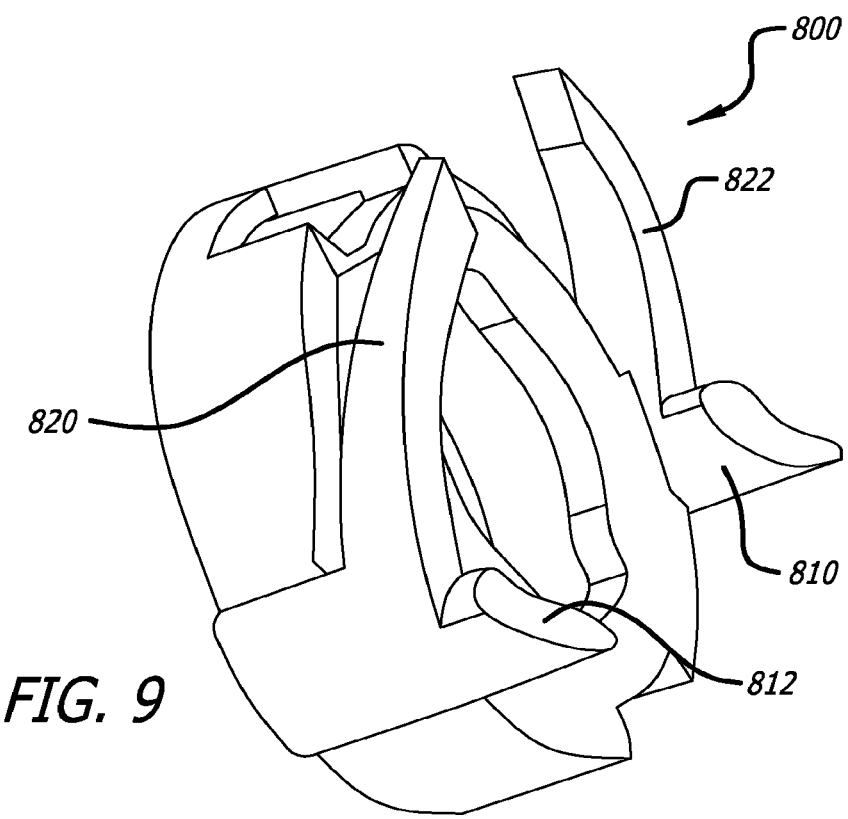
FIG. 9. is a perspective view of a scope lock according to certain embodiments.

FIG. 9. illustrates a scope lock 800 according to certain embodiments. The scope lock includes a pair of stops (810, 812) at about 3 o'clock and about 9 o'clock. A scope is inserted with the light post between these two stops 810, 812 on the 12 o'clock side of the scope lock circle such that the scope cannot be twisted downward with respect to stops 810 and 812 so that the light post is toward the 6 o'clock position. The scope can now only be twisted towards the 12 o'clock position. The scope lock further includes a pair of flexible ramp features (820, 822). The light post of the cystoscope rotates up one or the other of these ramps (820, 822) and snaps into the 12 o'clock position. The snap fit is strong enough such that the user may rotate the camera relative to the scope but not overpower the stop portions of the ramps.

In some embodiments, a movable lens or electronic image sensor can be integrated into an endoscopic telescope for a disposable device into which a telescope is inserted. Alternatively, more than one lens can be positioned on a telescope and electronically selected to provide different views from the telescope. A movable lens or more than one lens, advantageously, can provide views in different directions, at different magnifications, or differently sized fields of view. Such lenses or image sensors can be integrated with a standard telescope in a variety of ways. For example, the telescope could be a standard telescope and the movable lens could be on the delivery device such that when the telescope and the delivery device are mated together adjusting the lens on the delivery device provides a variety of images to the telescope. Alternatively, the lens on the delivery device could be exchangeable to provide different views. In another example, an adjustable-position image sensor could be used integrally with the delivery device to capture the image. Finally, a prism could be used to provide multiple views to the telescope and electronic image processing could be used to provide stereo, compound, or selective partial imaging to the user.

In some embodiments, the first anchor is delivered via a needle tip placed at the end of a wire. Needle tip can be attached to the wire by press fit, snap fit, adhesives, solvent, overmold, shrink tubing, or other equivalent methods. The connector can run along the side of the anchor delivery wire. Advantageously, using a wire rather than a needle for travel along a substantial section of the needle tube reduces the cost of the needle assembly. Only the needle tip is hollow.

In some embodiments, a tape-like or ribbon-like needle or wire is used in the needle assembly. Advantageously, a ribbon-like needle will preferentially to bend to tighter radius in one direction than in another direction. Thus, the needle can have sufficient column strength for penetrating tissue while also having sufficient flexibility in a direction in which flexibility is desired.

Figure 10:
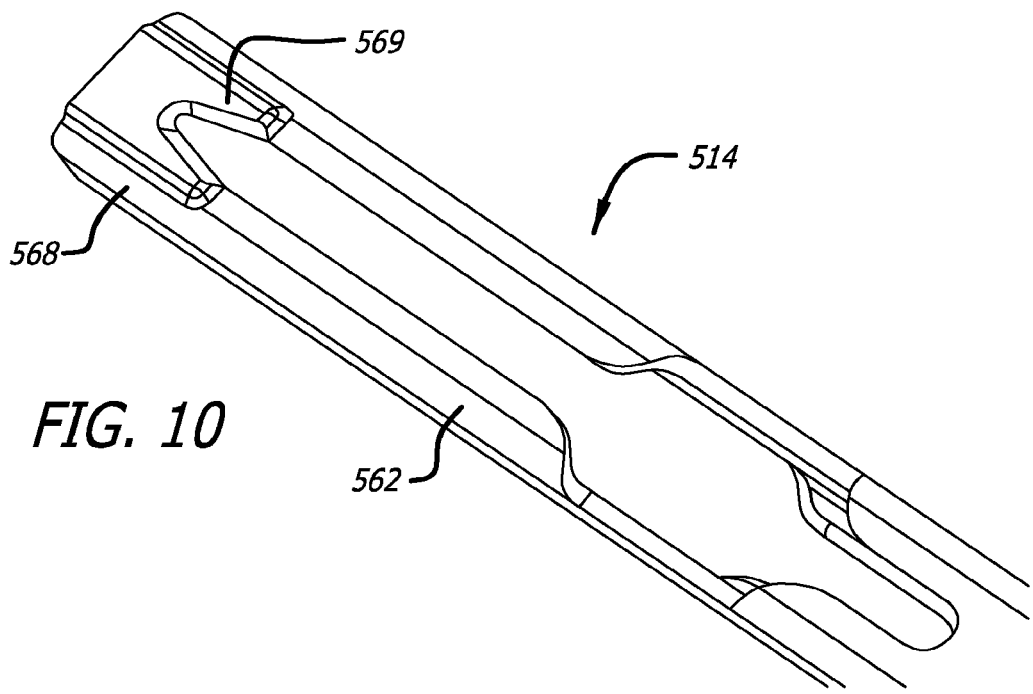
Figure 11:
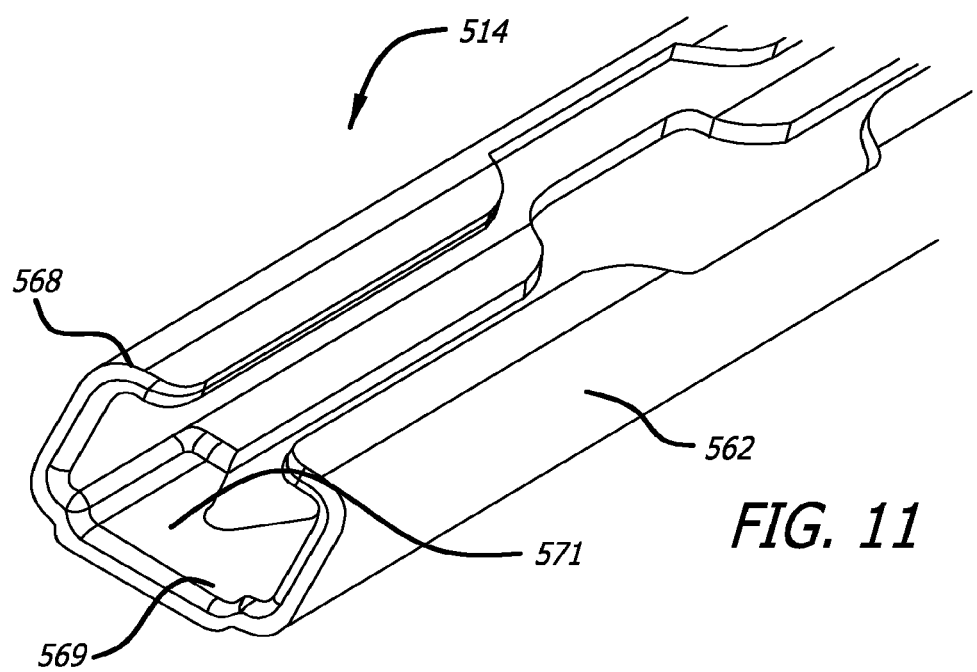

As best shown in FIGS. 10 and 11, an embodiment of the cutter assembly 514 includes elongate cutter tube 562. A distal end 568 of the cutter tube 562 is configured with a blade 569 so that once the cutter assembly 514 is withdrawn, the blade can sever as desired a connector of an anchor assembly. In one particular embodiment, the cutter 514 can be formed from ground 17-4 PH stainless steel blank. Various structures are contemplated for incorporation into the cutter assembly to facilitate a clean severing of a connector as well as to aid in assembling a proximal component of an anchor assembly to the connector. For example, as best seen in FIG. 11, the cutter blade 569 includes a coined out underside that is intended to be offset from a bottom side of a proximal anchor by about 0.0035+ 0.0010 inches to cut a nominal 0.015 inch diameter connector. In this way, the proximal anchor can exit a cutter without deforming or compressing a suture or connector tag, and the strength of the connector to anchor connection is maintained. Alternatively, the feature that cuts the suture can by a non-sharp feature. Therefore, instead of cutting via a blade, it could cut the suture through a shearing action where two non-sharp elements slide past each other and create a shearing action through the suture.

As shown in FIGS. 12-14, the cutter 514 can define a generally rectangular elongate single body that can be formed by stamping and bending. An interior of the body is sized and shaped to receive a proximal anchor component 550. A proximal end portion of the cutter 564 can further include anti-buckling tabs 551 and extensions 553 intended to snap fit to a cutter block (described below). Lance-out structures 555 are also contemplated to be spaced along the cutter body which facilitate alignment of the cutter 514 within the shaft assembly.

Figure 16:
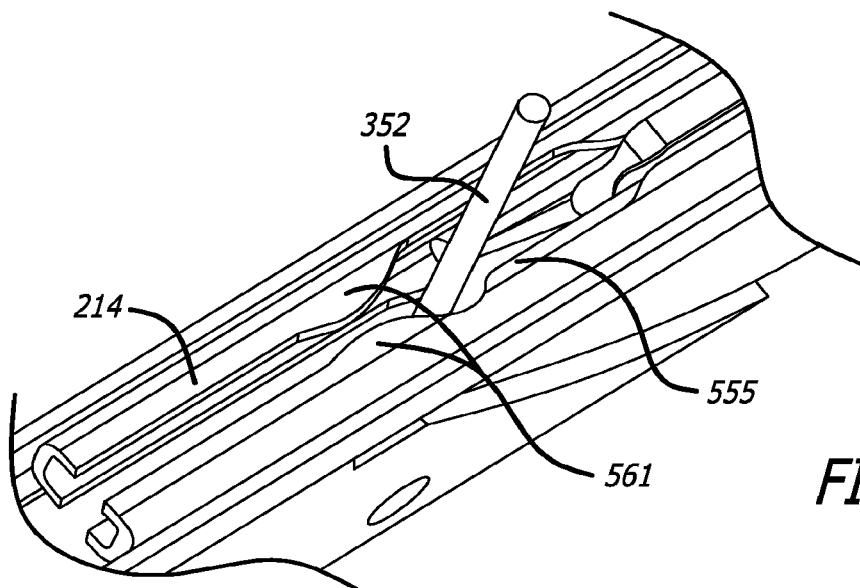

To eliminate snagging of a connector, walls defining a needle window 557 formed in the cutter 514 can be contoured to help properly guide the connector into a suture capture area 559. As best seen in FIG. 15, a proximal portion of the needle window 557 defines a gradual slope for directing the connector within the capture area 559. In a related approach (FIG. 16), bumps 561 can be formed on connector guiding structure to further aid in properly positioning a connector 352 for engagement with a proximal anchor component 555.

Figure 17:
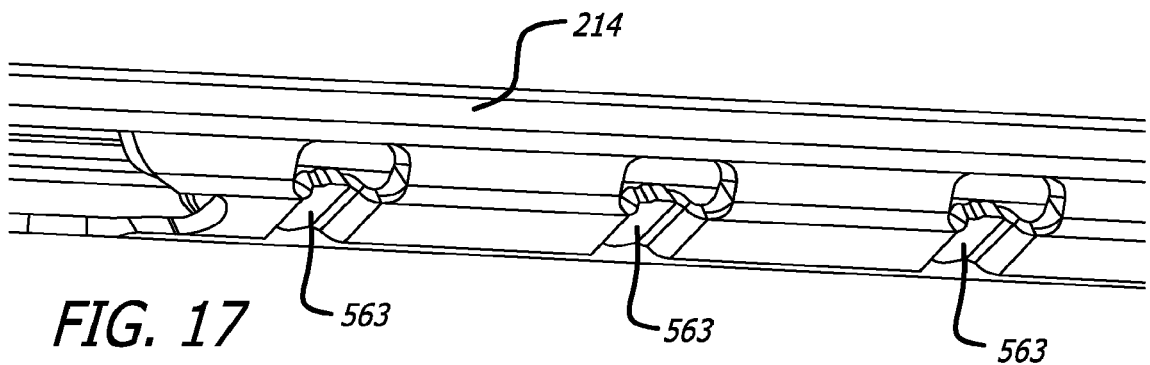
Figure 18:
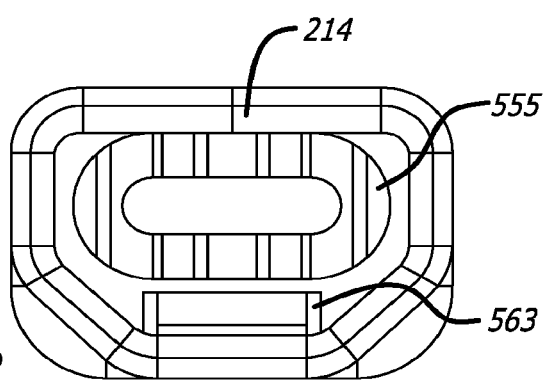

Moreover, as depicted in FIGS. 17 and 18, the cutter 214 can further include skew limiting projections 563 extending internally within the generally tubular cutter 214. As best seen in FIG. 18, the projections 563 help to maintain proper positioning of a proximal anchor component 555 within the cutter 214.

Figure 19:
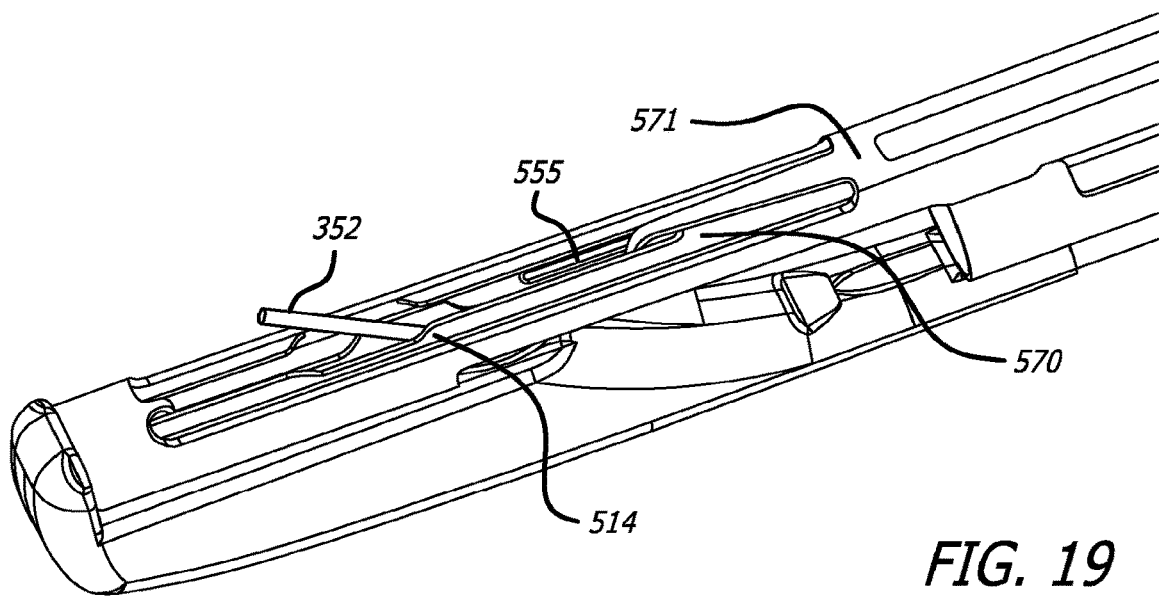
FIGS. 19-20 are perspective views depicting features of a suture guide.
Figure 20:
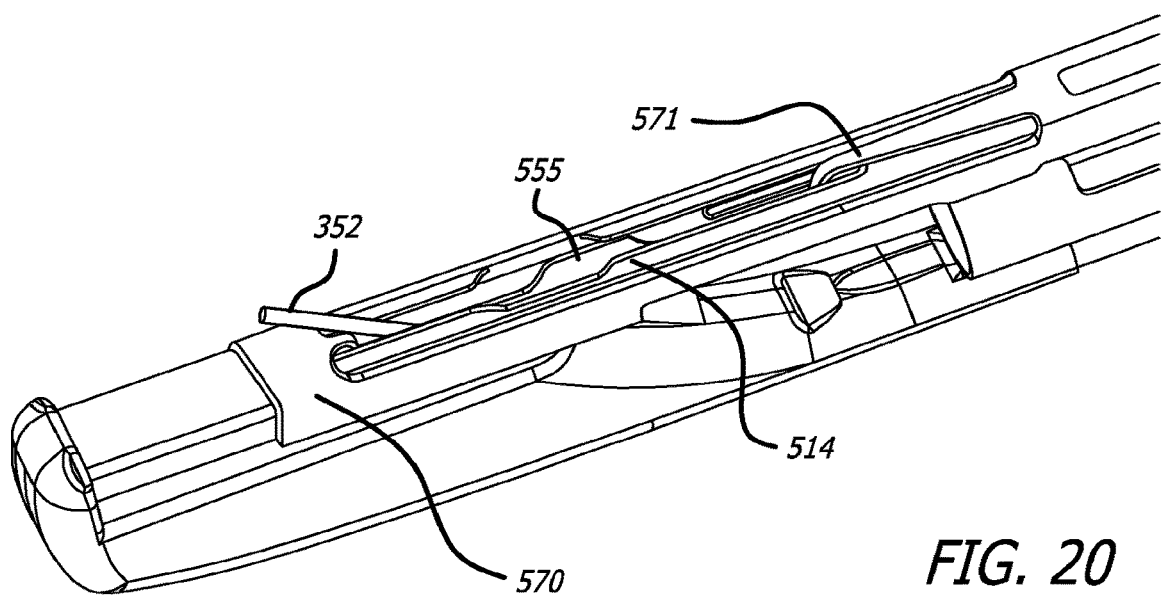

In a further aspect illustrated in FIGS. 19-20, the present device can include a suture alignment slide 570 configured to slide under a cover 571 and over the cutter 514. The cover 571, in turn, includes a finger projector 573 which is sized and shaped to control and guide the movement of a proximal anchor 555. The alignment slide 570 indexes the connector 352 to a centerline of the cutter 514. It also operates to pull the connector 352 proximally for indexing within the proximal anchor component 555 to thus enhance connector capture by the anchor component 555. In other embodiments, a distal end of the needle housing itself can alternatively or additionally include a slot or notch for properly registering the connectors during device use and particularly when tension is being applied to the connector.

In order to accomplish the attachment of the proximal anchor 555 to the connector 352, a pusher assembly 575 is configured to extend within the cover 571 (See FIGS. 21-23). The pusher assembly 525 can include a proximal portion 577 which extends to the handle of the device (connected to pusher block as described below) and a distal portion 579 which attaches to the proximal portion 577. The distal portion 579 can further include an extension 581 sized to receive the length of a proximal anchor 555. The thickness of the extension 581 is chosen to ensure a 0.004 inch gap between a cutter and a bottom portion of the proximal anchor 555 so that a connector tag remains after its severing by the cutter. The cover 571 can further include an anchor stop 583, which is configured at a distal end of the cover 571. The anchor stop 583 is sized and shaped to protect the proximal anchor 555 from becoming trapped within the cover 571 after its engagement with the proximal anchor 555. Through its connection to the pusher of the pusher block 604, the pusher assembly 575 is advanced distally which, in turn, results in the proximal anchor component 555 engaging the connector 352 (See also FIG. 23).

Next, the pusher block 604 contacts a first end of the cutter pawl 608 causing its second end to rotate away from the engagement with the cutter block 565. It is to be noted that the timing of first advancing a proximal anchor component 555 and then cutting a connector 352 to length can be controlled by the force applied by the spring 606, the distance the pusher block 604 is to travel, and/or the location of the first end of the cutter pawl 608. A proximal end of the cutter 214 is attached to the cutter block 565. As the cutter block 565 moves proximally, the cutter 214 is withdrawn.

Accordingly, release of the pusher assembly advances the second component 555 of an anchor assembly into locking engagement with a connector of an anchor assembly (See FIG. 23). Such action causes the pusher 575 to advance the anchor component 555 onto a connector (e.g., a suture) while the connector is being held by the tool with sufficient force and the anchor is advanced with sufficient speed and force to seat the anchor 555 with reliable retention force.

Figure 24A:
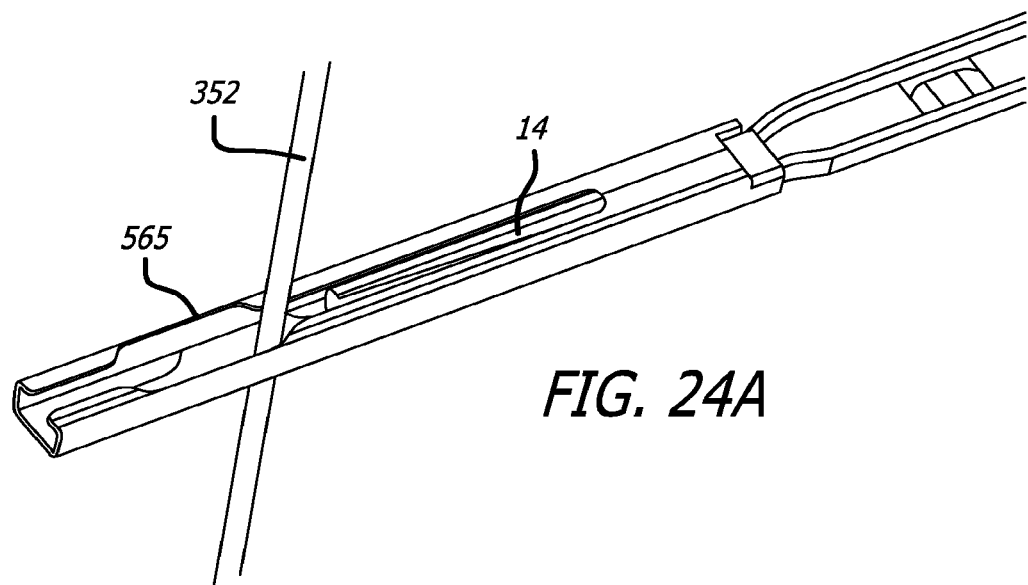
FIGS. 24A-24E are perspective views depicting features and the operation of a single assembly that acts as a pusher assembly and a cutter assembly.
Figure 24B:
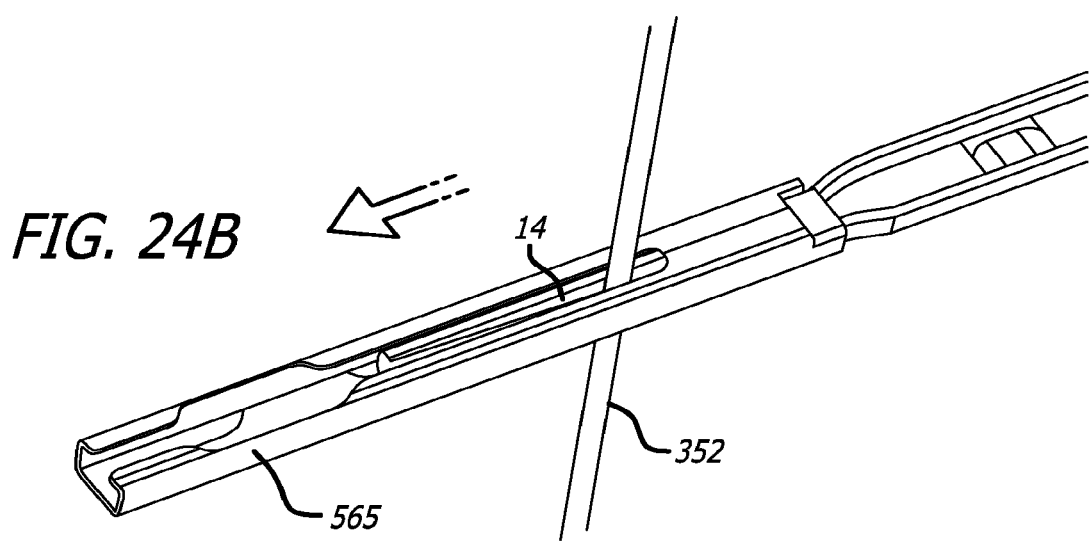
Figure 24C:
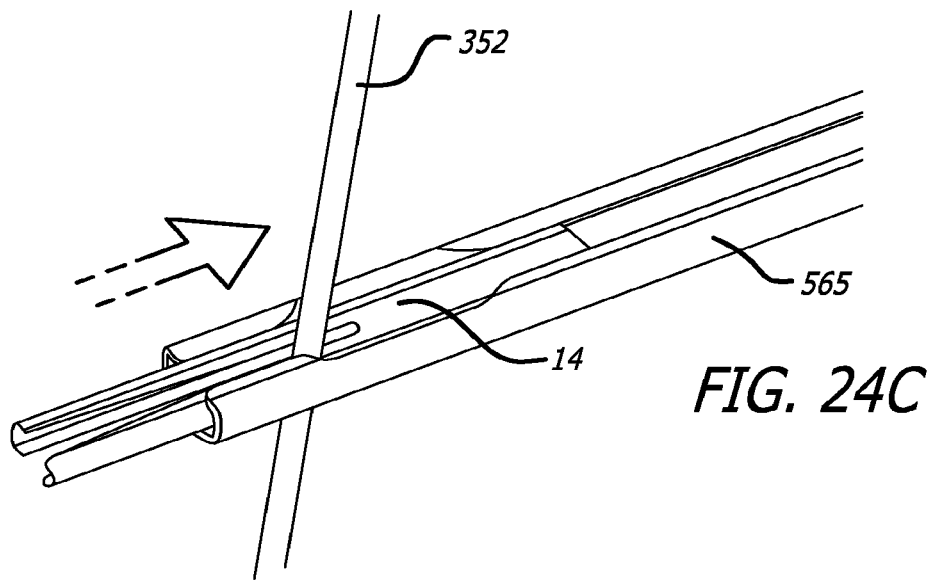
Figure 24D:
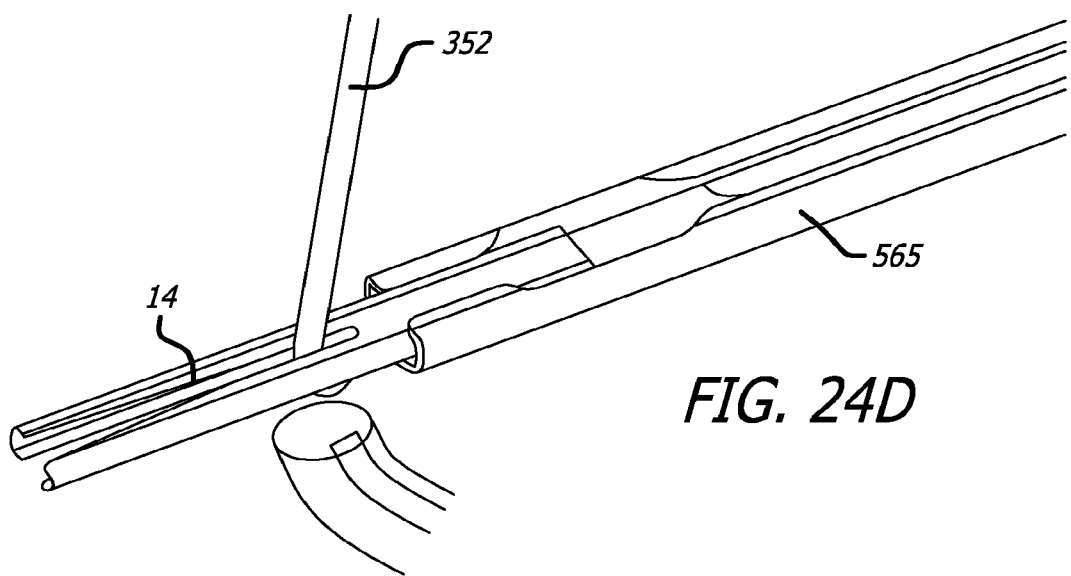
Figure 24E:
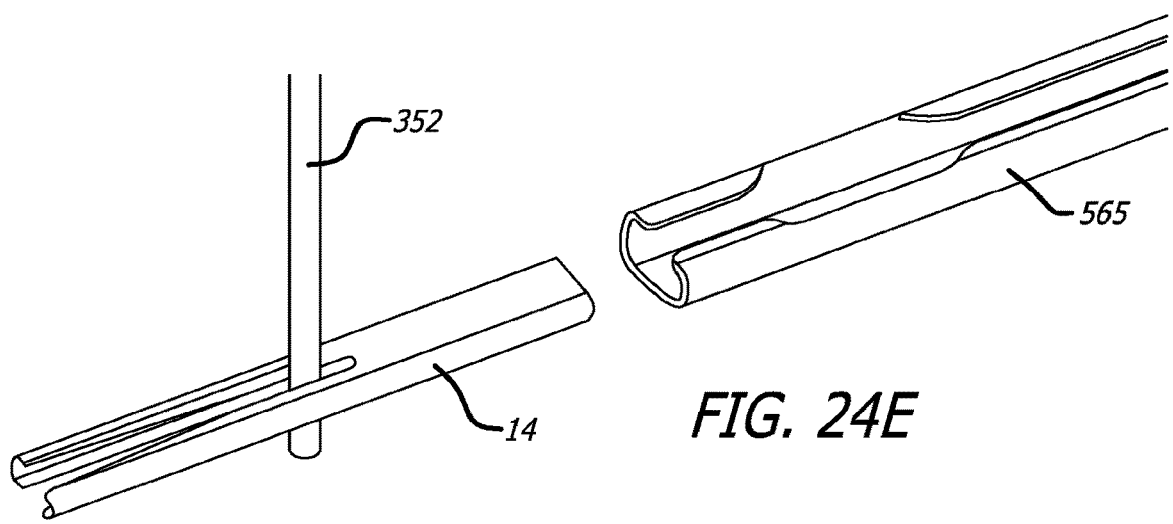

In another embodiment, the pusher assembly 575 for pushing the second anchor component 14 is eliminated by using a single assembly that engages the second anchor 14 with the connector 352 and also cuts the connector 352. FIG. 24A illustrates the second anchor 14 and the cutter block 565 in position to engage the second anchor 14 after the connector 352 has been tensioned. FIG. 24B illustrates the cutter block 565 being pushed distally by an actuator (which activates a load supplied by a spring or gas or other loading methods described herein). The second anchor component 14 is engaged to the connector 352 during the distal driving step. FIG. 24C illustrates the cutter block 565 being pulled proximally by any of the return or retract mechanisms described herein. The second anchor component 14 remains fixed relative to the movement of the cutter block 565 since the second anchor component 14 is engaged onto the connector 352. FIG. ED illustrates the connector 352 having been cut by the sharp edge of the cutter block 565. FIG. EE depicts the second anchor component 14 attached to the connector 352 and the connector 352 having been cut.

In alternative embodiment, the second anchor can be held in position via tension, for example, during retraction of a cutter with a relatively dull edge. The cutter would help seat the second anchor on the connector prior to the connector being cut.

In some embodiments, one or more springs are replaced with a gas-driven mechanism. The mechanism can be driven by gas canisters, such as a $CO_2$ canister, or it can be driven by a compressed gas system, such as a compressed air line or a compressed gas tank, or by suction or fluid lines. One or more of the steps of needle deployment, connector tensioning, second anchor component attachment, and connector cutting can be powered by the gas-driven mechanism. The gas-driven system can include bleed valves, regulators, pistons, and other fluid controls typically associated with gas-powered devices.

In certain embodiments, the friction between the needle tube (or its equivalent structure in embodiments of the various elongate members disclosed herein) and the needle must be overcome by the energy load that drives the needle. Reducing the friction experience by the needle, particularly at the curvature in the distal section of the needle assembly, can reduce the load required to advance the needle. In certain embodiments, even though the needle is formed with a curved section at its distal end, the radius of curvature of the distal section of the needle assembly is tighter than the radius of curvature of the curved distal section of the needle. The curvature of the needle is less tight to provide a generally orthogonal track from the prostatic capsule to the prostatic urethra. A greater curve in the distal end of the needle could create difficulties in seating the distal anchor on the prostatic capsule. Further, the needle assembly has to redirect the needle in a relatively small amount of space due to the low profile of the delivery system. Thus, its radius should be as tight as possible. Balancing these opposing requirements while closely aligning the radii can reduce the friction experienced by the needle. In some embodiments, the radius of the needle is about 0.957" while the inner and outer radii of the needle tube are 0.805" and 0.802", respectively.

FIGS. 25A-H illustrates various views of an anchor delivery system handle 1000 configured to accept cartridges 1200. Each cartridge 1200 contains at least one anchor assembly. The anchor delivery system handle 1000 is configured to deliver the anchor assembly and return to a loaded state such that the spent cartridge can be replaced with a new cartridge and the deployment process can be repeated without requiring the user to load mechanical energy into the springs within the device.

Preferably, the device is stored and shipped with some or all of the springs not storing mechanical energy. A removable insert can be included in the cartridge chamber 1010 of the anchor delivery system handle 1000. After opening the package containing the anchor delivery system handle 1000, the user must remove the insert before there is space in the anchor delivery system handle 1000 for inserting a new cartridge 1200. The removable insert and the anchor delivery system handle 1000 are configured such that removing the removable insert loads the spring 1050 or springs 1050, 1055 in the system with an initial energy load and positions the firing sled 1060 in the cartridge chamber 1010 to accept the new cartridge 1200. For example, the user can pull in a proximal direction on a handle on the removable insert until the insert reaches a point in the cartridge chamber 1100 that allows the user to remove the insert. The removable insert can be pulled out when it clears protrusions, cuts, or other structural features in the anchor delivery system handle 1000.

The firing sled 1060 includes slots that align with pusher tabs 1012, 1014 on cartridge 1200. The slots and pusher tabs are complementary mechanisms that allow the transfer of energy from the spring 1050 via the firing sled 1060 to fire the needle in the cartridge 1200. The cartridge 1200 snaps into place within the cartridge chamber 1010 after the slots and pusher tabs are aligned or is locked in place with a chamber door or latch.

Figure 25B:
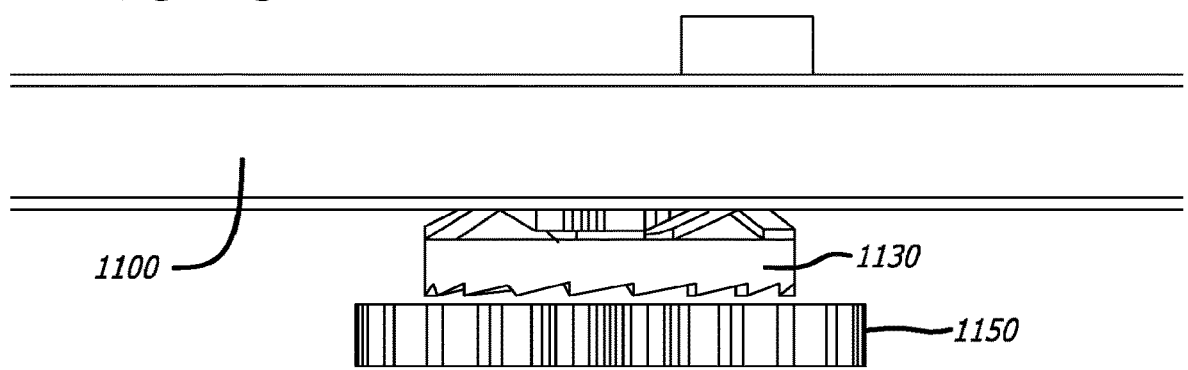
FIGS. 25A-25J are various views of an anchor delivery system that includes a handle configured to accept cartridges.
Figure 25A:
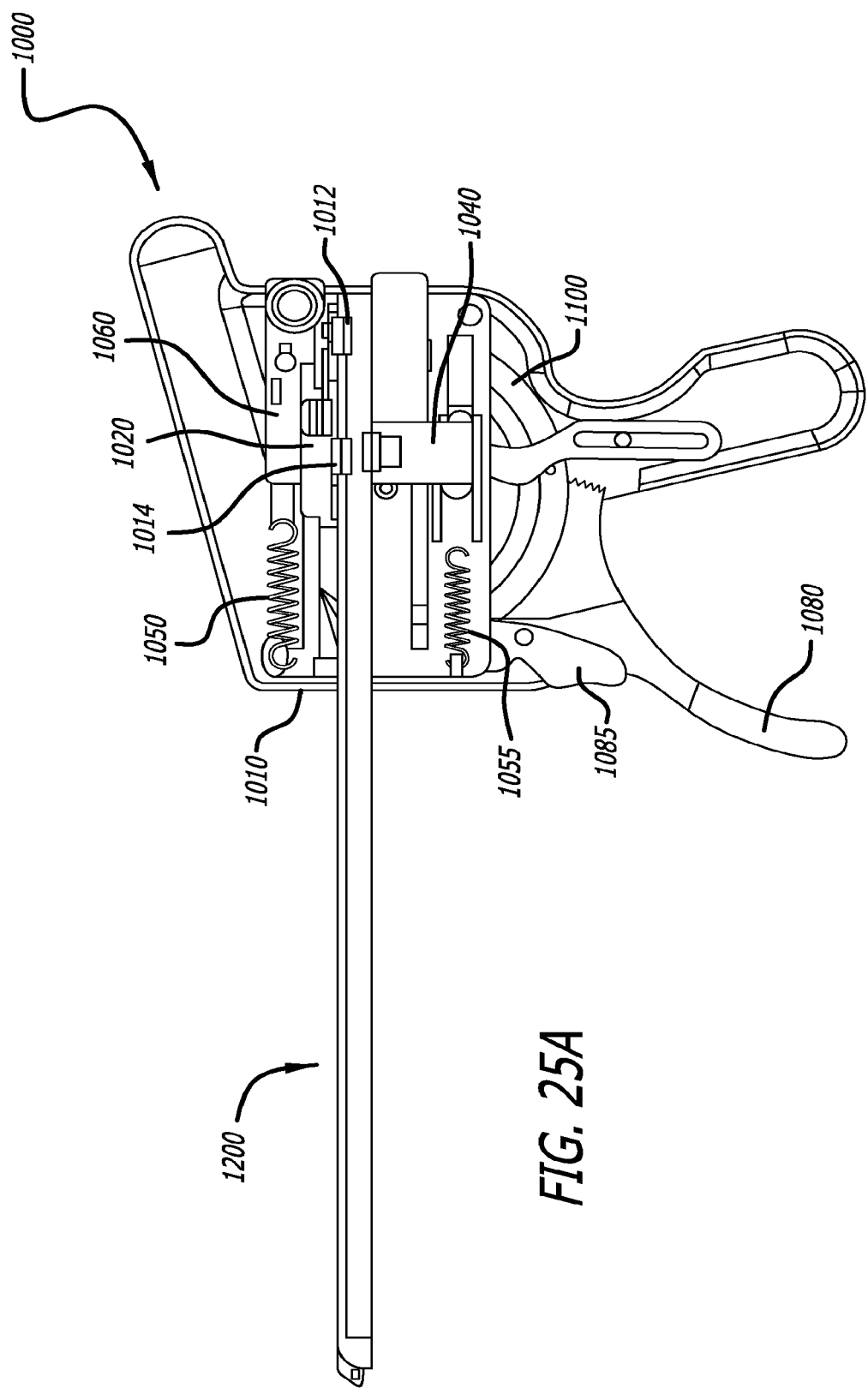
Figure 25C:
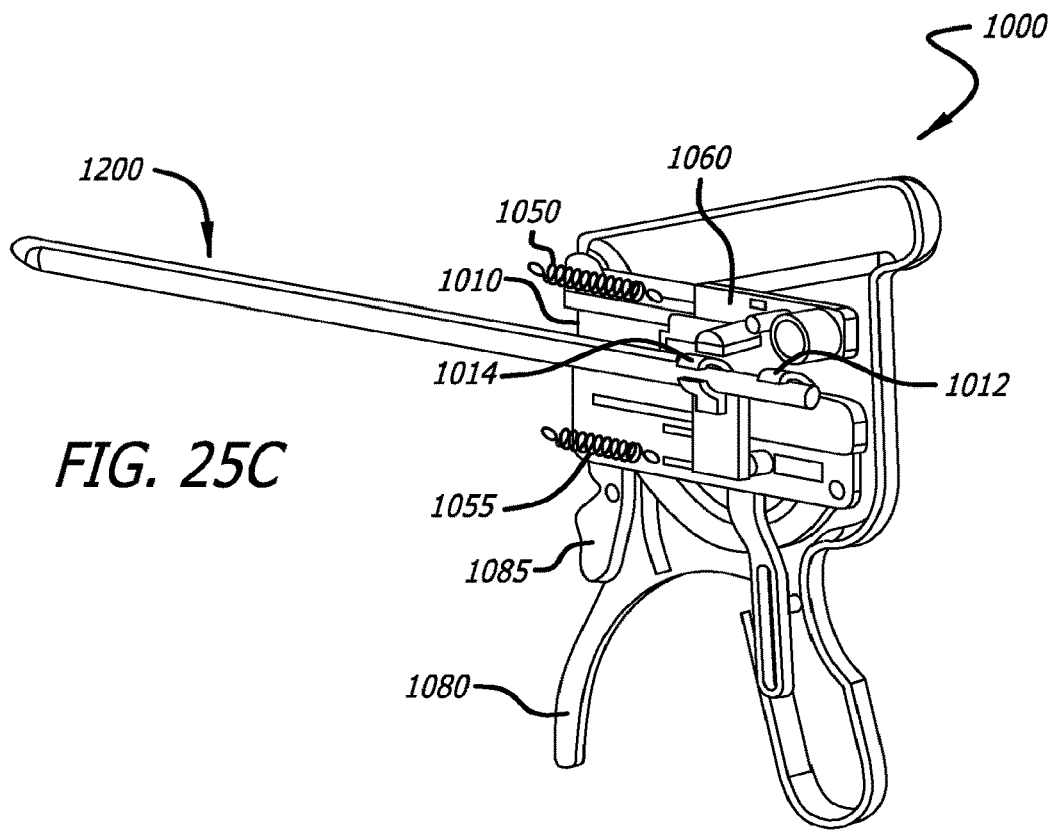
Figure 25D:
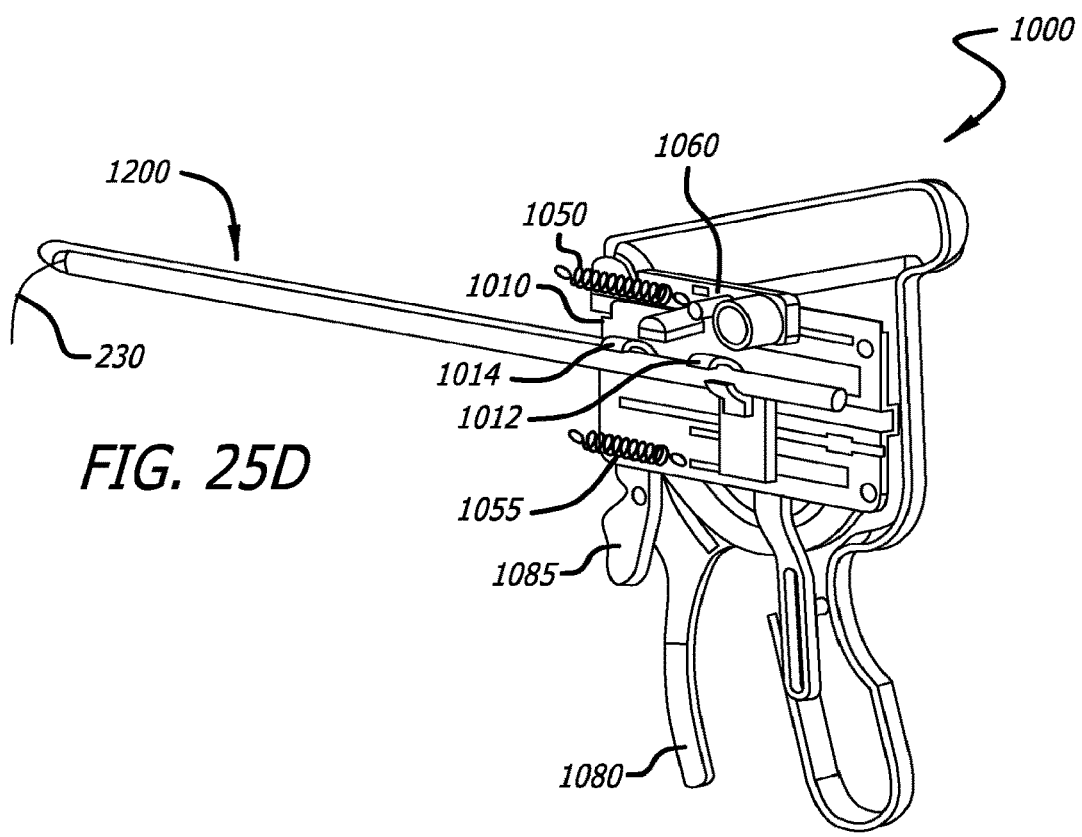

To fire the needle from the distal end of cartridge 1200, safety 1085 is squeezed by the user. Squeezing the safety 1085 frees cam wheel 1100 to rotate. Cam wheel 1100 is operatively connected to lever 1080 through drive gear 1150 and clutch 1130. Teeth on lever 1080 mesh with teeth on drive gear 1150. Features on the drive gear 1150 mesh with features on the clutch 1130. Because the clutch 1130 is mated with splines to the cam wheel 1100, the more force that is applied the greater the gripping force will be. Once the lever 1080 is fully squeezed, is able to fully retract to its original position without moving the cam wheel 1100. When the lever 1080 is squeezed inward to its full travel stroke by the user, cam wheel 1100 rotates clockwise 180°. Rotation of the cam wheel 1100 eventually releases firing sled 1060 such that the energy stored in spring 1050 causes firing sled 1060 move rapidly forward and drive the needle out from the distal end of cartridge 1200 and into tissue. FIG. 25D illustrates firing sled 1060 in its forward position in his needle 230 is shown advanced from the distal end of the cartridge 1200.

Figure 25E:
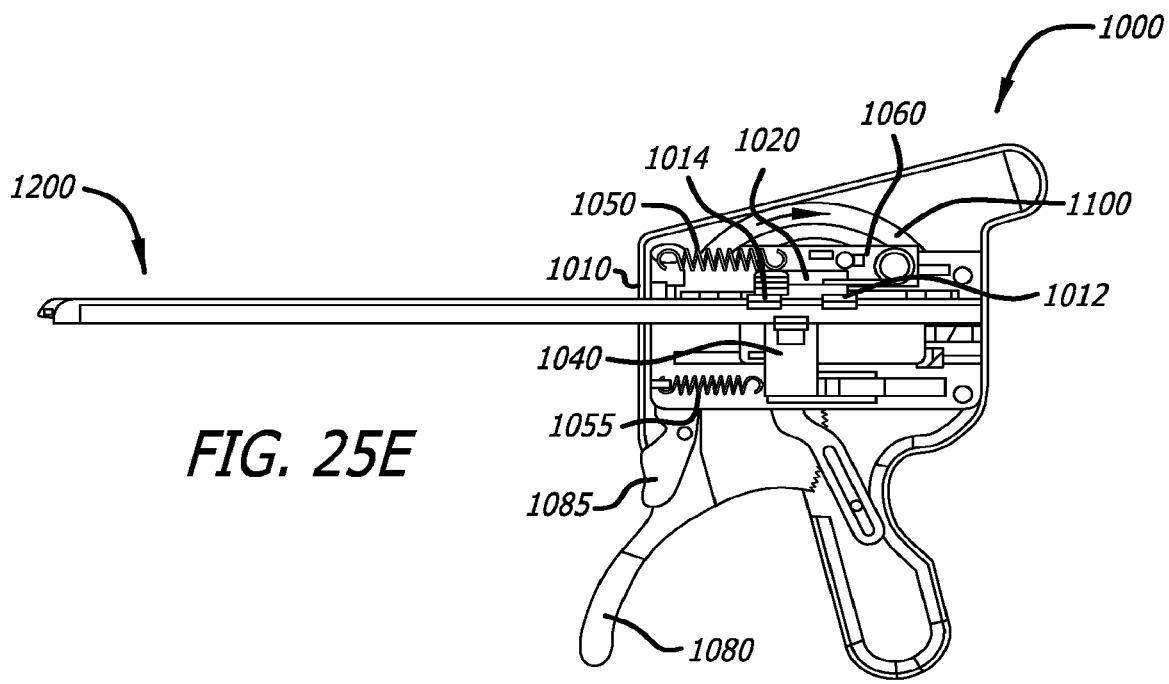
Figure 25F:
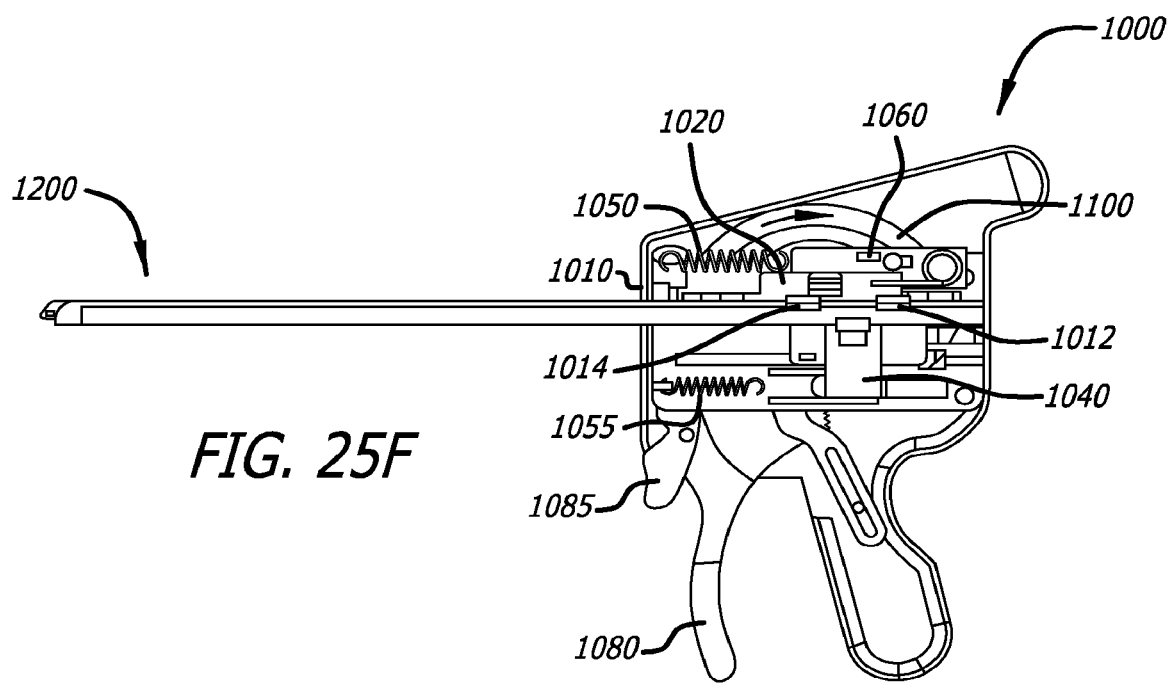

As depicted in FIGS. 25E-25F, as the user continues to squeeze the lever 1080 cam wheel 1100 continues to rotate and pulls back the firing sled 1060. Connector sled 1020 remains in a forward position as the firing sled 1060 is pulled proximally, which ejects the distal anchor from the end of needle 230. With the remaining travel of lever 1080 as it is squeezed by the user, connector sled 1020 is pulled proximally by the rotating cam wheel 1100 thereby putting tension on the connector. The lever 1080 can now be released back to its initial position while the components inside anchor delivery system handle 1100 remain in place.

Figure 25G:
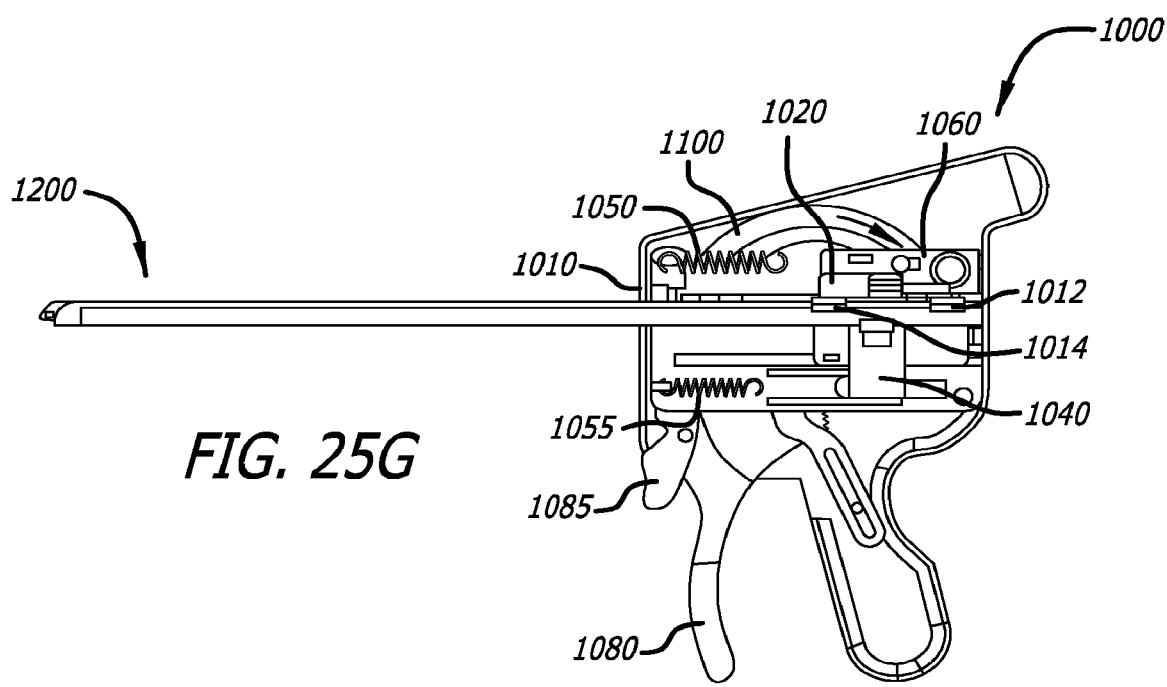
Figure 25H:
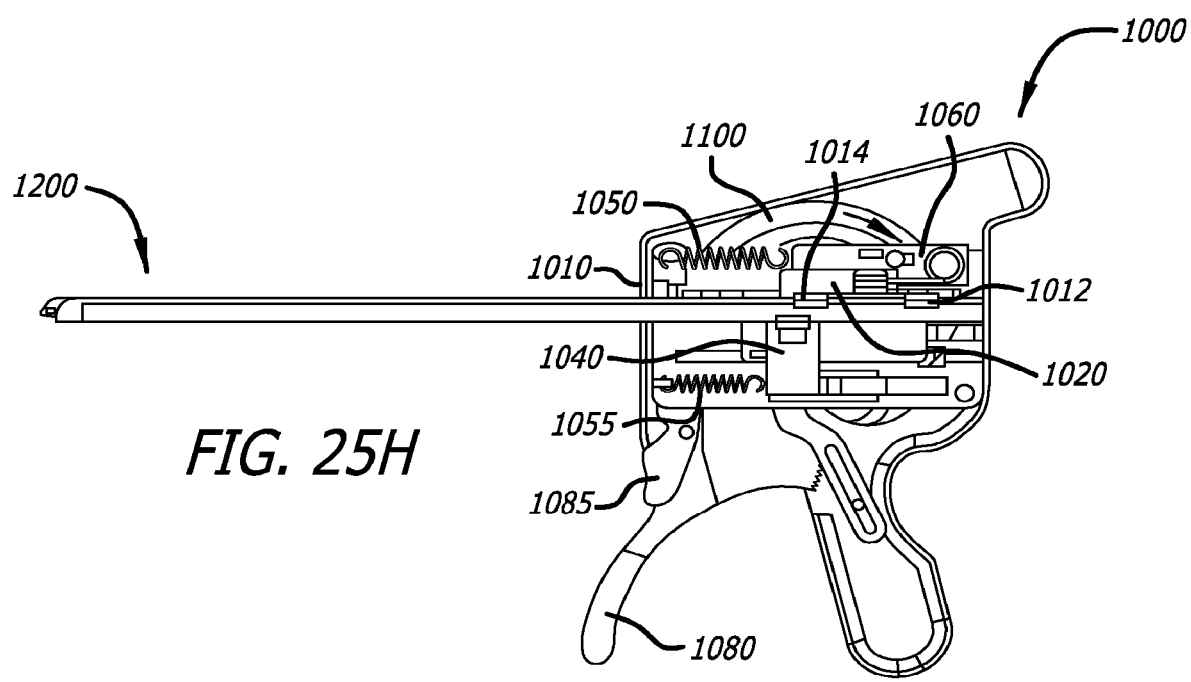

As depicted in FIGS. 25G-25H, with a second squeeze of lever 1080 cam wheel 1100 rotates and disengages a lock on second anchor sled 1040, which is connected to spring 1055. Spring 1055 has been loaded with energy by the rotation of the cam wheel 1100 and now that energy is released through second anchor sled 1040 moving rapidly forward to deliver the second anchor to engage with the connector. This step of firing the second anchor sled 1040 distally also accomplishes cutting the connector through mechanisms disclosed herein.

Figure 25I:
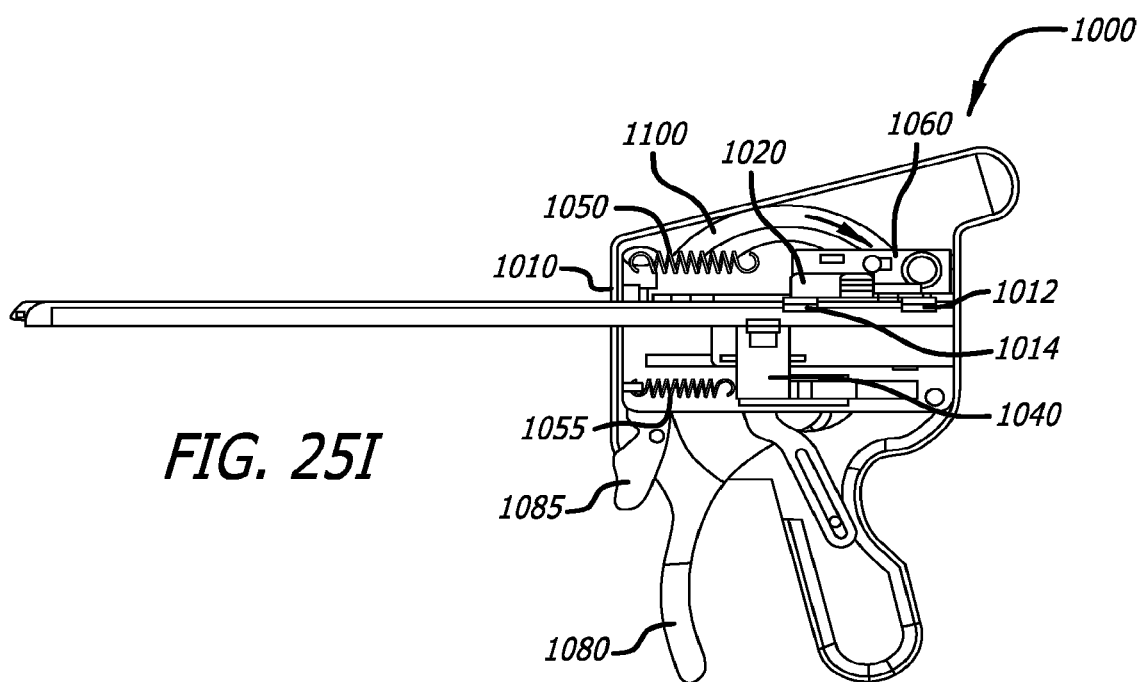
Figure 25J:
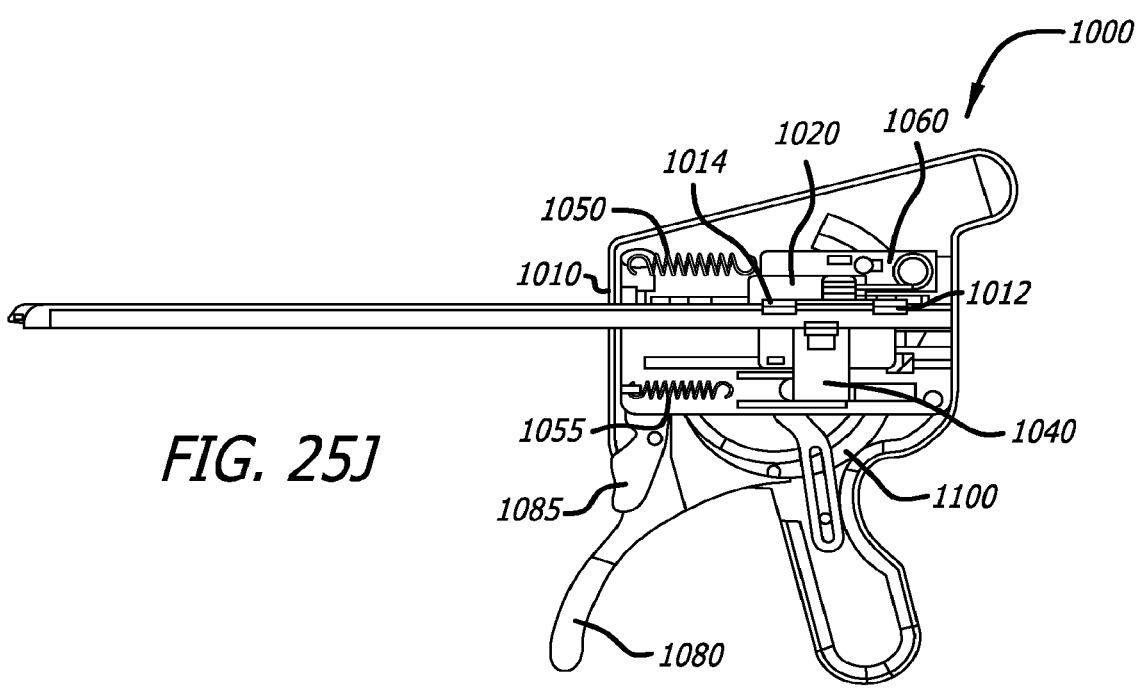
Figure 26A:
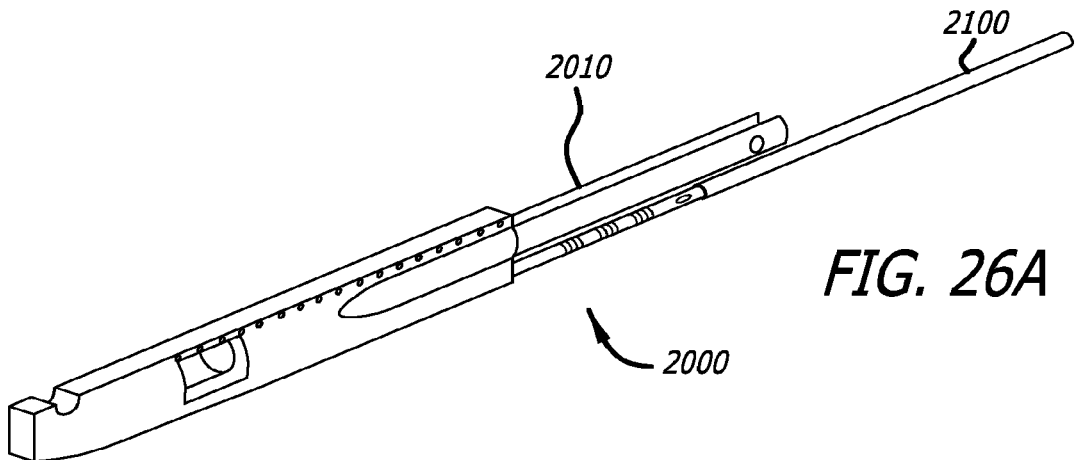
FIGS. 26A-26E are various views of an anchor delivery system that includes cartridges configured to be placed at the distal end of an elongate member of an anchor delivery system.
Figure 26B:
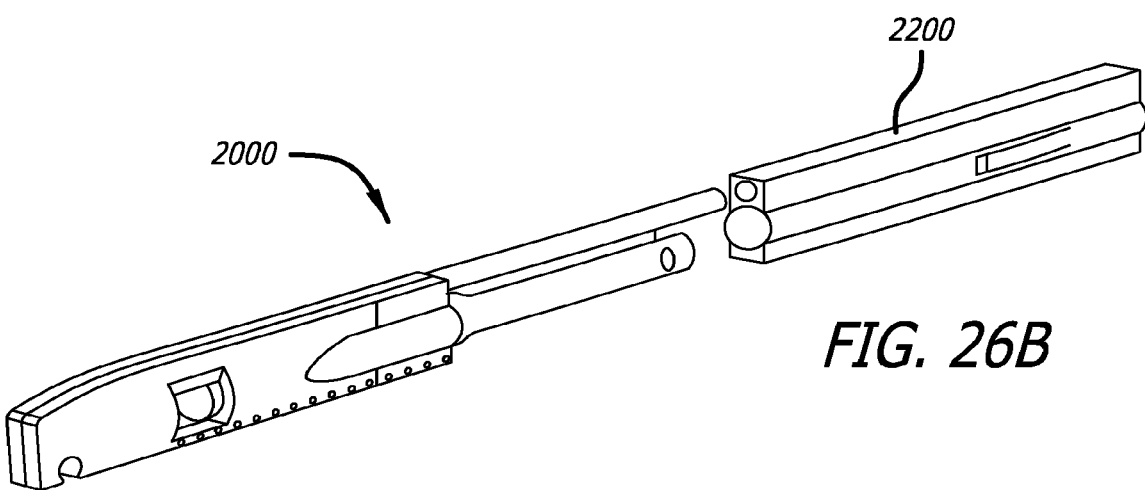
Figure 26C:
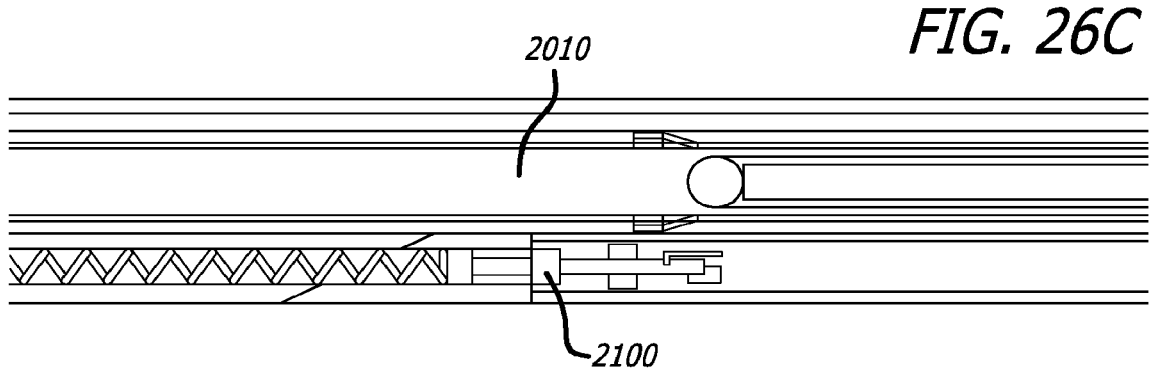
Figure 26D:
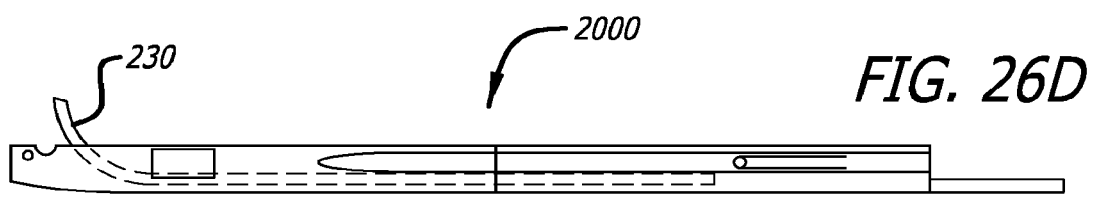
Figure 26E:
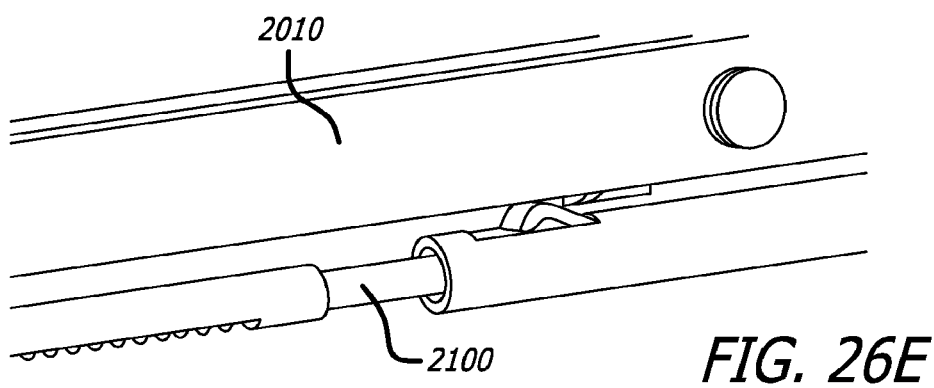

As depicted in FIGS. 25I-25J, when the user continues to squeeze lever 1080 the cam wheel 1100 continues to rotate and returns the second anchor sled 1040 to which initial position. After the lever 1080 is released for the second time, the anchor delivery system handle 1000 is again configured such that the spent cartridge 1200 can be removed and a new cartridge 1200' can be inserted into the handle. The rotating cam wheel 1100 has also returned safety 1085 to its a locked-out position. Alternatively, the lever 1080 and cam wheel 1100 can be configured to rotate the cam wheel 120 degrees with each lever squeeze, requiring three pulls of the lever 1080 to complete the deployment sequence and return to the start position. Alternatively, the cam wheel 1100 and lever 1080 (and gearing) can be designed to rotate the cam wheel unequal amounts with each lever squeeze. For example, in a three-lever pull configuration, the design could enable the first two lever pulls to rotate the wheel 90 degrees each (achieving 180 degrees of rotation after the first two pulls) and the third lever pull then completes the remaining 180 degrees of rotation.

FIGS. 26A-26E illustrate an anchor delivery system including a tip cartridge 2000. The tip cartridge 2000 includes a needle 230 and an anchor assembly including the first anchor the connector and the second anchor. Firing shaft 2100 is configured to mate with a lumen on handle elongate member 2200. Locking arms 2010 also mate with handle elongate number 2200 and provide stability to the joint connecting handle elongate member 2200 and tip cartridge 2000. Activating an actuator on the handle of the anchor delivery system forces firing shaft 2100 distally and advances needle 230. The same or another actuator is activated to retract the needle while maintaining the position of the connector in the distal anchor such that both are deployed within tissue. The connector is tensioned, and the same or another actuator fires the 2nd anchor to engage the connector. Advantageously, this embodiment enables reuse of a single handle with multiple tip cartridges. This embodiment, and embodiments equivalent thereto, efficiently provide the anchor assembly to the distal end of the device.

In some embodiments, a cartridge includes an elongate shaft portion that can attach to the distal end of the scope or the distal end of the sheath. This distal point of attachment can help stabilize and/or secure the distal portion of the elongate portion of the cartridge before or after the cartridge has been inserted into a handle. In some embodiments, a cartridge has structural features such as splines, bosses, arms, standoffs, or similar features that align the cross-sectional position of the cartridge within the sheath. Preferably, such features align the distal end of the cartridge with the distal end of the sheath. Further, the aligning features can be on the scope in addition to or instead of on the cartridge. Preferably, the aligning features permit irrigation fluid flow through the length of the sheath. In some embodiments, the handle need not be separated or adjusted relative to the sheath in order to remove or install a cartridge. In some embodiments, the cartridge is configured such that insertion or removal of the cartridge changes the energy state of at least one of the spring mechanisms in the handle.

Embodiments described herein provide several advantages, including, but not limited to, the ability to efficiently deliver multiple anchor assemblies while reducing patient discomfort and increasing ease-of-use. Certain embodiments provide mechanisms for, with a single lever or equivalent actuator, delivering an anchor assembly and recharging the stored energy in the delivery device such that the device is ready or near ready to deliver another anchor assembly by simply replacing a cartridge in the delivery system.

Accordingly, the present invention contemplates both pushing directly on anchor portions of an anchor assembly as well as pushing directly upon the connector of the anchor assembly. Moreover, as presented above, the distal or first anchor component can be advanced and deployed through a needle assembly and at least one component of the proximal or second anchor component is advanced and deployed from the needle or from a housing portion of the anchor deployment device. Further, either a single anchor assembly or multiple anchor assemblies can be delivered and deployed at an intervention site by the deployment device. Additionally, a single anchor assembly component can for example, be placed on one side of a prostate or urethra while multiple anchor assembly components can be positioned along an opposite or displaced position of such anatomy. The number and locations of the anchor assemblies can thus be equal and/or symmetrical, different in number and asymmetrical, or simply asymmetrically placed. In the context of prostate treatment, the present invention is used for the displacement, compression, and/or retraction of the prostate gland and the opening of the prostatic urethra, the delivering of an implant at the interventional site, and applying tension between ends of the implant. Moreover, drug delivery is both contemplated and described as a further remedy in BPH and over active bladder treatment as well as treating prostate cancer and prostatitis.

Once implanted, the anchor assembly of the present invention accomplishes desired tissue manipulation, approximation, compression or retraction as well as cooperates with the target anatomy to provide an atraumatic support structure. In one preferred embodiment, the shape and contour of the anchor assembly is configured so that the assembly invaginates within target tissue, such as within folds formed in the urethra by the opening of the urethra lumen by the anchor assembly. In desired placement, wispy or pillowy tissue in the area collapses around the anchor structure. Eventually, the natural tissue can grow over the anchor assembly and new cell growth occurs over time. Such cooperation with target tissue facilitates healing and avoids unwanted side effects such as calcification or infection at the interventional site.

Subsequent to the interventional procedure, the patient can be directed to take appropriate drugs or therapeutic agents, such as alpha blockers and anti-inflammatory medicines.

Furthermore, in addition to an intention to cooperate with natural tissue anatomy, the present invention also contemplates approaches to accelerate healing or induce scarring. Manners in which healing can be promoted can include employing abrasive materials, textured connectors, biologics and drugs.

Additionally, it is contemplated that the components of the anchor assembly or selected portions thereof (of any of the anchor assemblies described or contemplated), can be coated or embedded with therapeutic or diagnostic substances (e.g. drugs or therapeutic agents). Again, in the context of treating a prostate gland, the anchor assembly can be coated or imbedded with substances such as 5-alpha-reductase which cause the prostate to decrease in size. Other substances contemplated include but are not limited to phytochemicals generally, alpha-1a-adrenergic receptor blocking agents, smooth muscle relaxants, and agents that inhibit the conversion of testosterone to dihydrotestosterone. In one particular approach, the connector can for example, be coated with a polymer matrix or gel coating that retains the therapeutic or diagnostic substance and facilitates accomplishing the timed release thereof. Additionally, it is contemplated that bacteriostatic coatings as well as analgesics and antibiotics for prostatitis and other chemical coatings for cancer treatment, can be applied to various portions of the anchor assemblies described herein. Such coatings can have various thicknesses or a specific thickness such that it along with the connector itself matches the profile of a cylindrical portion of an anchor member affixed to the connector. Moreover, the co-delivery of a therapeutic or diagnostic gel or other substances through the implant deployment device or another medical device (i.e. catheter), and moreover an anchor assembly including the same, is within the scope of the present invention as is radio-loading devices (such as a capsular or distal ends of implants for cancer or other treatment modalities). In one such approach, the deployment device includes a reservoir holding the gel substance and through which an anchor device can be advance to pick up a desired quantity of therapeutic or diagnostic gel substance.

It is further contemplated that in certain embodiments, the anchor delivery device can include the ability to detect forces being applied thereby or other environmental conditions. Various sections of the device can include such devices and in one contemplated approach sensors can be placed along the needle assembly. In this way, an operator can detect for example, whether the needle has breached the target anatomical structure at the interventional site and the extent to which such breaching has occurred. Other sensors that can detect particular environmental features can also be employed such as blood or other chemical or constituent sensors. Moreover, one or more pressure sensors or sensors providing feedback on the state of deployment of the anchor assembly during delivery or after implantation are contemplated. For example, tension or depth feedback can be monitored by these sensors. Further, such sensors can be incorporated into the anchor assembly itself, other structure of the deployment device or in the anatomy.

Moreover, it is to be recognized that the foregoing procedure is reversible. In one approach, the connection of an anchor assembly can be severed and a proximal (or second) anchor component removed from the patient's body. For example, the physician can cut the connector and simultaneously remove the second anchor previously implanted for example, in the patient's urethra using electrosurgical, surgical or laser surgical devices used in performing transurethral prostate resection.

An aspect that the various embodiments of the present invention provide is the ability to deliver an anchor assembly having a customizable length, each anchor assembly being implanted at a different location without having to remove the device from the patient. Other aspects of the various embodiments of the present invention are load-based delivery, of an anchor assembly, anchor assembly delivery with a device having integrated connector, (e.g. suture), cutting, and anchor assembly delivery with an endoscope in the device. The delivery device is uniquely configured to hold the suture with tension during delivery to help ensure that the first anchor component sits firmly against a tissue plane (e.g., the outer capsule of the prostate) and is held relatively firm as the second anchor component is attached to the connector and the delivery device. In this aspect, the needle assembly acting as a penetrating member is cooperatively connected to a mechanism that pulls on the anchor while the needle assembly is retracted.

It is to be recognized that various materials are within the scope of the present invention for manufacturing the disclosed devices. Moreover, one or more components such as distal anchor, proximal anchor, and connector, of the one or more anchor devices disclosed herein can be completely or partially biodegradable or biofragmentable.

Further, as stated, the devices and methods disclosed herein can be used to treat a variety of pathologies in a variety of lumens or organs comprising a cavity or a wall. Examples of such lumens or organs include, but are not limited to urethra, bowel, stomach, esophagus, trachea, bronchii, bronchial passageways, veins (e.g. for treating varicose veins or valvular insufficiency), arteries, lymphatic vessels, ureters, bladder, cardiac atria or ventricles, uterus, fallopian tubes, etc.

Finally, it is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unpatentable or unsuitable for its intended use. Also, for example, where the steps of a method are described or listed in a particular order, the order of such steps may be changed unless to do so would render the method unpatentable or unsuitable for its intended use. All reasonable additions, deletions, modifications and alterations are to be considered equivalents of the described examples and embodiments and are to be included within the scope of the following claims.

Thus, it will be apparent from the foregoing that, while particular forms of the invention have been illustrated and described, various modifications can be made without parting from the spirit and scope of the invention.

We claim:

1. A system for deploying an anchor assembly, comprising:
    a cartridge having a needle configured to carry the anchor assembly, wherein the cartridge comprises a tab connected with the needle;
    a handle comprising a sled connected to a spring mechanism and the sled includes a slot, wherein the handle is configured to couple with the cartridge such that the slot on the sled aligns with the tab and the slot and the tab are a complementary mechanism that allows a transfer of mechanical energy from the spring via the sled to the cartridge; and
    a single actuator configured to initiate the transfer of the mechanical energy to cause the sled to move rapidly forward and drive the needle out from a distal end of the cartridge.

2. The system of claim 1 wherein the single actuator is configured to restore a majority of the mechanical energy.

3. The system of claim 2 wherein the single actuator is configured to be activated more than one time to completely deploy the anchor assembly and restore the majority of the mechanical energy.

4. The system of claim 2 wherein the single actuator is configured to restore mechanical energy to the at least one spring mechanism sufficient to deploy a second anchor assembly from a second cartridge.

5. The system of claim 1 wherein the cartridge is removable from the handle without releasing the mechanical energy in the spring mechanism.

6. The system of claim 1 wherein the anchor assembly comprises a first anchor, a connector, and a second anchor.

7. The system of claim 1 wherein the cartridge further comprises an elongate member configured to access an interventional site adjacent a prostate.

8. The system of claim 1 where the anchor assembly includes a customizable-length connector element.

9. The system of claim 1 further comprising a scope, wherein the cartridge is configured such that insertion and removal of the cartridge can be completed without removal or adjustment to the scope.

* * * * *